US008329986B2

(12) United States Patent
Butler et al.

(10) Patent No.: US 8,329,986 B2
(45) Date of Patent: Dec. 11, 2012

(54) TARGETED INTEGRATION INTO THE ZP15 LOCUS

(75) Inventors: Holly J. Butler, Indianapolis, IN (US); David R. Corbin, Indianapolis, IN (US); Yannick Doyon, El Cerrito, CA (US); Zhifang Gao, Indianapolis, IN (US); Vipula K. Shukla, Indianapolis, IN (US); Fyodor Urnov, Point Richmond, CA (US); Sarah E. Worden, Indianapolis, IN (US)

(73) Assignees: Dow AgroSciences, LLC, Indianapolis, IN (US); Sangamo BioSciences, Inc., Richmond, CA (US)

( * ) Notice: Subject to any disclaimer, the term of this patent is extended or adjusted under 35 U.S.C. 154(b) by 157 days.

(21) Appl. No.: 12/653,735

(22) Filed: Dec. 17, 2009

(65) Prior Publication Data

US 2010/0199389 A1  Aug. 5, 2010

Related U.S. Application Data

(60) Provisional application No. 61/201,946, filed on Dec. 17, 2008.

(51) Int. Cl.
*A01H 1/00* (2006.01)
*A01H 5/00* (2006.01)
*A01H 5/10* (2006.01)
*C12N 5/04* (2006.01)
*C12N 15/00* (2006.01)
*C12N 15/82* (2006.01)
*C12N 15/87* (2006.01)

(52) U.S. Cl. ........ 800/278; 800/260; 800/279; 800/281; 800/284; 800/303; 800/300.1; 800/320.1; 435/419; 435/440; 435/463; 435/468

(58) Field of Classification Search .................. None
See application file for complete search history.

(56) References Cited

U.S. PATENT DOCUMENTS

| | | | |
|---|---|---|---|
| 5,356,802 A | 10/1994 | Chandrasegaran | |
| 5,420,032 A | 5/1995 | Marshall et al. | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,824,978 B1 | 11/2004 | Cox et al. | |
| 6,833,252 B1 | 12/2004 | Dujon et al. | |
| 6,933,113 B2 | 8/2005 | Case | |
| 2003/0068675 A1* | 4/2003 | Liu | ............... 435/69.1 |
| 2003/0232410 A1 | 12/2003 | Liljedahl et al. | |
| 2005/0026157 A1 | 2/2005 | Baltimore et al. | |
| 2005/0064474 A1* | 3/2005 | Urnov et al. | ...................... 435/6 |
| 2005/0208489 A1 | 9/2005 | Carroll et al. | |
| 2006/0188987 A1 | 8/2006 | Guschan et al. | |
| 2007/0117128 A1 | 5/2007 | Smith et al. | |
| 2007/0134796 A1 | 6/2007 | Holmes et al. | |
| 2008/0182332 A1 | 7/2008 | Cai et al. | |
| 2009/0093366 A1 | 4/2009 | Wright et al. | |
| 2009/0104700 A1 | 4/2009 | Samuel et al. | |
| 2009/0111119 A1 | 4/2009 | Doyon et al. | |
| 2009/0205083 A1 | 8/2009 | Gupta et al. | |
| 2009/0263900 A1 | 10/2009 | DeKelver et al. | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/53480 A1 | 7/2001 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2005/084190 A2 | 9/2005 |
| WO | WO 2006/071219 A1 | 7/2006 |
| WO | WO 2006/097854 A1 | 9/2006 |
| WO | WO 2007/014275 A2 | 1/2007 |
| WO | WO 2007/139898 A2 | 12/2007 |
| WO | WO 2008/133938 A2 | 11/2008 |

OTHER PUBLICATIONS

Soave et al, Genes for Zein Subunits on Maize Chromosone 4, 1982, Biochemical Genetics 20:1027-1038.* Argast, et al., "I-PPOI and I-CREI Homing Site Sequence Degeneracy Determined by Random Mutagenesis and Sequential in Vitro Enrichment," *J. Mol. Biol.* 280:345-353 (1998).
Armstrong, et al., "Development and Availability of Germplasm With High Type II Culture Formation," *Maize Genet Coop News Lett* 65:92-93 (1991).
Ashworth, et al., "Computational Redesign of Endonuclease DNA Binding and Cleavage Specificity," *Nature* 441:656-659 (2006).
Belfort, et al., "Homing Endonucleases: Keeping the House in Order," *Nucleic Acids Research* 25:3379-3388 (1997).
Bibikova, et al., "Stimulation of Homologous Recombination Through Targeted Cleavage by Chimeric Nucleases," *Mol. Cell. Biol.* 21:289-297 (2001).
Bitinate, et al., "Foki Dimerization is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Chang, et al., "Modification of DNA Ends Can Decrease End Joining Relative to Homologous Recombination in Mammalian Cells," *PNAS USA* 84:4959-4963 (1987).
Chevalier, et al., "Design, Activity, and Structure of a Highly Specific Artificial Endonuclease," *Molecular Cell* 10:895-905 (2002).

(Continued)

*Primary Examiner* — Eileen B O Hara
(74) *Attorney, Agent, or Firm* — Pasternak Patent Law; Dahna S. Pasternak

(57) ABSTRACT

Disclosed herein are methods and compositions for targeted integration of an exogenous sequence into a plant Zp15 locus, for example, for expression of a polypeptide of interest.

15 Claims, 21 Drawing Sheets

OTHER PUBLICATIONS

Christensen, et al., "Maize Polyubiquitin Genes: Structure, Thermal Perturbation of Expression and Transcript Slicing, and Promotoer Activity Following Transfer to Protoplasts by Electroportation," *Plant Mol Biol.* 18(4):675-689 (1992).

D'Halluin, et al., "Homologous Recombination: A Basis for Targeted Genome Optimization in Crop Species Such as Maize," *Plant Biotechnology J.* 6:93-102 (2008).

Doyon, et al., "Heritable Targeted Gene Disruption in Zebrafish Using Designed Zinc-Finger Nucleases," *Nature Biotechnology* 26:702-708 (2008).

Dujon, et al., "Mobile Introns: Definition of Terms and Recommended Nomenclature," *Gene* 82:115-118 (1989).

Epinat, et al., "A Novel Engineered Meganuclease Induces Homologous Recombination in Yeast and Mammalian Cells," *Nucleic Acids Research* 31:2952-2962 (2003).

Frame, et al., "*Agrobacterium tumefaciens*-Mediated Transformation of Maize Embryos Using a Standard Binary Vector System," *Plant Physiol.* 129:13-22 (2002).

Gimble, et al., "Substrate Recognition and Induced DNA Distortion by the PI-SCEI Endonuclease, An Enzyme Generated by Protein Splicing," *J. Mol. Biol.* 263:163-180 (1996).

Gordon-Kamm, et al., "Transformation of Maize Cells and Regeneration of Fertile Transgenic Plants," *Plant Cell* 2:603-618 (1990).

Iida, et al., "Modification of Endogenous Natural Genes by Gene Targeting in Rice and Other Higher Plants," *Plant Mol. Biol.* 59:205-219 (2005).

Jasin, et al., "Genetic Manipulation of Genomes With Rare-Cutting Endonucleases," *Trends Genet* 12:224-228 (1996).

Kim, et al., "Chimeric Restriction Endonuclease," *PNAS USA* 91:883-887 (1994).

Kim, et al., "Insertion and Deletion Mutants of Foki Restriction Endonuclease," *J. Biol. Chem.* 269:31978-31982 (1994).

Kim, et al., "Hybrid Restriction Enzymes: Zinc Finger Fusions to Fok I Cleavage Domain," *Proc. Natl Acad. Sci. USA* 93:1156-1160 (1996).

Lawrence, et al., "Maizegdb, The Community Database for Maize Genetics and Genomics," *Nucleic Acids Research* 32:393-397 (2004).

Li, et al., "Functional Domains in Fok I Restriction Endonuclease," *PNAS USA* 89:4275-4279 (1992).

Li, et al., "Alteration of the Cleavage Distance of Fok I Restriction Endonuclease by Insertion Mutagenesis," *PNAS USA* 90:2764-2768 (1993).

Lloyd, A. et al., "Targeted Mutagenesis Using Zinc-Finger Nucleases in *Arabidopsis*," *Proc. Natl Acad. Sci. USA* 102:2232-2237 (2005).

Maeder, et al., "Rapid "Open-Source" Engineering of Customized Zincfinger Nucleases for Highly Efficient Gene Modification," *Mol. Cell* 31:294-301 (2008).

McElroy, et al., "Isolation of an Efficient Actin Promotor for Use in Rice Transformation," *The Plant Cell* 2:163-171 (1990).

Miller, et al., "Repetitive Zinc-Binding Domains in the Protein Transcription Factor IIIA From *Xenopus oocytes*," *EMBO J.* 4:1609-1614 (1985).

Miller, et al., "Rearrangement of Side-Chains in a ZIF268 Mutant Highlights the Complexities of Zinc Finger DNA Recognition," *J Mol Biol.*, 313(2):309 (2001).

Miller, et al., "An Improved Zinc-Finger Nuclease Architecture for Highly Specific Genome Editing," *Nat Biotechnology* 25:778-785 (2007).

Moscou, et al., "A Simple Cipher Governs DNA Recognition by TAL Effectors," *Science* 326:1501 (2009).

Nehls, et al., "Two Genetically Separable Steps in the Differentiation of Thymic Epithelium," *Science* 272:886-889 (1996).

Paques, et al., "Meganucleases and DNA Double-Strand Break-Induced Recombination: Perspectives for Gene Therapy," *Current Gene Therapy* 7:49-66 (2007).

Perler, et al., "Protein Splicing Elements: Inteins and Exteins a Definition of Terms and Recommended Nomenclature," *Nucleic Acids Research* 22:1125-1127 (1994).

Petolino, et al., "Whisker-Mediated Transformation of Embryogenic Callus of Maize," *Plant Cell Rept.* 19:781-786 (2000).

Porteus, et al., "Chimeric Nucleases Stimulate Gene Targeting in Human Cells" *Science* 300:763 (2003).

Puchta, H.,"Gene Replacement by Homologous Recombination in Plants," *Plant Mol. Biol.* 48:173-182 (2002).

Puchta, H., "The Repair of Double-Strand Breaks in Plants: Mechanisms and Consequences for Genome Evolution," *J. Exp. Bot.* 56:1-14 (2005).

Rhodes, et al., "Zinc Fingers: They Play a Key Part in Regulating the Activity of Genes in Many Species, From Yeast to Humans. Fewer Than 10 Years Ago no on Knew They Existed." *Scientific American* 268:56-65 (1993).

Shukla, et al., "Precise Genome Modification in the Crop Species *Zea mays* Using Zinc-Finger Nucleases," *Nature* 459:437-441 (2009) with Supplementary on-line material.

Terada, et al., "Efficient Gene Targeting by Homologous Recombination in Rice," *Nat Biotechnology* 20:1030-1034 (2002).

Terada, et al., "Gene Targeting by Homologous Recombination as a Biotechnological Tool for Rice Functional Genomics," *Plant Physiol* 144:846-856 (2007).

Tovkach, et al., "A Toolbox and Procedural Notes for Characterizing Novel Zinc Finger Nucleases for Genome Editing in Plant Cells," *Plant J* 57:747-757 (2009).

Urnov, et al., "Highly Efficient Endogenous Human Gene Correction Using Designed Zinc-Finger Nucleases," *Nature* 435:646-651 (2005).

Wei, et al., "Physical and Genetic Structure of the Maize Genome Reflects Its Complex Evolutionary History," *PLoS Genet.* 3:1254-1263 (2007).

Wohlleben, et al., "Nucleotide Sequence of the Phosphinothricin N-Acetyltransferase Gene From Streptomyces Virido-Chromogenes TU494 and Its Expression in *Nicotiana tabacum*," *Gene* 70(1):25-37 (1988).

Woo, et al., "Genomics Analysis of Genes Expressed in Maize Endosperm Identifies Novel Seed Proteins and Clarifies Patterns of Zein Gene Expression," *Plant Cell* 13:2297-2317 (2001).

Wright, et al., "High-Frequency Homologous Recombination in Plants Mediated by Zinc-Finger Nucleases," *Plant J.* 44:693-705 (2005).

\* cited by examiner

Figure 1

```
Zp15genomic (SEQ ID NO:129):
GTGCAGCCCGCTGGCGGGCGGGGCGGCCCTACTACGCCG::::::GGTGTGGGCAGCCGAGCGCCATGTTCCAGCCGCTC Plate7 B10(SEQ ID NO:130):
GTGCAGCCCGCTGGCGGGCGGGGCGGCCCTACTACGCCGGCAATTGGTGTGGGCAGCCGAGCGCCATGTTCCAGCCGCTC (+6)
                                   11768                   11766
```

Figure 2

```
Zp15 Genomic (SEQ ID NO:131):
ATGGGCGCCGGGGGCTGTACCCCTACGCGGAGTACCTGAGGCAGCCCGCTGAGCCCGCTGGCGGGCGGCGCCCT Plate6 C12 (SEQ ID NO:132):
ATGGGCGCCGGGGGCTGTACCCCTACGCGGAG:::CTGAGGCAGCCCGCTGAGCCCGCTGGCGGCGGCGCCCT (Δ3)
              11753                  11750
```

FIGURE 6A

```
Zp15 WT Genomic Locus (SEQ ID NO:133)   (1) CATACTGTTGCTGCCCTGCTGGAATAAATGTGCTACTTTCCCCTGCCTTG
   Zp15 donor fragment (SEQ ID NO:134)   (1) --------------------------------------------------
         147_5'_Border (SEQ ID NO:135)   (1) CATACTGTTGCTGCCCTGCTGGAATAAATGTGCTACTTTCCCCTGCCTTG
         147_3'_Border (SEQ ID NO:136)   (1) --------------------------------------------------
                                             51                                              100
Zp15 WT Genomic Locus                   (51) TTAAGGGAAAGGGTTTTGTTCACGATGTTACCTTGTAACCTTGTACTTAT
   Zp15 donor fragment                   (1) --------------------------------------------------
         147_5'_Border                  (51) TTAAGGGAAAGGGTTTTGTTCACGATGTTACCTTGTAACCTTGTACTTAT
         147_3'_Border                   (1) --------------------------------------------------
                                             101                                             150
Zp15 WT Genomic Locus                  (101) GTTTCATACTTGGAATGAAGGTTCATGGAACAAAAATATTCTGCTGCATT
   Zp15 donor fragment                   (1) --------------------------------------------------
         147_5'_Border                 (101) GTTTCATACTTGGAATGAAGGTTCATGGAACAAAAATATTCTGCTGCATT
         147_3'_Border                   (1) --------------------------------------------------
                                             151                                             200
Zp15 WT Genomic Locus                  (151) GCATGCAAGAGCTGTTGATCATTCAGAGCAATGTATTGGTTGTGAGTTTT
   Zp15 donor fragment                   (1) GCATGCAAGAGCTGTTGATCATTCAGAGCAATGTATTGGTTGTGAGTTTT
         147_5'_Border                 (151) GCATGCAAGAGCTGTTGATCATTCAGAGCAATGTATTGGTTGTGAGTTTT
         147_3'_Border                   (1) --------------------------------------------------
                                             201                                             250
Zp15 WT Genomic Locus                  (201) TGACGGCGCTCACAGTGATAGATTTGTTATCTATATGCCAGCCCCAGCAT
   Zp15 donor fragment                  (51) TGACGGCGCTCACAGTGATAGATTTGTTATCTATATGCCAGCCCCAGCAT
         147_5'_Border                 (201) TGACGGCGCTCACAGTGATAGATTTGTTATCTATATGCCAGCCCCAGCAT
         147_3'_Border                   (1) --------------------------------------------------
                                             251                                             300
Zp15 WT Genomic Locus                  (251) ATTCATCCTTGTGCTGTGGGCGTCTAGAGGACCGACAATATATATATTTT
   Zp15 donor fragment                 (101) ATTCATCCTTGTGCTGTGGGCGTCTAGAGGACCGACAATATATATATTTT
         147_5'_Border                 (251) ATTCATCCTTGTGCTGTGGGCGTCTAGAGGACCGACAATATATATATTTT
         147_3'_Border                   (1) --------------------------------------------------
                                             301                                             350
Zp15 WT Genomic Locus                  (301) TAAAACAAATTCGTGAAGAACATCACAAGTTATGCATGCAAACTGCTCAA
   Zp15 donor fragment                 (151) TAAAACAAATTCGTGAAGAACATCACAAGTTATGCATGCAAACTGCTCAA
         147_5'_Border                 (301) TAAAACAAATTCGTGAAGAACATCACAAGTTATGCATGCAAACTGCTCAA
         147_3'_Border                   (1) --------------------------------------------------
                                             351                                             400
Zp15 WT Genomic Locus                  (351) GTCATGTGGATCCAAGGCATCCTAACAACTAGCACAGCATTACAACAAAA
   Zp15 donor fragment                 (201) GTCATGTGGATCCAAGGCATCCTAACAACTAGCACAGCATTACAACAAAA
         147_5'_Border                 (351) GTCATGTGGATCCAAGGCATCCTAACAACTAGCACAGCATTACAACAAAA
         147_3'_Border                   (1) --------------------------------------------------
                                             401                                             450
Zp15 WT Genomic Locus                  (401) TATTGGTGTATATGTGCCTACAATGAAGTGAAAGGTGATGAGTCATGGTG
   Zp15 donor fragment                 (251) TATTGGTGTATATGTGCCTACAATGAAGTGAAAGGTGATGAGTCATGGTG
         147_5'_Border                 (401) TATTGGTGTATATGTGCCTACAATGAAGTGAAAGGTGATGAGTCATGGTA
         147_3'_Border                   (1) --------------------------------------------------
                                             451                                             500
Zp15 WT Genomic Locus                  (451) ATGTGTAAAGAGGCATTACAAAGTTAGCTTCACAAGCGTATGAATTCATT
   Zp15 donor fragment                 (301) ATGTGTAAAGAGGCATTACAAAGTTAGCTTCACAAGCGTATGAATTCATT
         147_5'_Border                 (451) ATGTGTAAAGAGGCATTACAAAGTTAGCTTCACAAGCGTATGAATTCATT
         147_3'_Border                   (1) --------------------------------------------------
                                             501                                             550
Zp15 WT Genomic Locus                  (501) GACAACCCTTGACATGTAAAGTTGATTCATATGTATAAGAAAGCTTAATG
   Zp15 donor fragment                 (351) GACAACCCTTGACATGTAAAGTTGATTCATATGTATAAGAAAGCTTAATG
         147_5'_Border                 (501) GACAACCCTTGACATGTAAAGTTGATTCATATGTATAAGAAAGCTTAATG
         147_3'_Border                   (1) --------------------------------------------------
                                             551                                             600
Zp15 WT Genomic Locus                  (551) ATCTATCTGTAAATCCAAATCCATGTACTATGTTTCCACGTCATGCAACG
   Zp15 donor fragment                 (401) ATCTATCTGTAAATCCAAATCCATGTACTATGTTTCCACGTCATGCAACG
         147_5'_Border                 (551) ATCTATCTGTAAATCCAAATCCATGTACTATGTTTCCACGTCATGCAACG
         147_3'_Border                   (1) --------------------------------------------------
                                             601                                             650
Zp15 WT Genomic Locus                  (601) CAACATTCCAAAACCATGGGTTGCAAGATGCTGCAGAATGCAAGCCATGG
   Zp15 donor fragment                 (451) CAACATTCCAAAACCATGGGTTGCAAGATGCTGCAGAATGCAAGCCATGG
         147_5'_Border                 (601) CAACATTCCAAAACCATGGGTCGCAAGATGCTGCAGAATGCAAGCCATGG
         147_3'_Border                   (1) --------------------------------------------------
                                             651                                             700
Zp15 WT Genomic Locus                  (651) ATCATCTATAAATGGCTAGCTCCCACATATGAACTAGTCTCTATCATCAT
   Zp15 donor fragment                 (501) ATCATCTATAAATGGCTAGCTCCCACATATGAACTAGTCTCTATCATCAT
```

FIGURE 6B

```
        147_5'_Border    (651) ATCATCTATAAATGGCTAGCTCCCACATATGAACTAGTCTCTATCATCAT
        147_3'_Border      (1) --------------------------------------------------
                                701                                              750
    Zp15 WT Genomic Locus  (701) CCAATCGAGATCAGCAAAGCGGCAGTGCGTAGAGAGGATCGTCGAACAGA
       Zp15 donor fragment (551) CCAATCGAGATCAGCAAAGCGGCAGTGCGTAGAGAGGATCGTCGAACAGA
        147_5'_Border     (701) CCAATCGAGATCAGCAAAGCGGCAGTGCGTAGAGAGGATCGTCGAACAGA
        147_3'_Border      (1) --------------------------------------------------
                                751                                              800
    Zp15 WT Genomic Locus  (751) ACAGCATGAAGATGGTCATCGTTCTCGTCGTGTGCCTGGCTCTGTCAGCT
       Zp15 donor fragment (601) ACAGCATGAAGATGGTCATCGTTCTCGTCGTGTGCCTGGCTCTGTCAGCT
        147_5'_Border     (751) ACAGCATGAAGATGGTCATCGTTCTCGTCGTGTGCCTGGCTCTGTCAGCT
        147_3'_Border      (1) --------------------------------------------------
                                801                                              850
    Zp15 WT Genomic Locus  (801) GCCAGCGCCTCTGCAATGCAGATGCCCTGCCCCTGCGCGGGGCTGCAGGG
       Zp15 donor fragment (651) GCCAGCGCCTCTGCAATGCAGATGCCCTGCCCCTGCGCGGGGCTGCAGGG
        147_5'_Border     (801) GCCAGCGCCTCTGCAATGCAGATGCCCTGCCCCTGCGCGGGGCTGCAGGG
        147_3'_Border      (1) --------------------------------------------------
                                851                                              900
    Zp15 WT Genomic Locus  (851) CTTGTACGGCGCTGGCGCCGGCCTGACGACGATGATGGGCGCCGGCGGGC
       Zp15 donor fragment (701) CTTGTACGGCGCTGGCGCCGGCCTGACGACGATGATGGGCGCCGGCGGGC
        147_5'_Border     (851) CTTGTACGGCGCTGGCGCCGGCCTGACGACGATGATGGGCACCGGCGGGC
        147_3'_Border      (1) --------------------------------------------------
                                901                                              950
    Zp15 WT Genomic Locus  (901) TGTACCGCTACGCGGAGTACCTGAGGCAGCCGCAGTGCAGCCCGCTGGCG
       Zp15 donor fragment (751) TGTACCCCTACGCGGAGTACCTGAGGCAGCCGCAGTGCAGCCCGCTGGCG
        147_5'_Border     (901) TGTACCCCTACGCGGAGTACCTGAGGCAGCCGCAGTGCAGCCCGCTGGCG
        147_3'_Border      (1) --------------------------------------------------
                                951                                             1000
    Zp15 WT Genomic Locus  (951) GCGGCGCCCTACTACGCCG-------------------------------
       Zp15 donor fragment (801) GCGGCGCCCTACTACGCCGGCAATTGAGCACTTAAAGATCTTTAGAAGAA
        147_5'_Border     (951) GCGGCGCCCTACTACGCCGGCAATTGAGCACTTAAAGATCTTTAGAAGAA
        147_3'_Border      (1) --------------------------------------------------
                                1001                                            1050
    Zp15 WT Genomic Locus  (970) --------------------------------------------------
       Zp15 donor fragment (851) AGCAAAGCATTTATTAATACATAACAATGTCCAGGTAGCCCAGCTGAATT
        147_5'_Border    (1001) AGCAAAGCATTTATTAATACATAACAATGTCCAGGTAGCCCAGCTGAATT
        147_3'_Border      (1) --------------------------------------------------
                                1051                                            1100
    Zp15 WT Genomic Locus  (970) --------------------------------------------------
       Zp15 donor fragment (901) ACAATACGCAACTGCTCATAATAATTCAACAAAGCCAAGTAGTACACAAC
        147_5'_Border    (1051) ACAATACGCAACTGCTCATAATAATTCAACAAACCCAAGTAGTACACAAC
        147_3'_Border      (1) --------------------------------------------------
                                1101                                            1150
    Zp15 WT Genomic Locus  (970) --------------------------------------------------
       Zp15 donor fragment (951) ATCCAGAAGCAAATAAAAGCCCATACGTACCAAAGCCTACACAAGCAGCAA
        147_5'_Border    (1101) ATCCAGAAGCAAATAAAAGCCCATACGTACCAAAGCCTACACAAGCAGCAA
        147_3'_Border      (1) --------------------------------------------------
                                1151                                            1200
    Zp15 WT Genomic Locus  (970) --------------------------------------------------
       Zp15 donor fragment (1001) CACTCACTGCCAGTGCCGGTGGGTCTTTAAAGCACACGGGCCTTGACCAC
        147_5'_Border    (1151) CACTCACTGCCAGTGCCGGTGGGTCTTTAAAGCACACGGGCCTTGACCAC
        147_3'_Border      (1) --------------------------------------------------
                                1201                                            1250
    Zp15 WT Genomic Locus  (970) --------------------------------------------------
       Zp15 donor fragment (1051) GCGATCCAGCTTGAAACAAACTTGGTAAAATTAAAGCAAACCAGAAGCAC
        147_5'_Border    (1201) GCGATCCAGCTTGAAACAAACTTGGTAAAATTAAAGCAAACCAGAAGCAC
        147_3'_Border      (1) --------------------------------------------------
                                1251                                            1300
    Zp15 WT Genomic Locus  (970) --------------------------------------------------
       Zp15 donor fragment (1101) ACACACGCCAACGCAACGGCTTCTGATCGCGCGCCCAAGGCCCGGCCGGCC
        147_5'_Border    (1251) ACACACGCCAACGCAACGGCTTCTGATCGCGCGCCCAAGGCCCGGCCGGCC
        147_3'_Border      (1) --------------------------------------------------
                                1301                                            1350
    Zp15 WT Genomic Locus  (970) --------------------------------------------------
       Zp15 donor fragment (1151) AGAACGTACGACGGACACGCACACGCTGCGACCGAGCTCTAGGTGATTAA
        147_5'_Border    (1301) AGAACGTACGACGGACACGCACACGCTGCGACCGAGCTCTAGGTGATTAA
```

FIGURE 6C

```
        147_3'_Border      (1) --------------------------------------------------
                               1351                                           1400
   Zp15 WT Genomic Locus  (970) --------------------------------------------------
      Zp15 donor fragment (1201) GCTAACTACTCAGCGGGCAGGCCTAACTCCACCAACTGTGGTGCGAGTCA
           147_5'_Border  (1351) GCTAACTACTCAGCGGGCAGGCCTAACTCCACCAACTGTGGTGCGAGTCA
           147_3'_Border    (1) --------------------------------------------------
                               1401                                           1450
   Zp15 WT Genomic Locus  (970) --------------------------------------------------
      Zp15 donor fragment (1251) AGTATCTGAACTTGCCAGCATAGTCAGGAACAGCACGGTGCATGGTGCAC
           147_5'_Border  (1401) AGTATCTGAACTTGCCAGCATAGTCAGGAACAGCACGGTGCATGGTGCAC
           147_3'_Border    (1) --------------------------------------------------
                               1451                                           1500
   Zp15 WT Genomic Locus  (970) --------------------------------------------------
      Zp15 donor fragment (1301) AAGTTGTCCCAGACAAGGACTTGGTCTTCTTCCACCTCACACGGCAAGT
           147_5'_Border  (1451) AAGTTGTCCCAGACAAGGACTTGGTCTTCTTCCACCTCACACGGCAAGT
           147_3'_Border    (1) --------------------------------------------------
                               1501                                           1550
   Zp15 WT Genomic Locus  (970) --------------------------------------------------
      Zp15 donor fragment (1351) GAAGTCAAATCTGGTGGCATGCTCATAGAGGAACTGAAGCAATGGCTTTG
           147_5'_Border  (1501) GAAGTCAAATCTGGTGGCATGCTCATAGAGGAACTGAAGCAATGGCTTTG
           147_3'_Border    (1) --------------------------------------------------
                               1551                                           1600
   Zp15 WT Genomic Locus  (970) --------------------------------------------------
      Zp15 donor fragment (1401) ATTCTGCATCTGTCATGCCCTCAATTCTCTGACAGTAGACTTGATTCACA
           147_5'_Border  (1551) ATTCTGCATCTGTCATGCCCTCAATTCTCTGACAGTAGACTTGATTCACA
           147_3'_Border    (1) --------------------------------------------------
                               1601                                           1650
   Zp15 WT Genomic Locus  (970) --------------------------------------------------
      Zp15 donor fragment (1451) TAAAGGCCTTTCCTTCCAGAGCCAGGATGAGTCACAACCAAGGGATGGAC
           147_5'_Border  (1601) TAAAGGCCTTTCCTTCCAGAGCCAGGATGAGTCACAACCAAGGGATGGAC
           147_3'_Border    (1) --------------------------------------------------
                               1651                                           1700
   Zp15 WT Genomic Locus  (970) --------------------------------------------------
      Zp15 donor fragment (1501) TGTCTCTCTGTCACCAGCATCAACATCCATCACCTTGACTGAGGTGTTGC
           147_5'_Border  (1651) TGTCTCTCTGTCACCAGCATCAACATCCATCACCTTGACTGAGGTGTTGC
           147_3'_Border    (1) --------------------------------------------------
                               1701                                           1750
   Zp15 WT Genomic Locus  (970) --------------------------------------------------
      Zp15 donor fragment (1551) TGAAGCGACGGTTCTGTGCTTGGTAGAGGGAACCGAACACACGTGTGGCA
           147_5'_Border  (1701) TGAAGCGACGGTTCTGTGCTTGGTAGAGGGAACCGAACACACGTGTGGCA
           147_3'_Border    (1) --------------------------------------------------
                               1751                                           1800
   Zp15 WT Genomic Locus  (970) --------------------------------------------------
      Zp15 donor fragment (1601) GAGTGCACAACGTTGAGCCCTTCGATGGTGGCTTGCATGGTTGGAGACAA
           147_5'_Border  (1751) GAGTGCACAACGTTGAGCCCTTCGATGGTGGCTTGCATGGTTGGAGACAA
           147_3'_Border    (1) --------------------------------------------------
                               1801                                           1850
   Zp15 WT Genomic Locus  (970) --------------------------------------------------
      Zp15 donor fragment (1651) GGTCTCCCAAGCTGTGTACATTGAAAGGAACCCAGTGTCTCCGCCATGCT
           147_5'_Border  (1801) GGTCTCCCAAGCTGTGTACATTGAAAGGAACCCAGTGTCTCCGCCATGCT
           147_3'_Border    (1) --------------------------------------------------
                               1851                                           1900
   Zp15 WT Genomic Locus  (970) --------------------------------------------------
      Zp15 donor fragment (1701) CAGGAACATCTATGGCCCTCATCACAACAGCAGCTGGAGGTGCATCAAGG
           147_5'_Border  (1851) CAGGAACATCTATGGCCCTCATCACAACAGCAGCTGGAGGTGCATCAAGG
           147_3'_Border    (1) --------------------------------------------------
                               1901                                           1950
   Zp15 WT Genomic Locus  (970) --------------------------------------------------
      Zp15 donor fragment (1751) AAAGTGGAGTCTGTGTGCCAGTCATCACCAATCACCCTTCCAGACTCATT
           147_5'_Border  (1901) AAAGTGGAGTCTGTGTGCCAGTCATCACCAATCACCCTTCCAGACTCATT
           147_3'_Border    (1) --------------------------------------------------
                               1951                                           2000
   Zp15 WT Genomic Locus  (970) --------------------------------------------------
      Zp15 donor fragment (1801) GGCTTCTCTGCGGATCATCTGAACCTCTGGATAGCCTTCAATGCTCTTGA
           147_5'_Border  (1951) GGCTTCTCTGCGGATCATCTGAACCTCTGGATAGCCTTCAATGCTCTTGA
           147_3'_Border    (1) --------------------------------------------------
```

FIGURE 6D

```
                              2001                                              2050
Zp15 WT Genomic Locus   (970) --------------------------------------------------
   Zp15 donor fragment (1851) GAAGAGGCACTGGATCAACTGGTCCAAACCTTCTTGAGAATGCAATGTGC
          147_5'_Border (2001) GAAGAGGCACTGGATCAACTGGTCCAAACCTTCTTGAGAATGCAATGTGC
          147_3'_Border   (1) --------------------------------------------------
                              2051                                              2100
Zp15 WT Genomic Locus   (970) --------------------------------------------------
   Zp15 donor fragment (1901) TGCTCATTGGTGATTGCTTGGCCAGGAAAGTAGATGACTTGGTAAGTGTG
          147_5'_Border (2051) TGCTCATTGGTGATTGCTTGGCCAGGAAAGTAGATGACTTGGTAAGTGTG
          147_3'_Border   (1) --------------------------------------------------
                              2101                                              2150
Zp15 WT Genomic Locus   (970) --------------------------------------------------
   Zp15 donor fragment (1951) GAAGGCATCCAATATCTCATTCCAGGTGCTGTCATCAAGTGGTTCCCTCA
          147_5'_Border (2101) GAAGGCATCCAATATCTCATTCCAGGTGCTGTCATCAAGTGGTTCCCTCA
          147_3'_Border   (1) --------------------------------------------------
                              2151                                              2200
Zp15 WT Genomic Locus   (970) --------------------------------------------------
   Zp15 donor fragment (2001) AGTCCACGCCAGTGATCTCAGCACCAAGGACACCAGTGAGTGGCTGGACA
          147_5'_Border (2151) AGTCCACGCCAGTGATCTCAGCACCA------------------------
          147_3'_Border   (1) --------------------------------------------------
                              2201                                              2250
Zp15 WT Genomic Locus   (970) --------------------------------------------------
   Zp15 donor fragment (2051) GCTATTCTCTCAAAGCGTTGGGAGAGAGGGCTGAGGGCAGCATGAGCCAT
          147_5'_Border (2177) --------------------------------------------------
          147_3'_Border   (1) --------------------------------------------------
                              2251                                              2300
Zp15 WT Genomic Locus   (970) --------------------------------------------------
   Zp15 donor fragment (2101) GGTCTACCTACAAAAAAGCTCCGCACGAGGCTGCATTTGTCACAAATCAT
          147_5'_Border (2177) --------------------------------------------------
          147_3'_Border   (1) --------------------------------------------------
                              2301                                              2350
Zp15 WT Genomic Locus   (970) --------------------------------------------------
   Zp15 donor fragment (2151) GAAAAGAAAAACTACCGATGAACAATGCTGAGGGATTCAAATTCTACCCA
          147_5'_Border (2177) --------------------------------------------------
          147_3'_Border   (1) --------------------------------------------------
                              2351                                              2400
Zp15 WT Genomic Locus   (970) --------------------------------------------------
   Zp15 donor fragment (2201) CAAAAAGAAGAAAGAAAGATCTAGCACATCTAAGCCTGACGAAGCAGCAG
          147_5'_Border (2177) --------------------------------------------------
          147_3'_Border   (1) --------------------------------------------------
                              2401                                              2450
Zp15 WT Genomic Locus   (970) --------------------------------------------------
   Zp15 donor fragment (2251) AAATATATAAAAATATAAACCATAGTGCCCTTTTCCCCTCTTCCTGATCT
          147_5'_Border (2177) --------------------------------------------------
          147_3'_Border   (1) --------------------------------------------------
                              2451                                              2500
Zp15 WT Genomic Locus   (970) --------------------------------------------------
   Zp15 donor fragment (2301) TGTTTAGCATGGCGGAAATTTTAAACCCCCCATCATCTCCCCCAACAACG
          147_5'_Border (2177) --------------------------------------------------
          147_3'_Border   (1) --------------------------------------------------
                              2501                                              2550
Zp15 WT Genomic Locus   (970) --------------------------------------------------
   Zp15 donor fragment (2351) GCGGATCGCAGATCTACATCCGAGAGCCCCATTCCCCGCGAGATCCGGGC
          147_5'_Border (2177) --------------------------------------------------
          147_3'_Border   (1) --------------------------------------------------
                              2551                                              2600
Zp15 WT Genomic Locus   (970) --------------------------------------------------
   Zp15 donor fragment (2401) CGGATCCACGCCGGCGAGAGCCCCAGCCGCGAGATCCCGCCCCTCCCGCG
          147_5'_Border (2177) --------------------------------------------------
          147_3'_Border   (1) --------------------------------------------------
                              2601                                              2650
Zp15 WT Genomic Locus   (970) --------------------------------------------------
   Zp15 donor fragment (2451) CACCGATCTGGGCGCGCACGAAGCCGCCTCTCGCCCACCCAAACTACCAA
          147_5'_Border (2177) --------------------------------------------------
          147_3'_Border   (1) --------------------------------------------------
                              2651                                              2700
```

FIGURE 6E

```
Zp15 WT Genomic Locus    (970)  ----------------------------------------------------
Zp15 donor fragment     (2501) GGCCAAAGATCGAGACCGAGACGGAAAAAAAAAACGGAGAAAGGAAGAGG
       147_5'_Border    (2177) ----------------------------------------------------
       147_3'_Border       (1) ----------------------------------------------------
                              2701                                               2750

Zp15 WT Genomic Locus    (970)  ----------------------------------------------------
Zp15 donor fragment     (2551) AGAGGGGCGGGGTGGTTACCGGCGCGGCGGCGGCGGAGGGGGAGGGGGGA
       147_5'_Border    (2177) ----------------------------------------------------
       147_3'_Border       (1) ----------------------------------------------------
                              2751                                               2800

Zp15 WT Genomic Locus    (970)  ----------------------------------------------------
Zp15 donor fragment     (2601) GGCGTCGTCCGGCAGCGAGGGGGAGGAGGTGGAGGTGGTGGTGGTGGTG
       147_5'_Border    (2177) ----------------------------------------------------
       147_3'_Border       (1) ----------------------------------------------------
                              2801                                               2850

Zp15 WT Genomic Locus    (970)  ----------------------------------------------------
Zp15 donor fragment     (2651) GTGGTAGGGTTGGGGGGATGGGAGGAGAGGGGGGGGTATGTATATAGTGG
       147_5'_Border    (2177) ----------------------------------------------------
       147_3'_Border       (1) ----------------------------------------------------
                              2851                                               2900

Zp15 WT Genomic Locus    (970)  ----------------------------------------------------
Zp15 donor fragment     (2701) CGATGGGGGGCGTTTCTTTGGAAGCGGAGGGAGGGCCGGCCTCGTCGCTG
       147_5'_Border    (2177) ----------------------------------------------------
       147_3'_Border       (1) ----------------------------------------------------
                              2901                                               2950

Zp15 WT Genomic Locus    (970)  ----------------------------------------------------
Zp15 donor fragment     (2751) GCTCGCGATCCTCCTCGCGTTTCCGGCCCCCACGACCCGGACCCACCTGC
       147_5'_Border    (2177) ----------------------------------------------------
       147_3'_Border       (1) ----------------------------------------------------
                              2951                                               3000

Zp15 WT Genomic Locus    (970)  ----------------------------------------------------
Zp15 donor fragment     (2801) TGTTTTTTCTTTTTCTTTTTTTTCTTTCTTTTTTTTTTTTTTGGCTGCGA
       147_5'_Border    (2177) ----------------------------------------------------
       147_3'_Border       (1) -----------------------------------TTTTTTGGCTGCGA
                              3001                                               3050

Zp15 WT Genomic Locus    (970)  ----------------------------------------------------
Zp15 donor fragment     (2851) GACGTGCGGTGCGTGCGGACAACTCACGGTGATAGTGGGGGGG-TGTGGA
       147_5'_Border    (2177) ----------------------------------------------------
       147_3'_Border      (15) GACGTGCGGTGCGTGCGGACAACTCRCGGTGATAGTGGGGGGGGTGTGGA
                              3051                                               3100

Zp15 WT Genomic Locus    (970)  ----------------------------------------------------
Zp15 donor fragment     (2900) GACTATTGTCCAGTTGGCTGGACTGGGGTGGGTTGGGTTGGGTTGGGTTG
       147_5'_Border    (2177) ----------------------------------------------------
       147_3'_Border      (65) GACTATTGTCCAGTTGGCTGGACTGGGGTGGGTTGGGTTGGGTTGGGTTG
                              3101                                               3150

Zp15 WT Genomic Locus    (970)  ----------------------------------------------------
Zp15 donor fragment     (2950) GGCTGGGCTTGCTATGGATCGTGGATAGCACTTTGGGCTTTAGGAACTTT
       147_5'_Border    (2177) ----------------------------------------------------
       147_3'_Border     (115) GGCTGGGCTTGCTATGGATCGTGGATAGCACTTTGGGCTTTAGGAACTTT
                              3151                                               3200

Zp15 WT Genomic Locus    (970)  ----------------------------------------------------
Zp15 donor fragment     (3000) AGGGGTTGTTTTGTAAATGTTTTGAGTCTAAGTTTATCTTTTATTTTTA
       147_5'_Border    (2177) ----------------------------------------------------
       147_3'_Border     (165) AGGGGTTGTTTTGTAAATGTTTTGAGTCTAAGTTTATCTTTTATTTTTA
                              3201                                               3250

Zp15 WT Genomic Locus    (970)  ----------------------------------------------------
Zp15 donor fragment     (3050) CTAGAAAAAATACCCATGCGCTGCAACGGGGGAAAGCTATTTTAATCTTA
       147_5'_Border    (2177) ----------------------------------------------------
       147_3'_Border     (215) CTAGAAAAAATACCCATGCGCTGCAACGGGGGAAAGCTATTTTAATCTTA
                              3251                                               3300

Zp15 WT Genomic Locus    (970)  ----------------------------------------------------
Zp15 donor fragment     (3100) TTATTGTTCATTGTGAGAATTCGCCTGAATATATATTTTTCTCAAAAATT
       147_5'_Border    (2177) ----------------------------------------------------
       147_3'_Border     (265) TTATTGTTCATTGTGAGAATTCGCCTGAATATATATTTTTCTCAAAAATT
                              3301                                               3350

Zp15 WT Genomic Locus    (970)  ----------------------------------------------------
```

FIGURE 6F

```
Zp15 donor fragment  (3150) ATGTCAAATTAGCATATGGGTTTTTTTAAAGATATTTCTTATACAAATCC
       147_5'_Border (2177) --------------------------------------------------
       147_3'_Border  (315) ATGTCAAATTAGCATATGGGTTTTTTTAAAGATATTTCTTATACAAATCC
                            3351                                              3400
  Zp15 WT Genomic Locus (970) ------------------------------------------------
  Zp15 donor fragment  (3200) CTCTGTATTTACAAAAGCAAACGAACTTAAAACCCGACTCAAATACAGAT
       147_5'_Border (2177) --------------------------------------------------
       147_3'_Border  (365) CTCTGTATTTACAAAAGCAAACGAACTTAAAACCCGACTCAAATACAGAT
                            3401                                              3450
  Zp15 WT Genomic Locus (970) ------------------------------------------------
  Zp15 donor fragment  (3250) ATGCATTTCCAAAAGCGAATAAACTTAAAAACCAATTCATACAAAAATGA
       147_5'_Border (2177) --------------------------------------------------
       147_3'_Border  (415) ATGCATTTCCAAAAGCGAATAAACTTAAAAACCAATTCATACAAAAATGA
                            3451                                              3500
  Zp15 WT Genomic Locus (970) ------------------------------------------------
  Zp15 donor fragment  (3300) CGTATCAAAGTACCGACAAAAACATCCTCAATTTTTATAATAGTAGAAAA
       147_5'_Border (2177) --------------------------------------------------
       147_3'_Border  (465) CGTATCAAAGTACCGACAAAAACATCCTCAATTTTTATAATAGTAGAAAA
                            3501                                              3550
  Zp15 WT Genomic Locus (970) ------------------------------------------------
  Zp15 donor fragment  (3350) GAGTAAATTTCACTTTGGGCCACCTTTTATTACCGATATTTACTTTATA
       147_5'_Border (2177) --------------------------------------------------
       147_3'_Border  (515) GAGTAAATTTCACTTTGGGCCACCTTTTATTACCGATATTTACTTTATA
                            3551                                              3600
  Zp15 WT Genomic Locus (970) ------------------------------------------------
  Zp15 donor fragment  (3400) CCACCTTTTAACTGATGTTTTCACTTTTGACCAGGTAATCTTACCTTTGT
       147_5'_Border (2177) --------------------------------------------------
       147_3'_Border  (565) CCACCTTTTAACTGATGTTTTCACTTTTGACCAGGTAATCTTACCTTTGT
                            3601                                              3650
  Zp15 WT Genomic Locus (970) ------------------------------------------------
  Zp15 donor fragment  (3450) TTTATTTTGGACTATCCCGACTCTCTTCTCAAGCATATGAATGACCAATT
       147_5'_Border (2177) --------------------------------------------------
       147_3'_Border  (615) TTTATTTTGGACTATCCCGACTCTCTTCTCAAGCATATGAATGACCAATT
                            3651                                              3700
  Zp15 WT Genomic Locus  (970) GGTGTGGGCAGCCGAGCGCCATGTTCCAGCCGCTCCGGCAACAGTGCTGC
  Zp15 donor fragment   (3500) GGTGTGGGCAGCCGAGCGCCATGTTCCAGCCGCTCCGGCAACAGTGCTGC
       147_5'_Border   (2177) --------------------------------------------------
       147_3'_Border    (665) GGTGTGGGCAGCCGAGCGCCATGTTCCAGCCGCTCCGGCAACAGTGCTGC
                            3701                                              3750
  Zp15 WT Genomic Locus (1020) CAGCAGCAGATGAGGATGATGGACGTGCAGTCCGTCGCGCAGCAGCTGCA
  Zp15 donor fragment   (3550) CAGCAGCAGATGAGGATGATGGACGTGCAGTCCGTCGCGCAGCAGCTGCA
       147_5'_Border   (2177) --------------------------------------------------
       147_3'_Border    (715) CAGCAGCAGATGAGGATGATGGACGTGCAGTCCGTCGCGCAGCAGCTGCA
                            3751                                              3800
  Zp15 WT Genomic Locus (1070) GATGATGATGCAGCTTGAGCGTGCCGCTGCCGCCAGCAGCAGCCTGTACG
  Zp15 donor fragment   (3600) GATGATGATGCAGCTTGAGCGTGCCGCTGCCGCCAGCAGCAGCCTGTACG
       147_5'_Border   (2177) --------------------------------------------------
       147_3'_Border    (765) GATGATGATGCAGCTTGAGCGTGCCGCTGCCGCCAGCAGCAGCCTGTACG
                            3801                                              3850
  Zp15 WT Genomic Locus (1120) AGCCAGCTCTGATGCAGCAGCAGCAGCAGCTGCTGGCAGCCCAGGGTCTC
  Zp15 donor fragment   (3650) AGCCAGCTCTGATGCAGCAGCAGCAGCAGCTGCTGGCAGCCCAGGGTCTC
       147_5'_Border   (2177) --------------------------------------------------
       147_3'_Border    (815) AGCCAGCTCTGATGCAGCAGCAGCAGCAGCTGCTGGCAGCCCAGGGTCTC
                            3851                                              3900
  Zp15 WT Genomic Locus (1170) AACCCCATGGCCATGATGATGGCGCAGAACATGCCGGCCATGGGTGGACT
  Zp15 donor fragment   (3700) AACCCCATGGCCATGATGATGGCGCAGAACATGCCGGCCATGGGTGGACT
       147_5'_Border   (2177) --------------------------------------------------
       147_3'_Border    (865) AACCCCATGGCCATGATGATGGCGCAGAACATGCCGGCCATGGGTGGACT
                            3901                                              3950
  Zp15 WT Genomic Locus (1220) CTACCAGTACCAGCTGCCCAGCTACCGCACCAACCCCTGTGGCGTCTCCG
  Zp15 donor fragment   (3750) CTACCAGTACCAGCTGCCCAGCTACCGCACCAACCCCTGTGGCGTCTCCG
       147_5'_Border   (2177) --------------------------------------------------
       147_3'_Border    (915) CTACCAGTACCAGCTGCCCAGCTACCGCACCAACCCCTGTGGCGTCTCCG
                            3951                                              4000
  Zp15 WT Genomic Locus (1270) CTGCCATTCCGCCCTACTACTGATTCATGATATTTGGGAAATCTCCTCTA
  Zp15 donor fragment   (3800) CTGCCATTCCGCCCTACTACTGATTCATGATATTTGGGAAATCTCCTCTA
```

FIGURE 6G

```
        147_5'_Border  (2177) --------------------------------------------------
        147_3'_Border   (965) CTGCCATTCCGCCCTACTACTGATTCATGATATTGGGAAATCTCCTCTA
                              4001                                          4050
   Zp15 WT Genomic Locus (1320) TCCATCTCTCTCTATCTATATATGTAATAATGCAGTAAGACGACACACAT
     Zp15 donor fragment (3850) TCCATCTCTCTCTATCTATATATGTAATAATGCAGTAAGACGACACACAT
        147_5'_Border  (2177) --------------------------------------------------
        147_3'_Border  (1015) TCCATCTCTCTCTATCTATATATGTAATAATGCAGTAAGACGACACACAT
                              4051                                          4100
   Zp15 WT Genomic Locus (1370) TATCATGTGTGGTATGACCAATAATATATGCATGGTCATAATAAAGTTTT
     Zp15 donor fragment (3900) TATCATGTGTGGTATGACCAATAATATATGCATGGTCATAATAAAGTTTT
        147_5'_Border  (2177) --------------------------------------------------
        147_3'_Border  (1065) TATCATGTGTGGTATGACCAATAATATATGCATGGTCATAATAAAGTTTT
                              4101                                          4150
   Zp15 WT Genomic Locus (1420) GGTTTTAATGAATCTATCGGCCGCTTGATGTCTATGATGGACAAATCAAA
     Zp15 donor fragment (3950) GGTTTTAATGAATCTATCGGCCGCTTGATGTCTATGATGGACAAATCAAA
        147_5'_Border  (2177) --------------------------------------------------
        147_3'_Border  (1115) GGTTTTAATGAATCTATCGGCCGCTTGATGTCTATGATGGACAAATCAAA
                              4151                                          4200
   Zp15 WT Genomic Locus (1470) GCTTCTCCTGTCAGGCATGTAAATATTTCAAAATCTCTATTCAGGCTCAA
     Zp15 donor fragment (4000) ACTTCTCCTGTCAGGCATGTAAATATTTCAAAATCTCTATTCAGGCTCAA
        147_5'_Border  (2177) --------------------------------------------------
        147_3'_Border  (1165) ACTTCTCCTGTCAGGCATGTAAATATTTCAAAATCTCTATTCAGGCTCAA
                              4201                                          4250
   Zp15 WT Genomic Locus (1520) ATTCATAGCATATGGGTAGAGTAGTATGCTTGAGATTAGCAACTTTATAC
     Zp15 donor fragment (4050) ATTCATAGCATATGGGTAGAGTAGTATGCTTGAGATTAGCAACTTTATAC
        147_5'_Border  (2177) --------------------------------------------------
        147_3'_Border  (1215) ATTCATAGCATATGGGTAGAGTAGTATGCTTGAGATTAGCAACTTTATAC
                              4251                                          4300
   Zp15 WT Genomic Locus (1570) TTGAGTATAGAGTATAAAACATAAAGTCATGTGTATTCTATTGGCTAGAT
     Zp15 donor fragment (4100) TTGAGTATAGAGTATAAAACATAAAGTCATGTGTATTCTATTGGCTAGAT
        147_5'_Border  (2177) --------------------------------------------------
        147_3'_Border  (1265) TTGAGTATAGAGTATAAAACATAAAGTCATGTGTATTCTATTGGCTAGAT
                              4301                                          4350
   Zp15 WT Genomic Locus (1620) AAGTGTAAATGTGAGTTTAGAGGCAACAACCATGATTTGAATCCTAATTT
     Zp15 donor fragment (4150) AAGTGTAAATGTGAGTTTAGAGGCAACAACCATGATTTGAATCCTAATTT
        147_5'_Border  (2177) --------------------------------------------------
        147_3'_Border  (1315) AAGTGTAAATGTGAGTTTAGAGGCAACAACCATGATTTGAATCCTAATTT
                              4351                                          4400
   Zp15 WT Genomic Locus (1670) ACACATAATTTTAGCGTTTTTTCCATTTAAAGGCGGGGCTTGACGAAGTT
     Zp15 donor fragment (4200) ACACATAATTTTAGCGTTTTTTCCATTTAAAGGCGGGGCTTGACGAAGTT
        147_5'_Border  (2177) --------------------------------------------------
        147_3'_Border  (1365) ACACATAATTTTAGCGTTTTTTCCATTTAAAGGCGGGGCTTGACGAAGTT
                              4401                                          4450
   Zp15 WT Genomic Locus (1720) GGAAGCCGTGGAACTGCTGGGGCTTATCTTGACAACAAATCATTCCGGCA
     Zp15 donor fragment (4250) GGAAGCCGTGGAACTGCTGGGGCTTATCTTGACAACAAATCATTCCGGCA
        147_5'_Border  (2177) --------------------------------------------------
        147_3'_Border  (1415) GGAAGCCGTGGAACTGCTGGGGCTTATCTTGACAACAAATCATTCCGGCA
                              4451                                          4500
   Zp15 WT Genomic Locus (1770) GGGACATCATTCTTAATAGATACTGAGGCCAATCCCTTGAACTTATTCAG
     Zp15 donor fragment (4300) GAGACATCATTCTTAATAGATACTGAGGCCAATCCCTTGAACTTATTCAG
        147_5'_Border  (2177) --------------------------------------------------
        147_3'_Border  (1465) GAGACATCATTCTTAATAGATACTGAGGCCAATCCCTTGAACTTATTCAG
                              4501                                          4550
   Zp15 WT Genomic Locus (1820) GAGTAGTTTGATAACATTCTGTCACCCGAAAAGATTCTGTTAGATGGATG
     Zp15 donor fragment (4350) GAGTAGTTTGATAACATTCTGTCACCCGAAAAGATTCTGTTAGATGGATG
        147_5'_Border  (2177) --------------------------------------------------
        147_3'_Border  (1515) GAGTAGTTTGATAACATTCTGTCACCCGAAAAGATTCTGTTAGATGGATG
                              4551                                          4600
   Zp15 WT Genomic Locus (1870) CAGCAACTAGGATCTGGTGATAACTAGCCCGCTACCGGCGTGATTGGTT
     Zp15 donor fragment (4400) CAGCAACTAGGATCTGGTGATAACTAGCCCGCTACCGGCGTGATTGGTT
        147_5'_Border  (2177) --------------------------------------------------
        147_3'_Border  (1565) CAGCAACTAGGATCTGGTGATAACTAGCCCGCTACCGGCGTGATTGGTT
                              4601                                          4650
   Zp15 WT Genomic Locus (1920) GTGGTGCCAACGGGAGCCATGCTCACGCTGGCCTGGACGATCCGGGAAGC
     Zp15 donor fragment (4450) GTGGTGCCAACGGGAGCCATGCTCACGCTGGCCTGGACGATCCGGGAAGC
        147_5'_Border  (2177) --------------------------------------------------
```

FIGURE 6H

```
        147_3'_Border  (1615) GTGGTGCCAACGGGAGCCATGCTCACGCTGGCCTGGACGATCCGGGAAGC
                              4651                                            4700
 Zp15 WT Genomic Locus (1970) CTCTCACTAGCATCTCCACGCGTGCAGGCGGAGGGTTGAAAAAATGCTTG
    Zp15 donor fragment (4500) CTCTCACTAGCATCTCCACGCGTGCAGGCGGAGGGTTGAAAAAATGCTTG
        147_5'_Border  (2177) --------------------------------------------------
        147_3'_Border  (1665) CTCTCACTAGCATCTCCACGCGTGCAGGCGGAGGGTTGAAAAAATGCTTG
                              4701                                            4750
 Zp15 WT Genomic Locus (2020) GCCTGCTTCCGTGCATGCAGGCTACACCGGATAGTGCAGGTAACCAATC
    Zp15 donor fragment (4550) GCCTGCTTCCGTGCATGCAGGCTACACCGGATAGTGCAGGTAACCAATC
        147_5'_Border  (2177) --------------------------------------------------
        147_3'_Border  (1715) GCCTGCTTCCGTGCATGCAGGCTACACCGGATAGTGCAGGTAACCAATC
                              4751                                            4800
 Zp15 WT Genomic Locus (2070) GTATGCCCATTCACGGTCAATGCATACAACGAGCCTGAGTGTAGCTATCC
    Zp15 donor fragment (4600) GTATGCCCATTCACGGTCAATGCATACAACGAGCCTGAGTGTAGCTATCC
        147_5'_Border  (2177) --------------------------------------------------
        147_3'_Border  (1765) GTATGCCCATTCACGGTCAATGCATACAACGAGCCTGAGTGTAGCTATCC
                              4801                                            4850
 Zp15 WT Genomic Locus (2120) GAGCAACCAATCACGTGGTACCTGACCTAAGTAATGACCAGCAAATAAAA
    Zp15 donor fragment (4650) GAGCAACCAATCACGTGGTACCTGACCTAAGTAATGACCAGCAAATAAAA
        147_5'_Border  (2177) --------------------------------------------------
        147_3'_Border  (1815) GAGCAACCAATCACGTGGTACCTGACCTAAGTAATGACCAGCAAATAAAA
                              4851                                            4900
 Zp15 WT Genomic Locus (2170) GTGTTGAGCACCAAAATAGACAAGGTGGACGGTCCGCATCAGTATCGCGT
    Zp15 donor fragment (4700) GTGTTGAGCACCAAAATAGACAAGGTGGACGGTCCGCATCAGTATCG---
        147_5'_Border  (2177) --------------------------------------------------
        147_3'_Border  (1865) GTGTTGAGCACCAAAATAGACAAGGTGGACGGTCCGCATCAGTATCGCGT
                              4901                                            4950
 Zp15 WT Genomic Locus (2220) GCAGAGACAGTTAGGGTTCCGAGTTTCTTGTGACGGTTGTTAGCTAAATT
    Zp15 donor fragment (4747) --------------------------------------------------
        147_5'_Border  (2177) --------------------------------------------------
        147_3'_Border  (1915) GCAGAGACAGTTAGGGTTCCGAGTTTCTTGTGACGGTTGTTAGCTAAATT
                              4951                                            5000
 Zp15 WT Genomic Locus (2270) CGCGGAATTAACTCGGGAGATTGGTTGTAACGGGTCCAGACCCCTCCTC
    Zp15 donor fragment (4747) --------------------------------------------------
        147_5'_Border  (2177) --------------------------------------------------
        147_3'_Border  (1965) CGCGGAATTAACTCGGGAGATTGGTTGTAACGGGTCCAGACCCCTCCTC
                              5001                                            5050
 Zp15 WT Genomic Locus (2320) TATAAATATAAAGGAATACAGTTGATTGGGATAAACAATCGAACCTACAA
    Zp15 donor fragment (4747) --------------------------------------------------
        147_5'_Border  (2177) --------------------------------------------------
        147_3'_Border  (2015) TATAAATATAAAGGAATACAGTTGATTGGGATAAACAATCGAACCTACAA
                              5051                                            5100
 Zp15 WT Genomic Locus (2370) TCAATAAAATTGCATTTTATCTTGTACATTTAGGAGTCGCTCTAGTTTA
    Zp15 donor fragment (4747) --------------------------------------------------
        147_5'_Border  (2177) --------------------------------------------------
        147_3'_Border  (2065) TCAATAAAATTGCATTTTATCTTGTACATTTAGGAGTCGCTCTAGTTTA
                              5101                                            5150
 Zp15 WT Genomic Locus (2420) GTTCTAGTTTAACCTCTCAATCCCCAAATTCTCTGTTTCTCTTCGGCTCT
    Zp15 donor fragment (4747) --------------------------------------------------
        147_5'_Border  (2177) --------------------------------------------------
        147_3'_Border  (2115) GTTCTAGTTTAACCTCTCAATCCCCAAATTCTCTGTTTCTCTTCGGCTCT
                              5151                                            5200
 Zp15 WT Genomic Locus (2470) ACATCGATTATAGGTGTCTAGGTCGGCCTGCCGACTATAGACAAAGCATA
    Zp15 donor fragment (4747) --------------------------------------------------
        147_5'_Border  (2177) --------------------------------------------------
        147_3'_Border  (2165) ACATCGATTATAGGTGTC--------------------------------
                              5201
 Zp15 WT Genomic Locus (2520) GGACCT
    Zp15 donor fragment (4747) ------
        147_5'_Border  (2177) ------
        147_3'_Border  (2183) ------
```

TARGETED INTEGRATION INTO THE *ZP15* LOCUS

CROSS REFERENCE TO RELATED APPLICATIONS

The present application claims the benefit of U.S. Provisional Application No. 61/201,946, filed Dec. 17, 2008, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the field of plant genomic engineering, particularly targeted integration of a transgene into a plant Zp15 gene.

BACKGROUND

Biotechnology has emerged as an essential tool in efforts to meet the challenge of increasing global demand for food production. Conventional approaches to improving agricultural productivity, e.g. enhanced yield or engineered pest resistance, rely on either mutation breeding or introduction of novel genes into the genomes of crop species by transformation. Both processes are inherently nonspecific and relatively inefficient. For example, conventional plant transformation methods deliver exogenous DNA that integrates into the genome at random locations. Thus, in order to identify and isolate transgenic lines with desirable attributes, it is necessary to generate thousands of unique random-integration events and subsequently screen for the desired individuals. As a result, conventional plant trait engineering is a laborious, time-consuming, and unpredictable undertaking. Furthermore the random nature of these integrations makes it difficult to predict whether pleiotropic effects due to unintended genome disruption have occurred. As a result, the generation, isolation and characterization of plant lines with engineered genes or traits has been an extremely labor and cost-intensive process with a low probability of success.

Targeted gene modification overcomes the logistical challenges of conventional practices in plant systems, and as such has been a long-standing but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology J.* 6(1):93.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; and 20060188987, and International Publication WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. patent application Ser. No. 12/284,888 describes ZFN-mediated targeted integration into a plant EPSPS locus.

However, there remain needs for compositions and methods for stable targeted integration into additional loci within a plant genome for establishing stable, heritable genetic modifications in the plant and its progeny.

SUMMARY

The present disclosure provides methods and compositions for expressing one or more products of an exogenous nucleic acid sequence (i.e. a protein or a RNA molecule) that has been integrated into a Zp15 gene in a plant cell. As shown herein, the integration of one or more exogenous sequences at or near the Zp15 locus does not appear to impair the ability of the host plant to regenerate, flower or produce seed and, optionally, allows heritable transmission of the exogenous sequence(s) over generations. The exogenous nucleic acid sequences can comprise, for example, one or more genes or cDNA molecules, or any type of coding or noncoding sequence, as well as one or more control elements (e.g., promoters). For instance, herbicide tolerance genes can be integrated into this locus to produce crop plants with the desired herbicide resistance. Cells containing exogenous nucleic acids at or near the Zp15 locus can also contribute to the gametophyte (germline) and therefore be transmitted to progeny in subsequent generations.

Integration of the exogenous nucleic acid sequence into a Zp15 gene is facilitated by targeted double-strand cleavage of the genome in the selected Zp15 locus. Cleavage is targeted to a Zp15 gene through the use of fusion proteins comprising a DNA-binding domain, such as a meganuclease DNA-binding domain, a leucine zipper DNA-binding domain, a zinc finger protein (ZFP), or chimeric combinations of the aforementioned, which is engineered to bind a sequence within the selected Zp15 locus, and a cleavage domain or a cleavage half-domain. Such cleavage stimulates integration of exogenous polynucleotide sequences at or near the cleavage site. Integration of exogenous sequences can proceed through both homology-dependent and homology-independent mechanisms.

In one aspect, disclosed herein are engineered DNA-binding domains (e.g., ZFPs, meganucleases, or leucine zippers) that bind to a target site in a Zp15 gene. The DNA-binding domain can comprise, for example, any of the engineered zinc finger DNA binding domains comprising the recognition helices shown in Table 1. Any of the DNA-binding domains described herein may further comprise a functional domain, for example a cleavage domain or cleavage half-domain. In some embodiments, the cleavage half-domain can be from a Type IIS restriction endonuclease such as FokI or StsI. In other embodiments, the cleavage domain can comprise a homing endonuclease, for example a homing endonuclease with a modified DNA-binding domain.

In another aspect, disclosed herein are plants or seeds comprising an exogenous sequence integrated into the Zp15 locus. In certain embodiments, the exogenous sequence is integrated into the gametophyte of the plant.

In another aspect, disclosed herein is a method for expressing the product of an exogenous nucleic acid sequence in a cell, the method comprising: (a) expressing a first fusion protein in the cell, the first fusion protein comprising a first DNA-binding domain (e.g., a ZFP) and a first cleavage half-domain, wherein the DNA-binding domain has been engineered to bind to a first target site in a Zp15 gene of the genome of the cell; (b) expressing a second fusion protein in the cell, the second fusion protein comprising a second DNA-domain and a second cleavage half domain, wherein the second DNA-domain binds to a second target site in the Zp15 gene of the genome of the cell, wherein the second target site is different from the first target site; and (c) contacting the cell with a polynucleotide comprising an exogenous nucleic acid sequence and a first nucleotide sequence that is homologous to the first sequence in a Zp15 gene; wherein binding of the first fusion protein to the first target site, and binding of the second fusion protein to the second target site, positions the cleavage half-domains such that the genome of the cell is cleaved in the Zp15 gene, thereby resulting in integration of the exogenous sequence into the genome of the cell in the Zp15 gene and expression of the product of the exogenous sequence.

The exogenous nucleic acid sequence may comprise a sequence encoding one or more functional polypeptides (e.g., a cDNA), with or without one or more promoters and/or may produce one or more RNA sequences (e.g., via one or more shRNA expression cassettes), which impart desirable traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. Of course, any two or more exogenous nucleic acids of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. In certain embodiments, the nucleic acid sequence comprises a sequence encoding a herbicide resistance protein (e.g., the AAD-1 (aryloxyalkanoate dioxygenase) gene, the AAD-12 gene, or the phosphinothricin acetyl transferase (PAT) gene) and/or functional fragments thereof. Expression of the integrated sequence can be driven by a promoter operably linked to the integrated sequence. Alternatively, the integrated sequence is promoterless and transcription is driven by the endogenous Zp15 promoter.

In certain embodiments, the polynucleotide further comprises a second nucleotide sequence that is homologous to a second sequence in the Zp15 gene. The second nucleotide sequence may be identical to the second sequence in the Zp15 gene. Furthermore, in embodiments comprising first and second nucleotide sequences, the first nucleotide sequence may be identical to the first sequence in the Zp15 gene and the second nucleotide sequence may be homologous but non-identical to a second sequence in the Zp15 gene. In any of the methods described herein, the first and second nucleotide sequences flank the exogenous sequence. In certain embodiments, the polynucleotide is a plasmid. In other embodiments, the polynucleotide is a linear DNA molecule.

In another aspect, provided herein is a method for integrating an exogenous sequence into the Zp15 gene in the genome of a cell, the method comprising: (a) expressing a first fusion protein in the cell, the first fusion protein comprising a first DNA-binding domain (e.g., a ZFP) and a first cleavage half-domain, wherein the first DNA-binding domain has been engineered to bind to a first target site in the Zp15 locus in the genome of the cell; (b) expressing a second fusion protein in the cell, the second fusion protein comprising a second DNA-binding domain (e.g., a ZFP) and a second cleavage half domain, wherein the second DNA-binding domain binds to a second target site in the Zp15 locus in the genome of the cell, wherein the second target site is different from the first target site; and (c) contacting the cell with a polynucleotide comprising an exogenous nucleic acid sequence; wherein binding of the first fusion protein to the first target site, and binding of the second fusion protein to the second target site, positions the cleavage half-domains such that the genome of the cell is cleaved in the Zp15 locus, thereby resulting in homology dependent integration of the exogenous sequence into the genome of the cell within the Zp15 locus. In certain embodiments, an exogenous sequence encoding a functional polypeptide is inserted into the Zp15 gene.

In any of the methods described herein, the first and second cleavage half-domains can be from a Type IIS restriction endonuclease, for example, FokI or StsI. Furthermore, in any of the methods described herein, at least one of the fusion proteins can comprise an alteration in the amino acid sequence of the dimerization interface of the cleavage half-domain, for example such that obligate heterodimers of the cleavage half-domains are formed.

In any of the methods described herein, the plant cell can comprise a monocotyledonous or dicotyledonous plant cell. In certain embodiments, the plant cell is a crop plant, for example maize.

BRIEF DESCRIPTION OF THE DRAWINGS

FIG. 1 depicts exemplary sequence analysis results of Zp15 amplification products from maize Hill gDNA derived from cells subjected to transient expression of ZFN pair #25 (binding sites underlined) and reveals an 6 bp NHEJ insertion (bolded) at the expected cleavage site. Shown is the region of Zp15 extending from nucleotides 625 to 695 of SEQ ID NO:126 (SEQ ID NOs: 129 and 130).

FIG. 2 depicts exemplary sequence analysis results of Zp15 amplification products from maize Hill gDNA derived from cells subjected to transient expression of ZFN pair #24 (binding sites underlined) and reveals a 3 bp deletion at the expected cleavage site. Shown is the region of Zp15 extending from nucleotides 741 to 816 of SEQ ID NO:128 (SEQ ID NOs: 131 and 132).

FIG. 6, sheets A to H, depicts the alignment of a targeted integration (TI) event wherein the maize wild type (WT) (SEQ ID NO:133), Zp15 donor fragment (SEC) ID NO:134) as well as the 5' (SEQ ID NO:135) and 3' (SEQ ID NO:136) border regions adjoining the integrated donor sequences are aligned.

DETAILED DESCRIPTION

Figure 3:
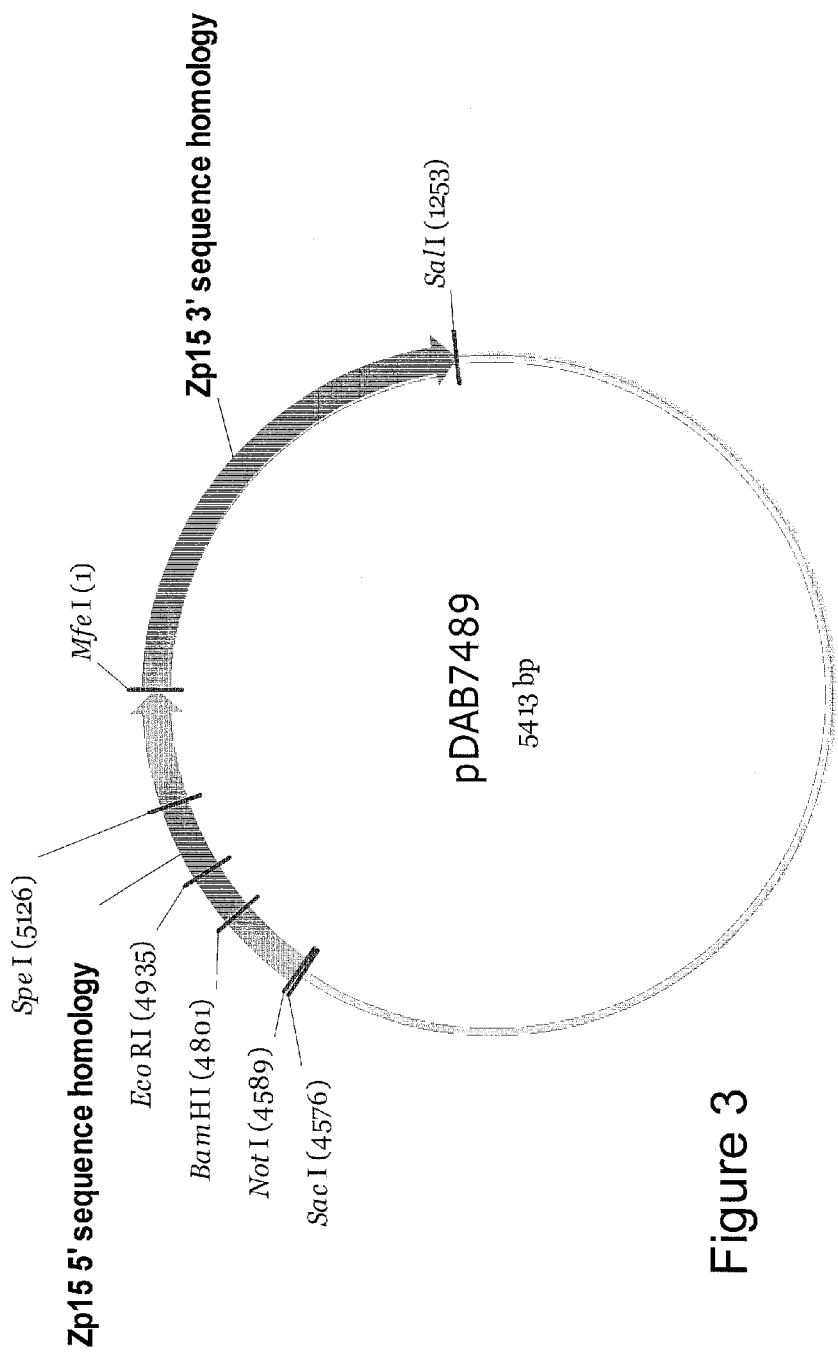
FIG. 3 is a schematic depicting the construct designated pDAB7489.

The present disclosure relates to methods and compositions for targeted integration (TI) into a plant Zp15 gene, which lies on chromosome 6 in maize. Using fusion proteins comprising DNA-binding domains (e.g., ZFPs, meganucleases, or leucine zippers) and nuclease domains, an inserted (donor) sequence can be operably linked to an exogenous promoter or can be promoterless. If promoterless, transcription of the integrated open reading frame can occur from the endogenous Zp15 gene promoter in the promoter-specified tissues. Use of a promoterless donor lowers the likelihood of random integration of the donor and/or the spurious activation of an endogenous gene by the promoter carried on the donor.

Compositions useful for targeted cleavage and recombination into a Zp15 gene include fusion proteins comprising a cleavage domain (or a cleavage half-domain) and a DNA-binding domain (e.g., a ZFP), polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any sequence within a Zp15 gene. The presence of such a fusion protein (or proteins) in a cell will result in binding of the fusion protein(s) to its (their) binding site(s) and cleavage within the endogenous Zp15 gene.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced, into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, nanoparticle transformation, DEAE-dextran-mediated transfer and viral vector-mediated transfer.

By contrast, an "endogenous" molecule is one that is normally present in a particular cell at a particular developmental stage under particular environmental conditions. For example, an endogenous, nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, for example, covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Target Sites

The disclosed methods and compositions include fusion proteins comprising a cleavage domain (or a cleavage half-domain) and a DNA-binding domain (e.g., ZFP, meganuclease or leucine zipper), in which the DNA-binding domain (e.g., zinc finger domain, meganuclease or leucine zipper), by binding to a sequence in a plant Zp15 locus directs the activity of the cleavage domain (or cleavage half-domain) to the vicinity of the sequence and, hence, induces cleavage (e.g., a double stranded break) in Zp15. As set forth elsewhere in this disclosure, a zinc finger domain can be engineered to bind to virtually any desired sequence. Accordingly, one or more DNA-binding domains (e.g., ZFPs) can be engineered to bind to one or more sequences in a plant Zp15 gene. Expression of a fusion protein comprising a DNA-binding domain (e.g., ZFP) and a cleavage domain (or of two fusion proteins, each comprising a DNA-binding domain and a cleavage half-domain), in a cell, effects cleavage in the Zp15 gene.

Selection of a sequence in a Zp15 for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

For ZFP DNA-binding domains, target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American Feb.:* 56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293 and also U.S. Patent Publication No. 20080182332 regarding non-canonical ZFPs for use in plants.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be desirable in some instances as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 configuration. A protein comprising three two-finger units (in each of which the two fingers are joined by a canonical linker), and in which each two-finger unit is joined to the adjacent two finger unit by a long linker, is referred to as a 3×2 configuration.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a "binding module." A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA binding domain is an engineered domain from a TAL effector derived from the plant pathogen *Xanthomonas* (see Boch et al, (2009) *Science* 29 Oct. 2009 (10.1126/science.117881) and Moscou and Bogdanove, (2009) *Science* 29 Oct. 2009 (10.1126/science.1178817).

Cleavage Domains

As noted above, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). Non limiting examples of homing endonucleases and meganucleases include I-SceI, I-CeuI, PI-PspI, PI-Sce, I-SceIV I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996)

J. Mol. Biol. 263:163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. See, e.g., U.S. Patent Publication Nos. 20050064474 and 20060188987; International Patent Publication WO 07/139, 898; Miller et al. (2007) Nat. Biotechnol. 25(7):778-785.

Additional engineered cleavage half-domains of FokI that form obligate heterodimers can also be used in the ZFNs described herein. In one embodiment, the first cleavage half-domain includes mutations at amino acid residues at positions 490 and 538 of FokI and the second cleavage half-domain includes mutations at amino acid residues 486 and 499.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains) and regulatory or cleavage domains (or cleavage half-domains), and polynucleotides encoding such fusion proteins, are described in co-owned U.S. Pat. Nos. 6,453,242 and 6,534,261 and U.S. Patent Application Publications 2007/0134796 and 2005/0064474; herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease comprises a fusion protein comprising a zinc finger binding domain and a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-FokI fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the FokI enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-FokI fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments of the disclosed fusion proteins, the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

In one embodiment, the disclosure provides a ZFN comprising a zinc finger protein having one or more of the recognition helix amino acid sequences shown in Table 1. In another embodiment, provided herein is a ZFP expression vector comprising a nucleotide sequence encoding a ZFP having one or more recognition helices shown in Table 1.

Targeted Integration

The disclosed methods and compositions can be used to cleave DNA in a Zp15 gene of plant cellular chromatin, which facilitates the stable, targeted integration of an exogenous sequence into the locus. As described herein, loss of function of endogenous Zp15 genes is well tolerated by plant cells and sequences integrated within this gene are broadly transcribed and generate plants with germline modifications for heritable transmission of the integrated sequence. Accordingly, Zp15 is a desirable site for targeted integration of exogenous sequences.

For targeted integration into Zp15, one or more DNA-binding domains (e.g., ZFPs) are engineered to bind a target site at or near the predetermined cleavage site, and a fusion protein comprising the engineered DNA-binding domain and a cleavage domain is expressed in a cell. Upon binding of the DNA-binding (e.g., zinc finger) portion of the fusion protein to the target site, the DNA is cleaved, preferably via a double-stranded break, near the target site by the cleavage domain.

The presence of a double-stranded break in the Zp15 locus facilitates integration of exogenous sequences via homologous recombination. Thus, the polynucleotide comprising the exogenous sequence to be inserted into the Zp15 gene will include one or more regions of homology with a Zp15 gene to facilitate homologous recombination.

Any sequence of interest (exogenous sequence) can be introduced into a Zp15 locus as described herein. Exemplary exogenous sequences include, but are not limited to any polypeptide coding sequence (e.g., cDNAs), promoter, enhancer and other regulatory sequences (e.g., interfering RNA sequences, shRNA expression cassettes, epitope tags, marker genes, cleavage enzyme recognition sites and various types of expression constructs. Such sequences can be readily obtained using standard molecular biological techniques (cloning, synthesis, etc.) and/or are commercially available.

In addition to the fusion molecules described herein, targeted replacement of a selected genomic sequence also involves the introduction of the replacement (or donor) sequence. The donor sequence can be introduced into the cell prior to, concurrently with, or subsequent to, expression of the fusion protein(s). The donor polynucleotide contains sufficient homology to Zp15 to support homologous recombination (or homology-directed repair) between it and the Zp15 genomic sequence to which it bears homology. Approximately 25, 50, 100, 200, 500, 750, 1,000, 1,500, 2,000 nucleotides or more of sequence homology between a donor and a genomic sequence (or any integral value between 10 and 2,000 nucleotides, or more) will support homologous recombination therebetween. In certain embodiments, the homology arms are less than 1,000 basepairs in length. In other embodiments, the homology arms are less than 750 basepairs in length. See, also, U.S. Provisional Patent Application No. 61/124,047, which is incorporated herein by reference.

Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to a gene sequence in the region of interest.

Donor molecules can also be inserted into the Zp15 locus to serve as a reservoir for later use. For example, a donor molecule homologous to an endogenous gene, but containing a mutation of interest may be inserted in the Zp15 locus. Next, ZFNs specific to the endogenous gene can be introduced which will cleave both the endogenous locus and the donor molecule in the Zp15 locus which contains the mutation of interest. The resulting DSB in the genome can then become the integration site for the donor molecule released from the Zp15 locus. In this way, the efficiency of targeted integration of a donor sequence at any region of interest can be greatly increased since the method does not rely on simultaneous uptake of both the nucleic acids encoding the ZFNs and those donor sequences.

Donor molecules can also be inserted into the Zp15 locus to serve as a target site for subsequent insertions. For example, a donor molecule comprised of DNA sequences that contain recognition sites for additional ZFN designs may be inserted into the Zp15 locus. Subsequently, additional ZFN designs may be generated and expressed in cells such that the original donor molecule is cleaved and modified by repair or homologous recombination. In this way, reiterative integrations of donor molecules may occur at the Zp15 locus.

To simplify assays (e.g., hybridization, PCR, restriction enzyme digestion) for determining successful insertion of the donor sequence, certain sequence differences may be present in the donor sequence as compared to the Zp15 genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the DNA-binding domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a nanoparticle, liposome or poloxamer, or can be delivered by bacteria or viruses (e.g., *Agrobacterium, Rhizobium* sp. NGR234, *Sinorhizoboium meliloti, Mesorhizobium loti*, tobacco mosaic virus, potato virus X, cauliflower mosaic virus and cassaya vein mosaic virus. See, e.g., Chung et al. (2006) *Trends Plant Sci.* 11(1):1-4.

It appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homology-directed repair, also known as "gene conversion." Applicants' methods advantageously combine the powerful targeting capabilities of engineered ZFPs with a cleavage domain (or cleavage half-domain) to specifically target paralogous genes such as Zp15 genes such that cleavage of the target sequence produces a double-stranded break in the region of the genome where insertion of exogenous sequences is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 1,000, 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, plant genes of the RAD54 epistasis group (e.g., AtRad54, AtRad51), and genes whose products interact with the aforementioned gene products. See, e.g., Klutstein M, et al. Genetics. 2008 April; 178 (4):2389-97.

Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) *EMBO* 21:2819-2826; Freisner et al. (2003) *Plant J.* 34:427-440; Chen et al. (1994) *European Journal of Biochemistry* 224:135-142. Methods for activation and repression of gene expression using fusions between a zinc finger binding domain and a functional domain are disclosed, for example, in co-owned U.S. Pat. Nos. 6,534,261; 6,824,978 and 6,933,113. Additional repression methods include the use of antisense oligonucleotides and/or small interfering RNA (siRNA or RNAi) or shRNAs targeted to the sequence of the gene to be repressed.

As an alternative to or, in addition to, activating expression of gene products involved in homologous recombination, fusions of these protein (or functional fragments thereof) with a zinc finger binding domain targeted to Zp15, can be used to recruit these proteins (recombination proteins) to the region of interest, thereby increasing their local concentration and further stimulating homologous recombination processes. Alternatively, a polypeptide involved in homologous recombination as described above (or a functional fragment thereof) can be part of a triple fusion protein comprising a zinc finger binding domain, a cleavage domain (or cleavage half-domain) and the recombination protein (or functional fragment thereof). Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases. See, also, Bhat et al. (1999) *Plant J.* 33:455-469.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitois (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Expression Vectors

A nucleic acid encoding one or more fusion proteins (e.g., ZFNs) as described herein can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a fusion protein can also be cloned into an expression vector, for administration to a plant cell.

To express the fusion proteins (e.g., ZFNs), sequences encoding the fusion proteins are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; $3^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive or an inducible promoter is used, depending on the particular use of the fusion protein. Non-limiting examples of plant promoters include promoter sequences derived from *A. thaliana* ubiquitin-3 (ubi-3) (Callis, et al., 1990, J. Biol. Chem. 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the fusion protein, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

The particular expression vector used to transport the genetic information into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, yeast or insect cell lines that express large quantities of protein, which can then be purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)).

Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable, of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., US Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-Agrobacterium bacteria or viruses such as *Rhizobium* sp. NGR234, *Sinorhizoboium meliloti, Mesorhizobium loti*, potato virus X, cauliflower mosaic virus and cassaya vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet.* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J.* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location (e.g. a Zp15 gene) in a plant cell genome. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Patent Publication No. 20090093366 which reference is hereby incorporated by reference in its entirety herein. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous target genes. It is known that plants may contain multiple paralogous genes. Thus, one or more different fusion proteins or expression vectors encoding fusion proteins may be administered to a plant in order to target one or more Zp15 genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

EXAMPLES

Below are examples of specific embodiments for carrying out the present disclosure. The examples are offered for illustrative purposes only, and are not intended to limit the scope of the present disclosure in any way.

Efforts have been made to ensure accuracy with respect to numbers used (e.g., amounts, temperatures, etc.), but some experimental error and deviation should, of course, be allowed for.

Example 1

Identification and Characterization of the Zp15 Target Locus

Based on publicly available genetic maps (Lawrence, C., et al. (2004) NAR 32:393-397; maize internet database) and the draft genome sequence of maize, the Zp15 locus on the short arm of chromosome 6 was chosen as a target for modification using ZFNs based on location and information available about the Zp15 gene. The genomic structure and sequence of a gene encoding 15 kD beta zein (Zp15) from maize has been described and annotated in the public domain (Woo et al. (2001) *Plant Cell* 13(10): 2297-2313). The sequence for the Zp15 gene is described in GenBank accession number AF371264, which is incorporated herein by reference.

The Zp15 genomic sequence was used to query the TIGR and Maize GDB genome databases using BLAST algorithms. Several sequences with overlapping homology to Zp15 including, but not limited to, two contigs, (AZM5_16782 and ZmGSStuc11-12-04.8785.1) and several ESTs (M72708, M13507, M12147, AY103640 and AF371264) were identified. Based on the sequence of these accessions as well as the Zp15 sequence, multiple short oligonucleotides were designed for use as PCR primers using the Primer3 program (Rozen, S, and Skaletsky, H. J. (2000) *Primer3 on the WWW for general users and for biologist programmers.* In: Krawetz S, Misener S (eds.) *Bioinformatics Methods and Protocols: Methods in Molecular Biology.* Humana Press, Totowa, N.J., pp 365-386; also available on the internet).

These primers include, but are not limited to, the following forward orientation oligonucleotides:

```
P67F  5'-CGTATGAATTCATTGACAACC-3'   (SEQ ID NO: 1)
P68F  5'-ATGATCTATCTGTAAATCC-3'     (SEQ ID NO: 2)
P69F  5'-CGTCATGCAACGCAACATTCC-3'   (SEQ ID NO: 3)
P73F  5'-AAGAACATCACAAGTTATGC-3'    (SEQ ID NO: 4)
P74F  5'-TCATGTGGATCCAAGGCATC-3'    (SEQ ID NO: 5)
```

In addition, the primers include, but are not limited to, the following reverse orientation oligonucleotides:

```
P70R  5'-ATGTGTGTCGTCTTACTGC-3'     (SEQ ID NO: 6)
P71R  5'-CAGTAGTAGGGCGGAATG-3'      (SEQ ID NO: 7)
P72R  5'-GGGCAGCTGGTACTG-3'         (SEQ ID NO: 8)
P75R  5'-CTATAATCGATGTAGAGC-3'      (SEQ ID NO: 9)
P76R  5'-CTATGCTTTGTCTATAGTCG-3'    (SEQ ID NO: 10)
```

All oligonucleotide primers were synthesized by and purchased from Integrated DNA Technologies (IDT, Coralville, Iowa). Amplifications of gDNA from maize variety Hi-II were performed on a PCR thermal cycler using 30 ng gDNA. A 2,215 bp amplification fragment corresponding to the Zp15 gene from Hi-II was isolated and cloned into the pCR2.1 plasmid (Invitrogen, Carlsbad, Calif.). Sequence analysis of this fragment revealed that the genomic structure of Zp15 from maize variety Hi-II contains two exons and one small intron of 31 bp (SEQ ID NO:126). Designs for Zp15-targeted ZFN were focused on the coding regions of the Zp15 gene from maize variety Hi-II.

Example 2

Design of Zinc Finger Nucleases Targeted to Maize Zp15 Gene

In order to assemble expression vectors for ZFNs, a stepwise modular cloning scheme was devised that is applicable for any given pair of ZFN-encoding genes selected from the library archive or synthesized de novo.

Zp15-targeted ZFNs were first screened using the yeast assay screen as described in Doyon et al. (2008) *Nature Biotechnology* 26(6):702 and U.S. patent application Ser. No. 12/284,887. Briefly, the entire Zp15 locus was introduced into the HO locus in the budding yeast genome in order to directly compare ZFN activity at different binding sites within the target gene; ZFNs were screened for their ability to induce a DSB in the reporter gene using a reporter assay (MEL1) as described in Doyon et al.

Based on the results of these proxy system assays, it was confirmed that various ZFN pairs tested were capable of inducing DSBs within Zp15.

Following yeast prescreening, the ZFN pairs were then subcloned into maize specific expression vectors. As described in U.S. Patent Publication No. 20080182332, a vector including redesigned and synthesized segments of a nuclear localization signal (NLS) derived from maize op-2 and a FokI nuclease domain utilizing the maize codon-bias was modified with a single nucleotide insertion (C) downstream of the unique Xho I site to create an extra Sac I site. A similar vector was modified to include the 2A ribosomal stuttering sequence from Thosea asigna virus. The gene cassettes encoding ORFs of individual zinc-finger proteins were cloned into either of these vectors via Kpn I and BamH I restriction sites, and subsequently the two vectors were combined via Bgl II/Xho I restriction sites, yielding an intermediate construct that contained a cassette including 2 ZFN-encoding domains flanked by Nco I and Sac I restriction sites.

The Nco I/Sac I cassette from this intermediate construction was excised via restriction enzyme digestion and ligated into the plasmid backbone pDAB3872, which contains a promoter from the maize ubiquitin-1 gene (Sharrock et al. (1992) *Plant Mol. Biol.* 18(4):675) and terminator sequences from maize root preferential cationic peroxidase gene (U.S. Pat. No. 7,179,902).

The resulting plasmids include the ZFN genes, plus the relevant selectable markers for plasmid maintenance and flanking attL sites for convenient manipulation using the GATEWAY™ system from Invitrogen (Carlsbad, Calif.). Each of the ZFN constructs generated using this cloning scheme were transformed into *E. coli* DH5α cells and subsequently maintained under the appropriate selection.

Table 1 shows exemplary Zp15-targeted ZFNs that were used for targeted integration experiments into the Zp15 locus. The DNA target sequence for the ZFN is shown in the second column (DNA target sites indicated in uppercase letters; non-contacted nucleotides indicated in lowercase), and the third through sixth columns show the amino acid sequence of the recognition region (amino acids −1 through +6, with respect to the start of the helix) of each of the zinc fingers (F1 through F4) in the protein. Also provided in the first column of Table 1 is an identification number for each protein.

TABLE 1

| ZNF name | Target Site | F1 | F2 | F3 | F4 |
|---|---|---|---|---|---|
| 11742 | cgGGGCTGCAGGGCttgt acggcgctgg (SEQ ID NO: 11) | DRSHLTR (SEQ ID NO: 12) | RSDNLRE (SEQ ID NO: 13) | RSDVLSE (SEQ ID NO: 14) | RSAHLSR (SEQ ID NO: 15) |
| 11743 | gcAGGGGCAGGGCAtctg cattgcagag (SEQ ID NO: 16) | QSGSLTR (SEQ ID NO: 17) | RSDHLTQ (SEQ ID NO: 18) | DRSHLTR (SEQ ID NO: 12) | RSDHLTQ (SEQ ID NO: 18) |
| 11750 | ctGAGGCAGCCGCAgtgc agccgctgg (SEQ ID NO: 19) | QSGDLTR (SEQ ID NO: 20) | DRSDLSR (SEQ ID NO: 21) | QSGDLTR (SEQ ID NO: 20) | RSDNLTR (SEQ ID NO: 22) |
| 11753 | acTCCGCGTAGGGGtaca gcccgccggc (SEQ ID NO: 23) | RSDHLSR (SEQ ID NO: 24) | RSDNLTT (SEQ ID NO: 25) | RSDDLTR (SEQ ID NO: 26) | DSSDRKK (SEQ ID NO: 27) |

TABLE 1-continued

| ZNF name | Target Site | F1 | F2 | F3 | F4 |
|---|---|---|---|---|---|
| 11754 | acTCCGCGTAGGGGtaca gcccgccggc (SEQ ID NO: 23) | RSDHLSE (SEQ ID NO: 29) | RNDNRKN (SEQ ID NO: 30) | RSDDLTR (SEQ ID NO: 26) | DSSDRKK (SEQ ID NO: 27) |
| 11755 | agCCGCAGtGCAGCCcgc tggcggcggc (SEQ ID NO: 31) | DRSDLSR (SEQ ID NO: 21) | QSSDLTR (SEQ ID NO: 32) | RSDHLSE (SEQ ID NO: 29) | TSSTRKT (SEQ ID NO: 33) |
| 11756 | agCCGCAGtGCAGCCcgc tggcggcggc (SEQ ID NO: 31) | DRSDLSR (SEQ ID NO: 21) | QSSDLTR (SEQ ID NO: 32) | RSDHLSE (SEQ ID NO: 29) | RSSTRKE (SEQ ID NO: 35) |
| 11757 | ccTCAGGTACTCCGcgta ggggtacagc (SEQ ID NO: 36) | RSDTLSE (SEQ ID NO: 37) | ARSTRTN (SEQ ID NO: 38) | QSSHLTR (SEQ ID NO: 39) | QSADRTK (SEQ ID NO: 40) |
| 11758 | gcCCGCTGGCGGCGgcgc cctactacgc (SEQ ID NO: 41) | RSDDLTR (SEQ ID NO: 26) | RSDDLTR (SEQ ID NO: 26) | RSDTLSA (SEQ ID NO: 42) | RNQDRKT (SEQ ID NO: 43) |
| 11759 | gcACTGCGGCTGCCtcag gtactccgcg (SEQ ID NO: 44) | DRSDLSR (SEQ ID NO: 21) | QSSDLRR (SEQ ID NO: 45) | RSDDLTR (SEQ ID NO: 26) | QSSDLTR (SEQ ID NO: 32) |
| 11760 | cgCCGGGTGTGGGCagcc gagcgccatg (SEQ ID NO: 47) | DRSHLSR (SEQ ID NO: 47) | RSDALAR (SEQ ID NO: 48) | QSSHLTR (SEQ ID NO: 39) | RSDDRKT (SEQ ID NO: 49) |
| 11761 | cgCCGGGTgTGGGCAgcc gagcgccatg (SEQ ID NO: 46) | QSGSLTR (SEQ ID NO: 17) | RSDHLTT (SEQ ID NO: 51) | QSSHLTR (SEQ ID NO: 39) | RSDDRKT (SEQ ID NO: 49) |
| 11762 | gcCGGGTGTGGGCAgccg agcgccatgt (SEQ ID NO: 52) | QSGSLTR (SEQ ID NO: 17) | RSDHLTT (SEQ ID NO: 51) | RSDSLLR (SEQ ID NO: 53) | RSDNLRE (SEQ ID NO: 13) |
| 11763 | agTAGGGCGCCGCCgcca gcgggctgca (SEQ ID NO: 54) | RSDNLTT (SEQ ID NO: 25) | DRSDLSR (SEQ ID NO: 21) | DRSHLTR (SEQ ID NO: 12) | RSDNLTT (SEQ ID NO: 25) |
| 11766 | tgTGGGCAGCCGAGcgcc atgttccagc (SEQ ID NO: 55) | RSDNLAR (SEQ ID NO: 56) | DRSDLSR (SEQ ID NO: 21) | QSGSLTR (SEQ ID NO: 17) | RSDHLTT (SEQ ID NO: 51) |
| 11767 | tgTGGGCAGCCGAGcgcc atgttccagc (SEQ ID NO: 55) | RSDNLSR (SEQ ID NO: 58) | DNSTRKT (SEQ ID NO: 59) | QSGSLTR (SEQ ID NO: 17) | RSDHLTT (SEQ ID NO: 51) |
| 11768 | cgGCGTAGTAGGGCgccg ccgccagcgg (SEQ ID NO: 60) | DRSHLTR (SEQ ID NO: 12) | RSDNLTT (SEQ ID NO: 25) | RSDNLST (SEQ ID NO: 61) | RSADLSR (SEQ ID NO: 62) |
| 11769 | cgGCGTAGtAGGGCGccg ccgccagcgg (SEQ ID NO: 60) | RSDDLTR (SEQ ID NO: 26) | RSDHLTQ (SEQ ID NO: 18) | RSDNLST (SEQ ID NO: 61) | RSADLSR (SEQ ID NO: 62) |
| 11770 | caGCCGCTCCGGCAacag tgctgccagc (SEQ ID NO: 64) | QSGSLTR (SEQ ID NO: 17) | RSDDRKT (SEQ ID NO: 49) | QSSDLSR (SEQ ID NO: 65) | DRSDLSR (SEQ ID NO: 21) |
| 11771 | acATGGCGcTCGGCTgcc cacacccggc (SEQ ID NO: 66) | QSSDLSR (SEQ ID NO: 65) | RNDDRKK (SEQ ID NO: 67) | RSDDLTR (SEQ ID NO: 26) | RSDALTQ (SEQ ID NO: 68) |
| 11772 | tgGCAGCCCAGGGTctca accccatggc (SEQ ID NO: 69) | QSSHLTR (SEQ ID NO: 39) | RSDNLRE (SEQ ID NO: 13) | DRSDLSR (SEQ ID NO: 21) | QSSDLTR (SEQ ID NO: 32) |
| 11773 | caGCTGCTGCTGCTgctg catcagagct (SEQ ID NO: 70) | QSSDLSR (SEQ ID NO: 65) | QSSDLRR (SEQ ID NO: 45) | QSSDLSR (SEQ ID NO: 65) | QSSDLRR (SEQ ID NO: 45) |

TABLE 1-continued

| ZNF name | Target Site | F1 | F2 | F3 | F4 |
|---|---|---|---|---|---|
| 11774 | ctGCCCAGCTACCGcacc aacccctgtg (SEQ ID NO: 28) | RSDSLSA (SEQ ID NO: 34) | DNSNRIK (SEQ ID NO: 50) | RSDNLSE (SEQ ID NO: 57) | ASKTRKN (SEQ ID NO: 63) |
| 11775 | tgGTACTGGTAGAGtcca cccatggccg (SEQ ID NO: 71) | RSDNLAR (SEQ ID NO: 56) | QSGSLTR (SEQ ID NO: 17) | RSDVLSE (SEQ ID NO: 14) | QSGSLTR (SEQ ID NO: 17) |
| 11776 | tgGTACTGGTAGAGtcca cccatggccg (SEQ ID NO: 71) | RSDNLAR (SEQ ID NO: 56) | QSGSLTR (SEQ ID NO: 17) | RSDALSN (SEQ ID NO: 72) | TSSARTT (SEQ ID NO: 73) |
| 11777 | aaCCCCTGtGGCGTCtcc gctgccattc (SEQ ID NO: 74) | DRSALSR (SEQ ID NO: 75) | DRSHLAR (SEQ ID NO: 76) | RSDTLSA (SEQ ID NO: 42) | DRSTRTT (SEQ ID NO: 77) |
| 11778 | gtGCGGTAGCTGGGcagc tggtactggt (SEQ ID NO: 78) | RSDHLSR (SEQ ID NO: 24) | QSSDLRR (SEQ ID NO: 45) | QSGALAR (SEQ ID NO: 79) | RSDDLTR (SEQ ID NO: 26) |
| 11779 | gtGCGGTAGCTGGGcagc tggtactggt (SEQ ID NO: 78) | RSDHLST (SEQ ID NO: 80) | HSDTRKK (SEQ ID NO: 81) | QSGALAR (SEQ ID NO: 79) | RSDDLTR (SEQ ID NO: 26) |
| 11780 | agGCGGGGcTTGACGaag ttggaagccg (SEQ ID NO: 82) | RSDSLSV (SEQ ID NO: 83) | QNQHRIN (SEQ ID NO: 84) | RSDHLSR (SEQ ID NO: 24) | RSDDLTR (SEQ ID NO: 26) |
| 11781 | aaATGGAAAAAACGctaa aattatgtgt (SEQ ID NO: 85) | RSDDLSK (SEQ ID NO: 86) | RNDHRKN (SEQ ID NO: 87) | QRSNLVR (SEQ ID NO: 88) | RSDALTQ (SEQ ID NO: 68) |
| 11782 | ttGTGGTGCCAACGggag ccatgctcac (SEQ ID NO: 89) | RSDTLSQ (SEQ ID NO: 90) | QNATRIN (SEQ ID NO: 91) | RSDALSR (SEQ ID NO: 92) | RSDALAR (SEQ ID NO: 48) |
| 11783 | ttGTGGTGCCAACGggag ccatgctcac (SEQ ID NO: 89) | RSDTLSQ (SEQ ID NO: 90) | QKATRIT (SEQ ID NO: 93) | RSDALSR (SEQ ID NO: 92) | RSDALAR (SEQ ID NO: 48) |
| 11784 | ttGTGGTGcCAACGGgag ccatgctcac (SEQ ID NO: 89) | RSDHLSE (SEQ ID NO: 29) | QNANRKT (SEQ ID NO: 94) | RSDALSR (SEQ ID NO: 92) | RSDALAR (SEQ ID NO: 48) |
| 11785 | caATCACGCCGGTAgcgg ggctagttat (SEQ ID NO: 95) | QSGALAR (SEQ ID NO: 79) | RSDDRKT (SEQ ID NO: 49) | RSDTLSQ (SEQ ID NO: 90) | DSSARKK (SEQ ID NO: 96) |

It will be apparent that ZFNs can be readily inserted into C2H2 or C3H backbones and that a variety of sequences can be used to join the zinc finger protein and the cleavage domain. See, U.S. Patent Publication 20080182332, particularly Table 6, regarding such sequences, which reference is hereby incorporated by reference in its entirety herein.

Example 3

ZFN-Mediated Disruption of Zp15 in Maize Cells

Induction of DSB by the ZFN pairs was tested. ZFN pairs that are capable of efficiently producing DSB at the intended target site of the endogenous Zp15 gene were identified. The error-prone nature of DSB repair by non-homologous end joining (NHEJ), which is known to generate small DNA deletions/insertions at the site of a ZFN-induced break, was utilized to select ZFN pairs which efficiently bound and cleaved the endogenous Zp15 gene target site ZFNs were transiently expressed in cultured maize cells and sequence analysis of the target locus at the predicted cleavage site was conducted. For example, a plasmid pDAB7468 encoding ZFN pair #25 (11768/11766 recognition helices shown above) was delivered via WHISKERS™—mediated transformation into maize Hi-II cell cultures as described in U.S. patent application Ser. No. 12/001,939, which is incorporated by reference in its entirety herein. After either 24 or 72 hours of transient expression, the resulting disrupted ZFN target sequence was amplified from isolated genomic DNA and cloned into plasmid vector pCR2.1. The gDNA was subjected to restriction digestion using enzyme Bsu36I, followed by amplification of the Zp15 target sequence and cloning of the PCR products into plasmid vector pCR2.1. Individual colonies of the cloned amplification product were analyzed by restriction digestions of plasmid DNA followed by agarose gel electrophoresis (cloned amplification products that displayed resistance to cleavage by restriction enzyme Bsu36I were considered to contain mutations that destroy the restriction site associated with the ZFN cleavage site).

Direct sequence analysis of 192 clones revealed a 6 bp insertion (FIG. 1). In another example, plasmid pDAB7467 encoding ZFN pair #24 (11753/11750 recognition helices shown above) was delivered directly into maize cell cultures and after either 24 or 72 hours of transient expression, the ZFN target sequence was amplified and cloned into plasmid vector pCR2.1. Direct sequence analysis of 192 clones revealed a 3 bp deletion (FIG. 2) at the precise cleavage site. The insertion and deletion described here are the outcome of NHEJ repair of an induced DSB at the target site and indicate that ZFNs 24 and 25 have cleavage activity at the endogenous Zp15 locus in maize cells.

The same process was performed using ZFN 25 or 28, but instead of screening colonies by restriction enzyme digestion, 192 independent clones were directly sequenced. A 6 bp insertion was detected (FIG. 2, top).

Taken together, these data demonstrate that a transient exposure to the ZFNs is sufficient to induce a targeted DSB at the Zp15 locus in cultured maize cells.

Example 4

Targeted Integration into Zp15 Locus

In order to test whether designed ZFNs with cleavage activity at Zp15 could drive integration of exogenous sequences, we constructed donor DNA molecules carrying an autonomous gene cassette encoding an exemplary exogenous herbicide resistance gene, AAD-1 from *Sphingomonas herbicidovorans* (ATCC 700291). AAD-1 encodes the enzyme aryloxyalkanoate dioxygenase and confers resistance to aryloxyphenoxypropionate herbicides (international patents WO 2005/107437, WO2008141154 A2). One of skill in the art will appreciate that other exogenous nucleic acids could be similarly incorporated into donor DNA molecules, including but not limited to other herbicide tolerance genes such as the related AAD-12 gene. In this herbicide tolerance gene donor, the promoter sequence is derived from *O. sativa* actin (GenBank accession numbers S44221 and X63830) and terminator sequences are derived from *Z. mays* L. lipase (GenBank Accession Number L35913).

A. Donor DNA Molecule Construction

Donor constructs containing regions of homology to Zp15 were generated as follows. A plasmid backbone containing homology flanks for the Zp15 gene was engineered to allow for the integration of any donor DNA sequence into the corresponding target site of the Zp15 gene. The plasmid backbone exemplified here originated with the base plasmid vector pBC SK(−) phagemid (3.4 kbp) (Stratagene, La Jolla, Calif.). There were four steps to this process.

First, the base plasmid was prepared by linearizing 3 μg pBC SK(−) using the Spe I and Sal I (New England Biolabs, Beverly, Mass.) restriction endonucleases. The 3.3 kbp SpeI/Sal I digested subcloning vector, pBC SK(−) was gel-excised and purified according to the manufacturer's directions using QIAQUICK Gel Extraction Kit (QIAGEN Inc., Valencia, Calif.).

Second, the 5′- & 3′-homology flanks were isolated from Zp15 using the following oligonucleotide primers that were synthesized by Integrated DNA Technologies, Inc. (Coralville, Iowa):

```
Zp15HRDonorNotI(205)F:
                                        (SEQ ID NO: 97)
5'-GCGGCCGCATGCAAGAGCTGTTGATC-3'

Zp15HRDonorMfeI(1025)R:
                                        (SEQ ID NO: 98)
5'-CAATTGCCGGCGTAGTAGGGCGCCGCCGCCAGC-3'
```

-continued
```
Zp15HRDonorMfeI(1025)F:
                                        (SEQ ID NO: 99)
5'-CAATTGGTGTGGGCAGCCGAGCGCCATGTTCCAG-3'

Zp15HRDonorSalI(2270)R:
                                        (SEQ ID NO: 100)
5'-GTCGACCGATACTGATGCGGACCGTCCACCTTGTC-3'.
```

PCR amplification reactions were carried out using reagents provided with the LA TAQ PCR kit (TaKaRa Biotechnology Inc. Otsu, Shiga, Japan). The PCR reaction cocktail consisted of: 5 uL 10×LA PCR™ Buffer II (Mg$^{2+}$), 20 ng double-stranded template (Hi-II maize genomic DNA), 10 pmol forward oligonucleotide primer, 10 pmol reverse oligonucleotide primer, 8 uL dNTP mix (2.5 mM each dNTP), 33.5 uL H$_2$O, 0.5 uL (2.5 units) TaKaRa LA Taq™ DNA polymerase, 1 drop of mineral oil. The primers Zp15HRDonorNotI(205)F and Zp15HRDonorMfeI(1025)R were used for a reaction and the primers Zp15HRDonorMfeI(1025)F and Zp15HRDonorSalI(2270)R were used for the second reaction. PCR reactions were performed using a Perkin-Elmer Cetus, 48-sample DNA thermal cycler (Norwalk, Conn.) under the following cycle conditions: 94° C., 4 min/1 cycle; 98° C. 20 sec, 65° C. 1 min, 68° C. 1 min/30 cycles; 72° C., 5 min/1 cycle; 4° C./hold. Fifteen (15) μl of each PCR reaction was electrophoresed and amplified fragments were visualized with UV light and fragment sizes estimated by comparison with 1 kbp DNA ladder. Expected plasmid clones were diagnosed by the presence of DNA fragments of 825 bp for the 5′-fragment or 1,250 bp for the 3′-fragment. These fragments were gel-excised and purified according to manufacturer's directions using QIAquick Gel Extraction Kit (QIAGEN Inc., Valencia, Calif.). Purified fragments were then cloned into pCR2.1 plasmid using TOPO TA CLONING® Kit and transformed into ONE SHOT® TOP10 Chemically competent *E. coli* cells (Invitrogen Life Technologies, Carlsbad, Calif.) according to manufacturer's protocol.

Individual colonies containing the 825 bp 5′-fragment or the 1,250 bp 3′-fragment were identified and confirmed via restriction enzyme digestion and sequencing data. Colonies containing the 825 bp 5′-fragment were confirmed via a restriction enzyme digestion of Mfe I and Not I (New England Biolabs, Beverly, Mass.). Colonies containing the 1,250 bp 3′-fragment were identified and confirmed via restriction enzyme digestion using Sal I (New England Biolabs, Beverly, Mass.). Expected plasmid clones were diagnosed by the presence of inserted DNA fragments of 825 bp (5′-fragment) or 1,250 bp (3′-fragment) in addition to the 3.9 kbp pCR®2.1 vector. Double-stranded sequencing reactions of plasmid clones were performed as described by manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using SEQUENCHER™ version 4.1.4 (Gene Codes Corporation, Arm Arbor, Mich.). The sequences of the 5′- and 3′-homology fragments from Zp15 are indicated in SEQ ID NO:127 and SEQ ID NO:128.

Third, the 3′-homology flank was ligated into the base plasmid as follows. Clones that contained the correct 3′-homology flank sequence were digested with restriction enzymes and a DNA fragment was gel-excised and purified using the QIAquick Gel Extraction Kit (QIAGEN Inc., Valencia, Calif.). These fragments were ligated into a purified base plasmid, previously digested with Spe I/Sal I (see above), at a 1:5 vector:insert ratio using 500 units T4 DNA Ligase (Invitrogen Life Technologies, Carlsbad, Calif.) in a reaction volume of 20 uL under conditions of 16 hr incubation in a 16° C. water bath. Five (5) uL of the ligation reaction was subsequently transformed into *E. coli* One SHOT® Top 10 Chemically Competent Cells, (Invitrogen Life Technologies, Carlsbad, Calif.) and plated onto media containing antibiotic selection. Putative colonies were isolated and digested with the Spe I and Sal I restriction enzymes (New England Biolabs, Beverly, Mass.) to identify clones which contained the ligated 3'-fragment.

Fourth, the 5'-homology flank was ligated into the plasmid containing the 3'-homology flank. The plasmid containing the 3'-homology flank, described above in step three, was digested with the Mfe I and Not I (New England Biolabs, Beverly, Mass.) restriction endonucleases for 1 hr at 37° C. The Not I/Mfe I digested the plasmid containing the 3'-homology flank was gel-excised and purified according to the manufacturer's directions using QIAquick Gel Extraction Kit (QIAGEN Inc., Valencia, Calif.).

Isolated fragments of the 5'-homology flank donor generated by restriction enzyme digestion using the Mfe I and Not I restriction enzymes were produced and ligated with the plasmid containing the 3'-homology flank in a 20 uL ligation reaction using a 1:5 vector:insert ratio and 500 units T4 DNA Ligase (Invitrogen Life Technologies, Carlsbad, Calif.). Ligation reactions were incubated for 16 hr in a 16° C. water bath.

Following the ligation, 5 uL of the ligation reaction was transformed into MAX EFFICIENCY® DH5α™ Chemically Competent Cells (Invitrogen Life Technologies, Carlsbad, Calif.) as per the manufacturer's recommendations. Individual colonies were selected and plasmid DNA was isolated and digested with the Not I restriction enzyme (New England Biolabs, Beverly, Mass.) to identify plasmids which contained an integrated fragment of the 5'-homology flank donor. The resulting plasmid was given the name pDAB7489 (FIG. 3).

Figure 4:
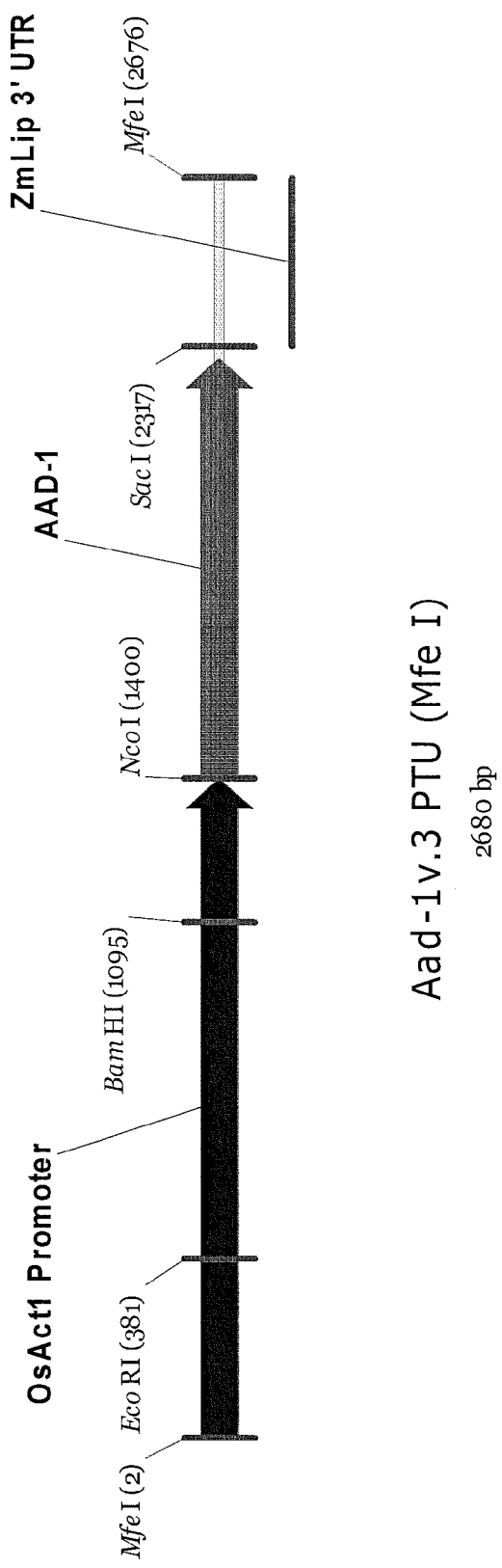
FIG. 4 is a schematic depicting an exemplary herbicide-tolerance gene expression cassette encoding an AAD gene.

An herbicide-tolerance gene expression cassette comprising a plant transcriptional unit (PTU) containing promoter, herbicide tolerance gene, and polyadenylation (polyA) termination sequences was constructed. The promoter sequence is derived from *O. sativa* actin 1 (McElroy et al. (1990) *Plant Cell* 2, 163-171; GenBank Accession S44221 and GenBank Accession X63830). The herbicide-tolerance gene comprised the AAD-1 (aryloxyalkanoate dioxygenase) gene, which confers resistance to aryloxyphenoxypropionate herbicides (WO 2005/107437). The version of the gene utilized was version #3, which includes a codon optimized sequence for expression in plants. The terminator sequences are derived from *Z. mays* L. lipase (maize lipase cDNA clone of GenBank Accession Number L35913). This maize sequence comprises the 3' untranslated region/transcription terminator region for the AAD-1 gene). The herbicide tolerance gene expression cassette is shown in FIG. 4.

To generate this cassette, the following oligonucleotide primers were synthesized by Integrated DNA Technologies, Inc. (Coralville, Iowa) under conditions of standard desalting and diluted with water to a concentration of 0.125 ug/uL:

OsActAad1v.3ZmLipMfeIF
(SEQ ID NO: 101)
5'-CAATTGGTCATTCATATGCTTGAGAAGA
G-3'

OsActAad1v.3ZmLipMfeIR
(SEQ ID NO: 102)
5'-CAATTGAGCACTTAAAGATCTTTAGAAG-3'

PCR amplification reactions were carried out using the LA TAQ PCR Kit (TaKaRa Biotechnology Inc., Otsu, Shiga Japan). The PCR reaction cocktail comprised: 5 uL 10×LA PCR™ Buffer II ($Mg^{2+}$), 20 ng double-stranded template (pDAB3878 plasmid DNA), 10 pmol forward oligonucleotide primer, 10 pmol reverse oligonucleotide primer, 8 uL dNTP mix (2.5 mM each), 33.5 uL $H_2O$, 0.5 uL (2.5 units) TaKaRa LA Taq™ DNA polymerase, 1 drop of mineral oil. PCR reactions were performed using a Perkin-Elmer Cetus, 48-sample DNA thermal cycler (Norwalk, Conn.) under the following cycle conditions 94° C., 4 min/1 cycle; 98° C. 20 sec, 55° C. 1 min, 68° C. 3 min/30 cycles; 72° C., 5 min/1 cycle; 4° C./hold. Fifteen (15) μl of each PCR reaction was electrophoresed at 100 V for 1 hr in a 1.0% TAE agarose gel supplemented with 0.5% ethidium bromide. Amplified fragments were visualized with UV light and fragment size estimated by comparison with 1 kbp DNA ladder.

Expected PCR products were diagnosed by the presence of a DNA fragment of 2.7 kbp (AAD-1 PTU). This fragment was gel-excised and purified according to manufacturer's directions using QIAquick Gel Extraction Kit (QIAGEN Inc., Valencia, Calif.). Purified fragments were then cloned into pCR2.1 plasmid using TOPO TA Cloning® Kit (with pCR®2.1 vector) and One Shot® TOP10 Chemically competent *E. coli* cells (Invitrogen Life Technologies, Carlsbad, Calif.) according to manufacturer's protocol.

Individual colonies were selected, plasmid DNA was isolated, and digested with the restriction enzyme Mfe I (New England Biolabs, Beverly, Mass.). Expected plasmid clones were diagnosed by the presence of an inserted DNA fragment of 2,674 bp (AAD-1 PTU) in addition to the 3.9 kbp pCR®2.1 vector. Double-stranded sequencing reactions of plasmid clones were performed as described by the manufacturer using CEQ™ DTCS-Quick Start Kit (Beckman-Coulter, Palo Alto, Calif.). Reactions were purified using Performa DTR Gel Filtration Cartridges (Edge BioSystems, Gaithersburg, Md.) as described by manufacturer protocols. Sequence reactions were analyzed on a Beckman-Coulter CEQ™ 2000 XL DNA Analysis System and nucleotide characterization performed using SEQUENCHER™ version 4:1.4 (Gene Codes Corporation, Ann Arbor, Mich.).

Restricted fragment from a clone that contained the correct 2,674 bp sequence was gel-excised and purified according to the manufacturer's directions using QIAquick Gel Extraction Kit (QIAGEN Inc., Valencia, Calif.). This fragment was then combined in a ligation reaction with purified pDAB7489 (plasmid backbone) which had been digested with restriction enzyme Mfe I and subsequently dephosphorylated. Ligation was carried out under the following conditions: 1:5 vector:insert ratio and 500 units T4 DNA Ligase (Invitrogen Life Technologies, Carlsbad, Calif.) in a reaction volume of 20 uL under conditions of 16 hr incubation in a 16° C. water bath. Five (5) uL of the ligation reaction was subsequently transformed into 50 μl *E. coli* MAX EFFICIENCY® DH5α™ Chemically Competent Cells, (Invitrogen Life Technologies, Carlsbad, Calif.) and plated under selection conditions described by the manufacturer.

Figure 5:
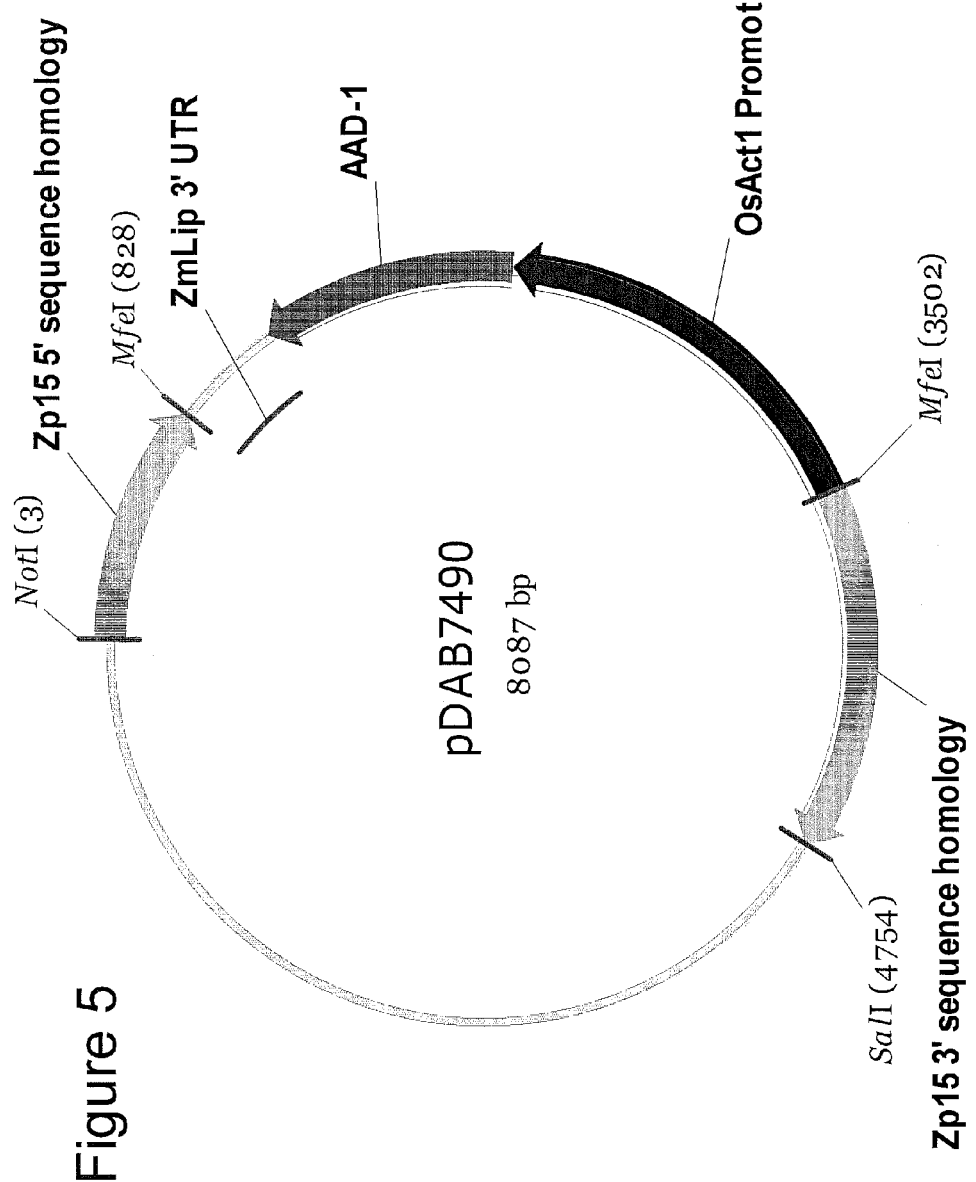
FIG. 5 is a schematic depicting the construct designated pDAB7490.

Individual colonies were selected, plasmid DNA was isolated, and digested with the restriction enzyme Mfe I (New England Biolabs, Beverly, Mass.). The expected plasmid clones contained DNA fragments 2,674 bp (AAD-1 PTU) and 5,413 bp (pDAB7489 vector). The resulting plasmid was named pDAB7490 (FIG. 5).

Embryogenic cell cultures of maize variety Hi-II (Armstrong et al. (1991) *Maize Genet Coop Newsletter* 65:92-93) were generated, maintained and subjected to simultaneous transformation of plasmids encoding ZFN24 and donor molecule pDAB7490. The transformation and selection of callus tissue and subsequent regeneration of transformants is described in U.S. patent application Ser. No. 12/001,939, which reference is hereby incorporated by reference in its entirety herein. For additional guidance regarding the transformation and selection protocol see Petolino et al. (2000) *Plant Cell Rept.* 19:781-786. Following anthesis, plants were either self-pollinated or outcrossed to maize variety DAS5XH751. Resulting progeny seed were harvested and dried. The regeneration of callus into intact, fertile maize plants is described in U.S. patent application Ser. No. 12/001, 939, particularly Example 22, which reference is hereby incorporated by reference in its entirety herein.

B. Targeted Integration of the AAD-1 Gene Cassette into the Zp15 Locus

Of the herbicide-tolerant events containing an integrated donor DNA molecule encoding an herbicide-tolerance gene cassette, it is expected that some proportion of said events are the product of targeted integration of donor DNA into the site of the ZFN-induced double-stranded break. In order to differentiate these targeted integration events from those derived from random integration of the herbicide-tolerance gene cassette, a PCR-based genotyping strategy using a combination of genome-specific and subsequent genome-specific plus donor-specific PCR primers was utilized.

Differential genotyping of targeted versus random-integration of the AAD-1 transgene in all herbicide-tolerant transformed events was carried out using PCR-based assays specific to the Zp15 locus and AAD-1 gene. In the examples presented here, all oligonucleotide primers were synthesized by Integrated DNA Technologies, Inc. (Coralville, Iowa) under conditions of standard desalting and diluted with water to a concentration of 100 µM. The following set of forward and reverse oligonucleotide primers were designed to anneal to gDNA sequences specific for the Zp15 gene target that lie outside the boundaries of the donor DNA sequences:

```
                                          (SEQ ID NO: 103)
HB501f:    5'-AAGGTCCCAAATCTGAGGCATACTGTTGCT-3'

(SEQ ID NO: 104)
HB502r:    5'-GAGGTCCTATGCTTTGTCTATAGTCGGCAG-3'
```

A second set of forward and reverse oligonucleotide primers were also designed to anneal to gDNA sequence specific for the Zp15 gene target outside the boundaries of the donor DNA sequences, yet nested within the first pair:

```
                                          (SEQ ID NO: 105)
HB503f    5'-GGCATACTGTTGCTGCCCTGCTGGAA-3'

(SEQ ID NO: 106)
HB504r    5'-GACACCTATAATCGATGTAGAGCCGAAGAG-3'
```

Forward and reverse oligonucleotide primers were additionally designed to anneal specifically to donor DNA corresponding to coding region of the AAD-1 herbicide-tolerance gene:

```
                                          (SEQ ID NO: 107)
HB505f    5'-AGTCCACCCCAGTGATCTCAGCACCA-3'

(SEQ ID NO: 108)
HB506f    5'-AGTGGCTGGACAGCTATTCTCTCAAAGCGT-3'

(SEQ ID NO: 109)
HB507r    5'-ACGCTTTGAGAGAATAGCTGTCCAGCCACT-3'

(SEQ ID NO: 110)
HB508r    5'-TGGTGCTGAGATCACTGGGGTGGACT-3'
```

Two distinct primary amplification reactions were carried out utilizing primers that bind in the Zp15 genomic region and the donor molecule, giving rise to an amplicon that spans the boundary of integration between genome and donor. The first reaction focused on the 5'-boundary between genome and donor and used primer set HB501f and HB507r. The second reaction focused on the 3'-boundary between donor and genome and used primer set HB505f and HB502r. Genomic DNA was isolated from the transformed maize Hi-II events. Primary PCR amplification reactions were carried out using reagents provided by the LA TAQ PCR Kit (TaKaRa Biotechnology Inc., Otsu, Shiga, Japan). The PCR reaction cocktail consisted of: 2.5 µl 10×La Taq PCR™ Buffer, 40-200 ng double-stranded genomic DNA template, 10 µM forward oligonucleotide primer, 10 µM reverse oligonucleotide primer, 2 µl dNTP mix (2.5 mM each), 16.25 µl H$_2$O, 0.25 µl (1.25 units) LA Taq™ DNA polymerase. PCR reactions were performed using a Bio-Rad, 96-sample DNA Engine Tetrad2, Peltier Thermal Cycler (Hercules, Calif.) under the following cycle conditions: 94° C., 2 min/1 cycle; 94° C. 30 sec, 62° C. 30 sec, 68° C. 5 min/30 cycles; 4° C./hold.

The primary PCR reaction products were subsequently diluted 1:100 in H$_2$O and used as template DNA for two distinct secondary PCR reactions. The secondary reactions also utilize primers that bind in the Zp15 genomic region and the donor molecule, giving rise to an amplicon that spans the boundary of integration between genome and donor. The identity of the specific primers determines whether the amplification is focused on either the 5'- or 3'-boundary between genome and donor. The first reaction focused on the 5'-boundary between genome and donor and used primer sets HB503 f and HB508r. The second reaction focused on the 3'-boundary between donor and genome and used primer set HB506f and HB504r. Both reactions consisted of the following: 2.5 µl 10×La Taq PCR™ Buffer, 1 µl template [1:50 dilution of 1° PCR reaction], 10 µM forward oligonucleotide primer, 10 µM reverse oligonucleotide primer, 2 µl dNTP mix (2.5 mM each), 16.25 µl H$_2$O, 0.25 µl (1.25 units) LA Taq™ DNA polymerase. PCR reactions were performed using a Bio-Rad, 96-sample DNA Engine Tetrad2, Peltier Thermal Cycler (Hercules, Calif.) under the following cycle conditions: 94° C., 2 min/1 cycle; 94° C. 30 sec, 62° C. 30 sec, 68° C. 5 min/30 cycles; 4° C./hold. Expected PCR amplicon fragments of 2,180 bp for the 5'-boundary or 2,980 bp for the 3'-boundary were observed.

These fragments were gel-excised and purified according to manufacturer's directions using QIAquick Gel Extraction Kit (QIAGEN Inc., Valencia, Calif.). Purified fragments were subsequently cloned into pCR2.1 plasmid using TOPO TA CLONING® Kit (with pCR®2.1 vector) and ONE SHOT® TOP10 Chemically competent *E. coli* cells (Invitrogen Life Technologies, Carlsbad, Calif.) according to manufacturer's protocol.

Individual colonies were selected, plasmid DNA was isolated and digested with the restriction enzyme Eco RI (New England Biolabs, Beverly, Mass.). Expected plasmid clones were diagnosed by the presence of inserted DNA fragments of the appropriate size in addition to the 3.9 kbp pCR82.1 vector.

Double-stranded sequencing reactions of plasmid clones were performed and nucleotide characterization and alignments were performed using SEQUENCER™ version 4.1.4 (Gene Codes Corporation, Ann Arbor, Mich.).

Selected sequence data derived from a targeted integration event (event #147) of the MD-1 donor gene cassette inserted into the Zp15 target gene is shown in the alignment of FIG. 6.

Primary PCR products amplification focused on either the 5'- or 3'-boundary between genome and donor were subjected to secondary amplification also focused on either the 5'- or 3'-boundary between genome and donor. Alignment of cloned fragments corresponding to these secondary amplification products with the wild-type Zp15 genomic sequence as well as the expected sequence of a targeted integration event clearly indicates that the precise integration of donor DNA at the target site has occurred. Nucleotide sequence of the Zp15 genomic locus, the genome/donor boundary, nucleotide sequence of the donor regions corresponding to Zp15 homology flanks and nucleotide sequence of the herbicide tolerance cassette were all preserved in multiple cloned PCR products derived from this event. Therefore, this event represents a genome in which homology-driven repair of a ZFN-mediated double-stranded break and targeted integration of a donor DNA at a specific gene target has occurred. In FIG. 6, we show sequence alignment data derived from a single representative isolated transformed maize callus (event #147).

Additional transformed events representing unique targeted integration occurrences have been obtained, demonstrating that the methods taught herein are reproducible in maize callus.

Example 5

Targeted Integration of PAT into Zp15 Locus

As a further exemplification of methods for targeted integration of selected exogenous polynucleotides into targeted loci disclosed herein, additional DNA donor molecules carrying an autonomous gene cassette encoding PAT were designed and constructed to test the integration of an exogenous donor sequence within the endogenous Zp15 target locus. ZFNs with specific cleavage activity of the endogenous Zp15 gene target were deployed to create a DSB at this locus. Donor DNA molecules carrying an autonomous gene cassette encoding PAT, from *Streptomyces viridochromogenes*, and flanking sequences homologous to Zp15 were subsequently integrated into the ZFN induced DSB of the Zp15 target. PAT encodes the enzyme phosphinothricin acetyl transferase and confers resistance to the herbicidal compound phosphinothricin (PPT) by acetylation (U.S. Pat. No. 5,633,434). Phosphinothricin is the active ingredient of the herbicide LIBERTY, BASTA and IGNITE. The PAT coding sequence was constructed as a plant transcription unit (PTU) and contained a promoter sequence derived from *O. sativa* actin (GenBank accession numbers S44221 and X63830) and a terminator sequences derived from *Z. mays* L. lipase (GenBank accession number L35913).

A. Donor DNA Molecule Construction

Figure 7:
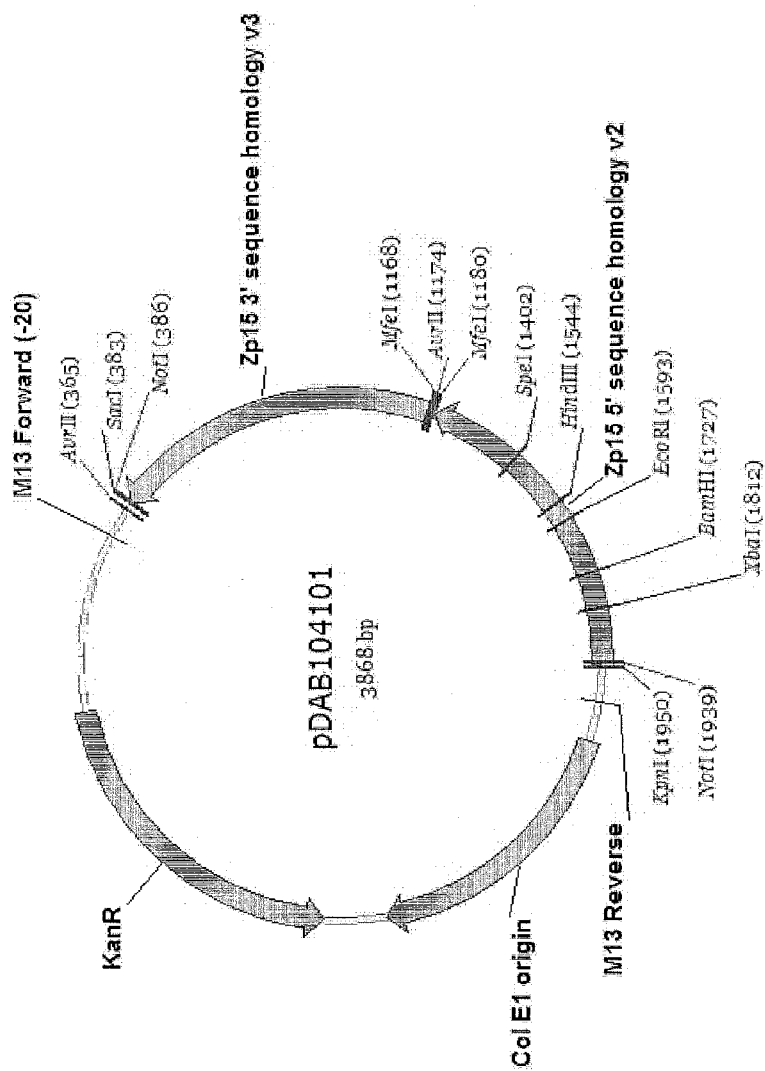
FIG. 7 is a schematic depicting the construct designated pDAB104101.

An Zp15 donor construct containing regions of homology to Zp15 was generated synthetically as follows. A Zp15 homology region comprising nucleotides 4595-5346 (5'-homology sequence; SEQ ID NO:111) and nucleotides 21-796 (3'-homology sequence; SEQ ID NO:112) from pDAB7489 was designed. This homology region included an Mfe I cloning sites between the 5' and 3'-homologous elements and Not I restriction sites at the 5' and 3' ends. This DNA sequence (SEQ ID NO:113) was synthesized and inserted into the kanamycin resistant ColE1 type plasmid, pMK at the Sac I and Kpn I cloning sites (Gene Art Ag, Regensburg, Germany). The resulting donor plasmid was designated pDAB104101 (FIG. 7) and contains homology flanks for the Zp15 gene to allow for the integration of any DNA sequence of interest into the corresponding target site of the Zp15 gene.

Figure 8:
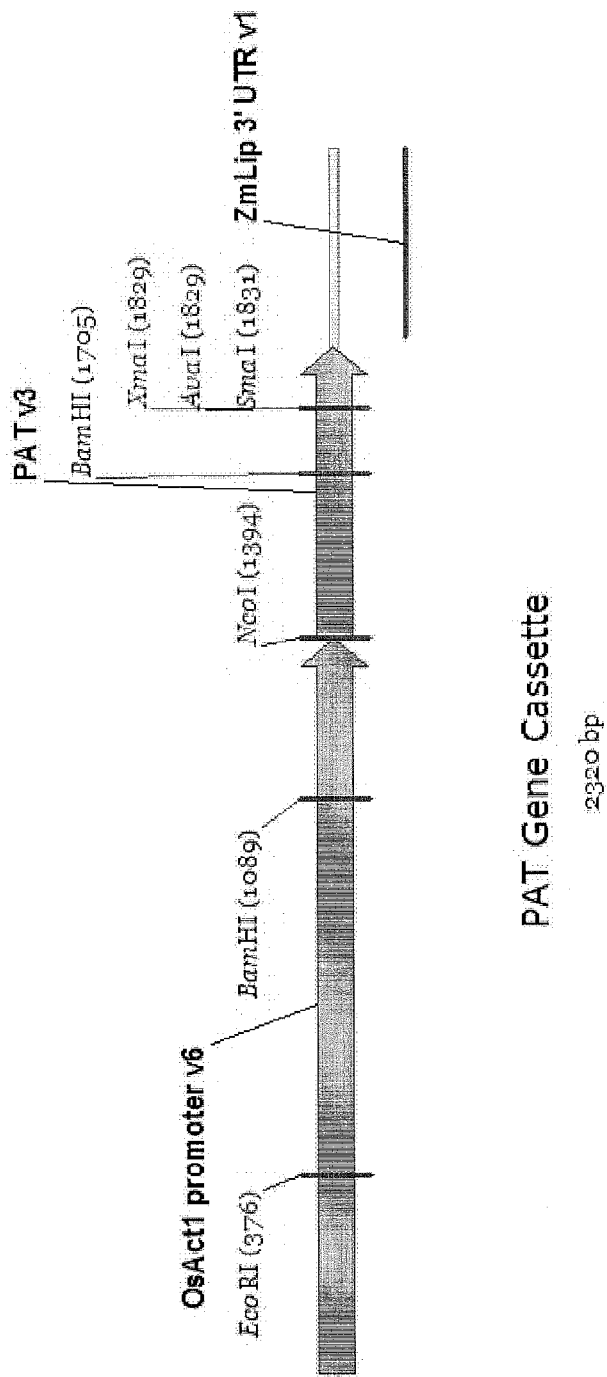
FIG. 8 is a schematic depicting the PAT expression cassette.

An herbicide-tolerance gene expression cassette comprising a complete PTU containing promoter, herbicide tolerance gene, and poly adenylation (polyA) termination sequences was constructed. The promoter sequence is derived from *O. sativa* actin 1 (McElroy et al. (1990) *Plant Cell* 2:163-171). GenBank Accession S44221 and GenBank Accession X63830). The herbicide-tolerance gene was PAT. The terminator sequences are derived from *Z. mays* L. lipase (maize lipase cDNA clone of GenBank Accession Number L35913). This maize sequence comprises the 3' untranslated region/transcription terminator region for the PAT gene. The PAT herbicide tolerance gene expression cassette is shown in FIG. 8.

The PAT gene cassette was amplified from a plasmid pDAB102256 by PCR using primers synthesized by Integrated DNA Technologies, Inc. (Coralville, Iowa):

```
                                          (SEQ ID NO: 114)
DC001  5'-CCAGTGCAATTGGGTCATTCATATGCTTGAGAAG-3'

(SEQ ID NO: 115)
DC002  5'-CCAGTGCAATTGAATTCAGCACTTAAAGATCTTTAG-3'
```

PCR amplification reactions were carried out using PHUSION™ DNA Polymerase (New England Biolabs, Beverly, Mass.) under the following cycle conditions: 98° C., 30 sec/1 cycle; 98° C. 10 sec, 60° C. 20 sec, 72° C. 45 sec/9 cycles; 98° C. 10 sec, 72° C. 60 sec/24 cycles; 72° C., 10 min/1 cycle; 4° C./hold. The PCR reaction was analyzed by electrophoresis in a 1.0% TAE agarose gel.

Expected PCR products were diagnosed by the presence of a DNA fragment of 2.3 kbp (PAT PTU). This fragment was excised and purified from the gel according to manufacturer's directions using QIAQUICK™ Gel Extraction Kit (QIAGEN Inc., Valencia, Calif.). Purified fragments were then cloned into pCR-Blunt II-TOPO vector using the Zero Blunt TOPO PCR Cloning Kit and ONE SHOT® TOP10 Chemically competent *E. coli* cells (Invitrogen Life Technologies, Carlsbad, Calif.)

Figure 9:
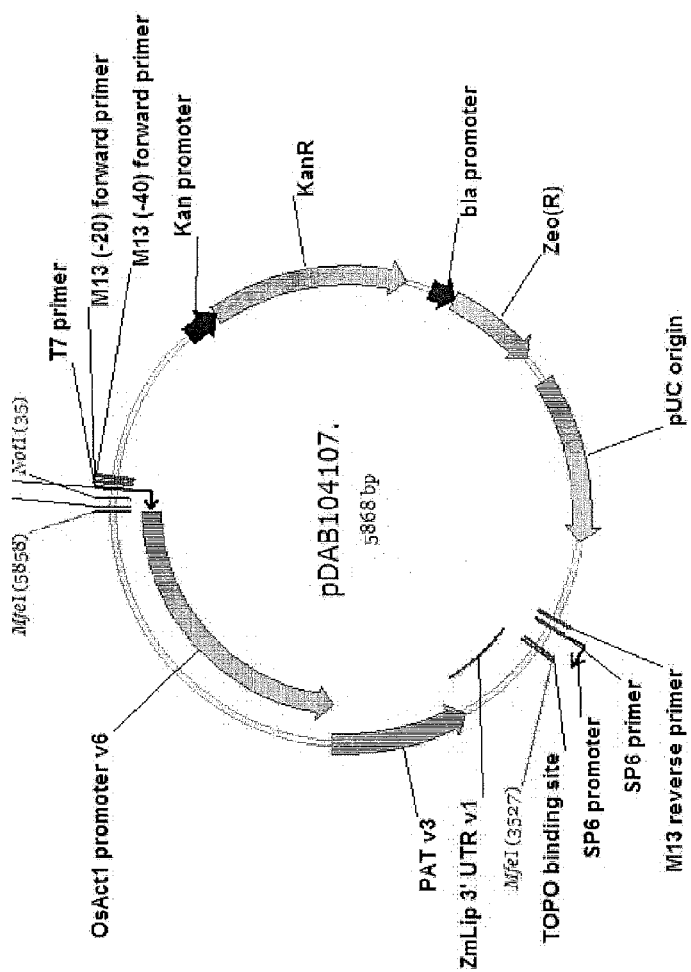
FIG. 9 is a schematic depicting the construct designated pDAB104107.

Individual colonies were picked and plasmid DNA was isolated and subjected to plasmid DNA restriction enzyme digestion and sequence analysis. The cloned PAT inserts were sequenced to demonstrate the identity and sequence fidelity of the cloned PCR products (SEQ ID NO:116). One such plasmid clone was designated pDAB104107 (FIG. 9) and was subsequently used as the source of the PAT gene cassette for insertion into the new Zp15 homology donor vectors.

Figure 10:
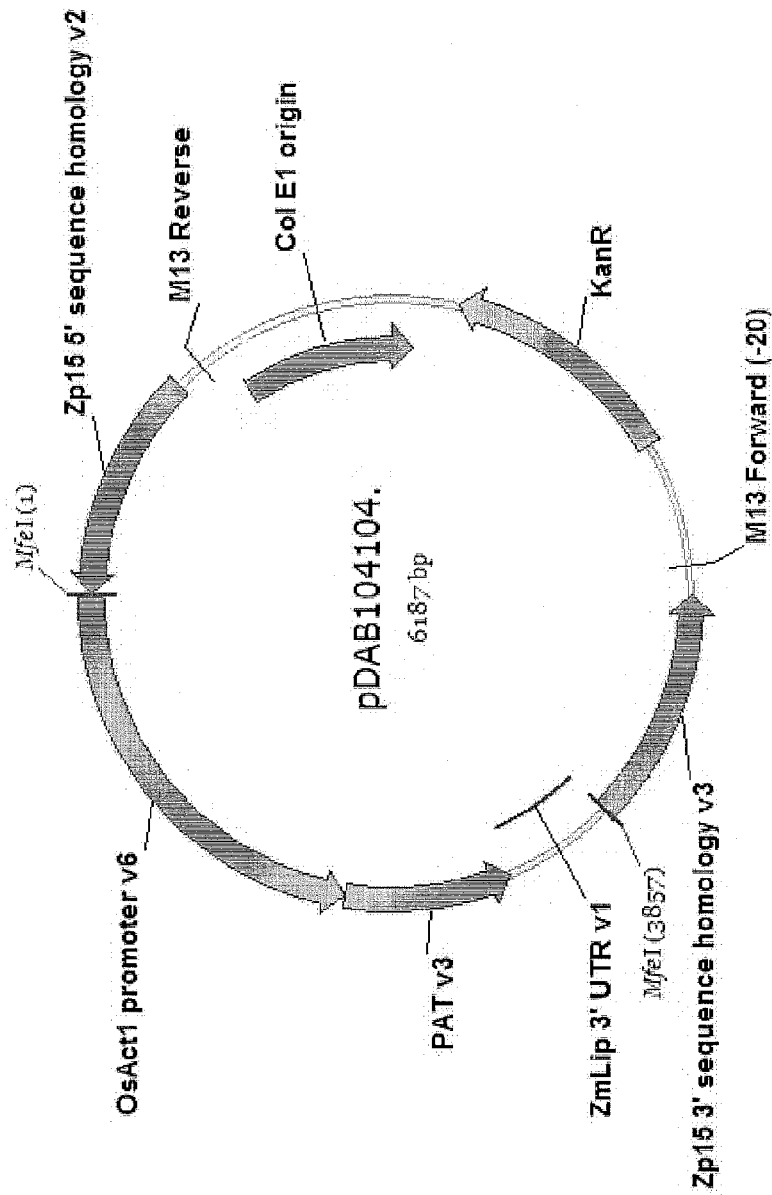
FIG. 10 is a schematic depicting the construct designated pDAB104104.
Figure 11:
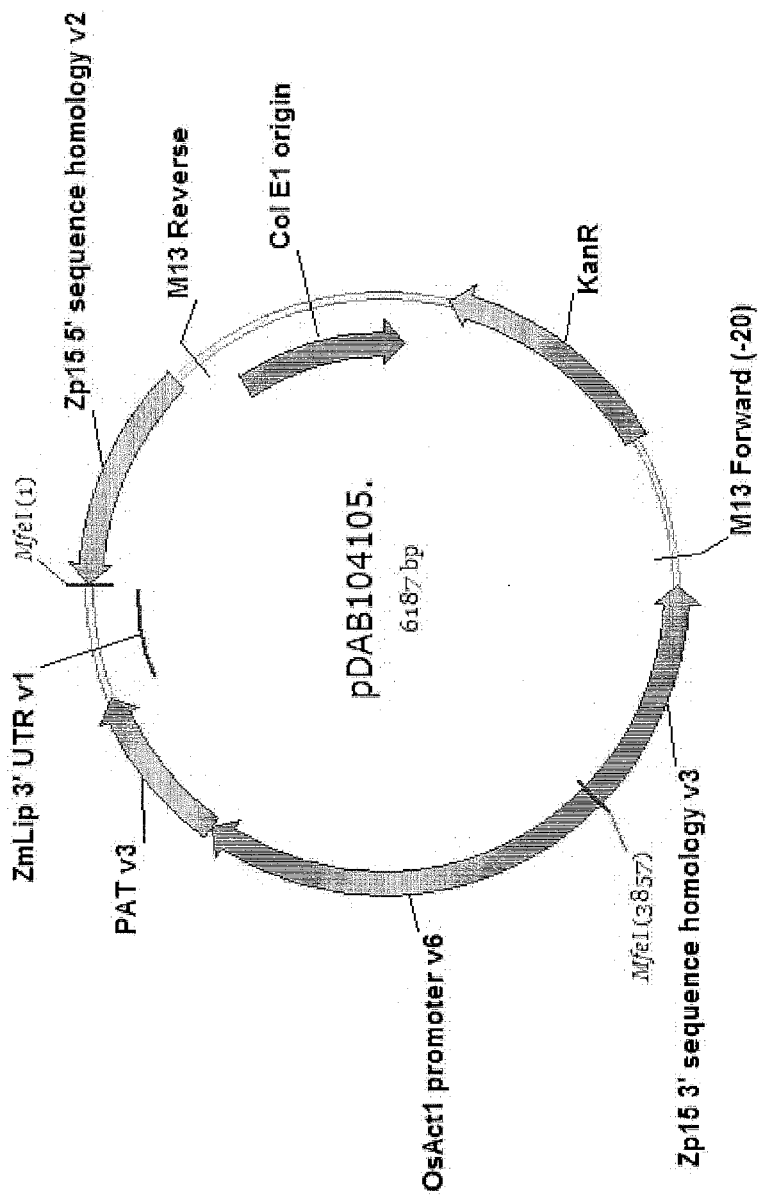
FIG. 11 is a schematic depicting the construct designated pDAB104105.

The 2.3 kbp PAT gene fragment was recovered from pDAB104107 by digestion with Mfe I followed by gel electrophoresis, excision and purification. The Zp15 homology donor plasmid pDAB104101 was also digested with Mfe I and gel purified. Ligation of the PAT gene fragment into pDAB104101 yielded clones in which the PAT gene was inserted at the Mfe I site in either of two orientations with respect to the Zp15 gene sequences as determined by differential restriction enzyme digestion. pDAB104104 (FIG. 10) comprised the PAT gene inserted in the same transcriptional orientation as the Zp15 gene. pDAB104105 (FIG. 11) comprised the PAT gene inserted in the opposite orientation relative to the Zp15 gene.

B. Additional Donor DNA Molecule Construction

Another donor construct containing regions of homology to Zp15 was generated in which the Zp15 3'-homology sequence in pDAB7489 was altered by truncation while the Zp15 5'-homology sequence in pDAB7489 remained the same. The truncated 3' homology region was generated from pDAB7489 by PCR using primers synthesized by Integrated DNA Technologies, Inc. (Coralville, Iowa):

```
                                         (SEQ ID NO: 117)
DC003   5'-CTAATCGTCGACTCGTCAAGCCCCGCCTTTAAAT-3'

(SEQ ID NO: 118)
DC004   5'-CTAATCCAATTGGTGTGGGCAGCCGAGCG-3'
```

PCR amplification reactions were carried out using PHUSION HOT START DNA Polymerase (New England Biolabs, Beverly, Mass.) under the following cycle conditions: 98° C., 30 s/1 cycle; 98° C. 10 sec, 72° C. 15 sec/33 cycles; 72° C., 5 min/1 cycle; 4° C./hold. The PCR reaction was subjected to electrophoresis in a 1.0% TAE agarose gel.

Expected PCR products were diagnosed by the presence of a DNA fragment of 0.8 kbp (Zp15 3'-homology). This fragment was gel-excised and purified according to manufacturer's directions using QIAquick Gel Extraction Kit (QIAGEN Inc., Valencia, Calif.). Purified fragments were then cloned into pCR-Blunt II-TOPO vector using the Zero Blunt TOPO PCR Cloning Kit and One Shot® TOP10 Chemically competent E. coli cells (Invitrogen Life Technologies, Carlsbad, Calif.) according to manufacturer's protocol.

Figure 12:
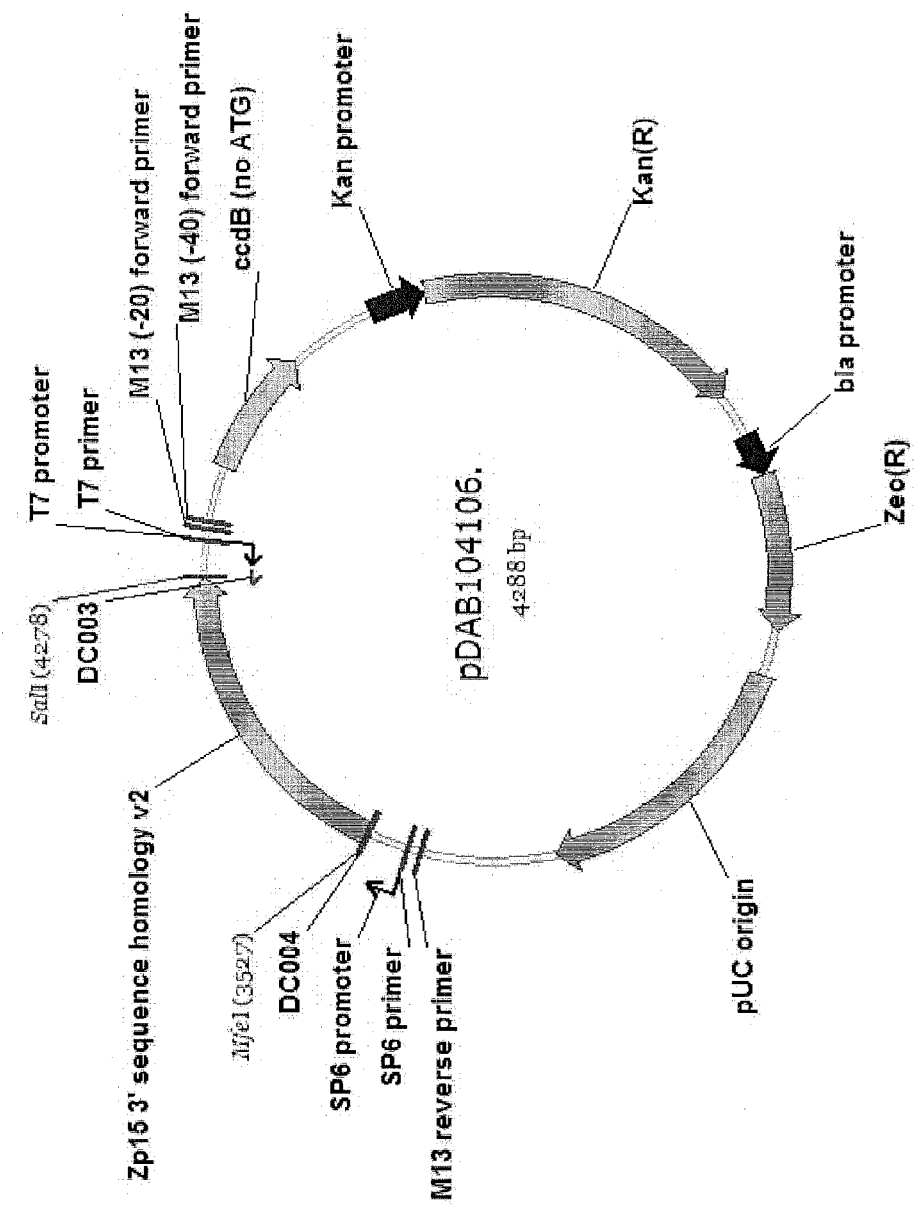
FIG. 12 is a schematic depicting the construct designated pDAB104106.
Figure 13:
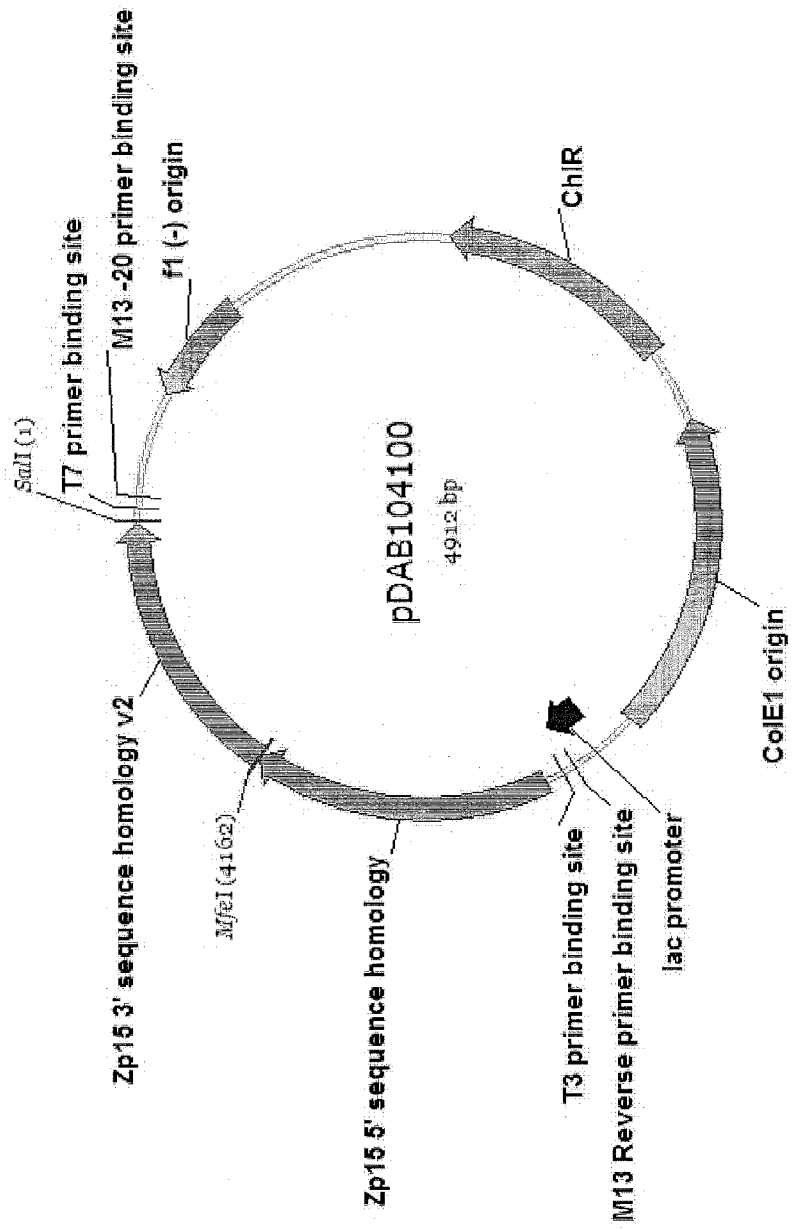
FIG. 13 is a schematic depicting the construct designated pDAB 104100.

Individual colonies were picked and subjected to plasmid DNA isolation and restriction enzyme digestion confirmation. Zp15 3' homology inserts were sequenced to demonstrate the identity and sequence fidelity of the cloned PCR products (SEQ ID NO:119). One such plasmid clone was designated pDAB104106 (FIG. 12) and was subsequently used as the source of the new Zp15 3' homology sequence for substitution into pDAB7489 to create a new Zp15 homology donor vector.

pDAB7489 was digested sequentially with Mfe I and Sal I and the 4.2 kbp vector fragment was gel purified. pDAB104106 was also digested with Mfe I and Sal I and the 0.8 kbp fragment comprising the truncated Zp15 3' homology sequence was gel purified. Ligation and transformation of these gel purified fragments yielded clones in which the truncated Zp15 3' homology sequence was substituted for the original Zp15 3' homology sequence. This plasmid was designated pDAB104100 (FIG. 13) and was used as the recipient for the PAT gene.

Figure 14:
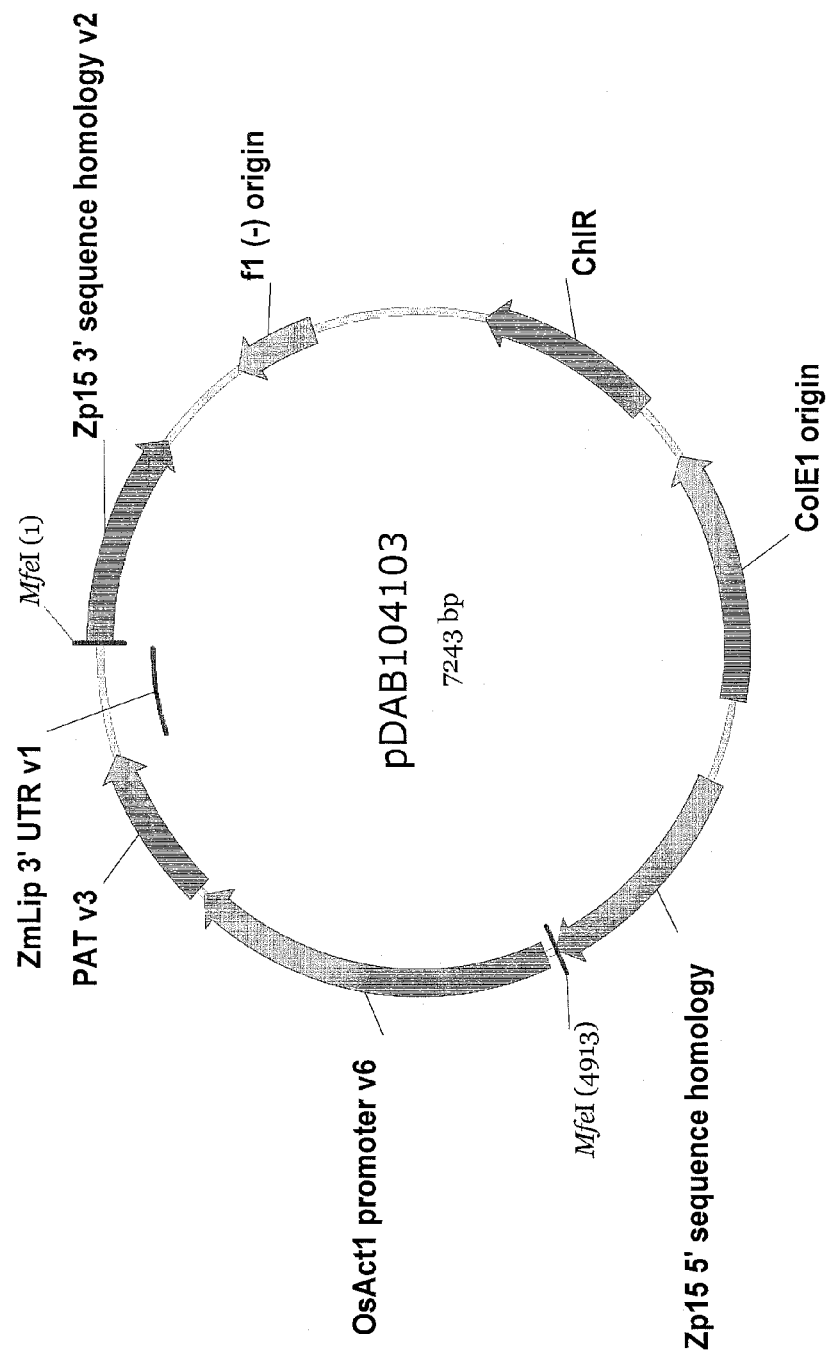
FIG. 14 is a schematic depicting the construct designated pDAB 104103.
Figure 15:
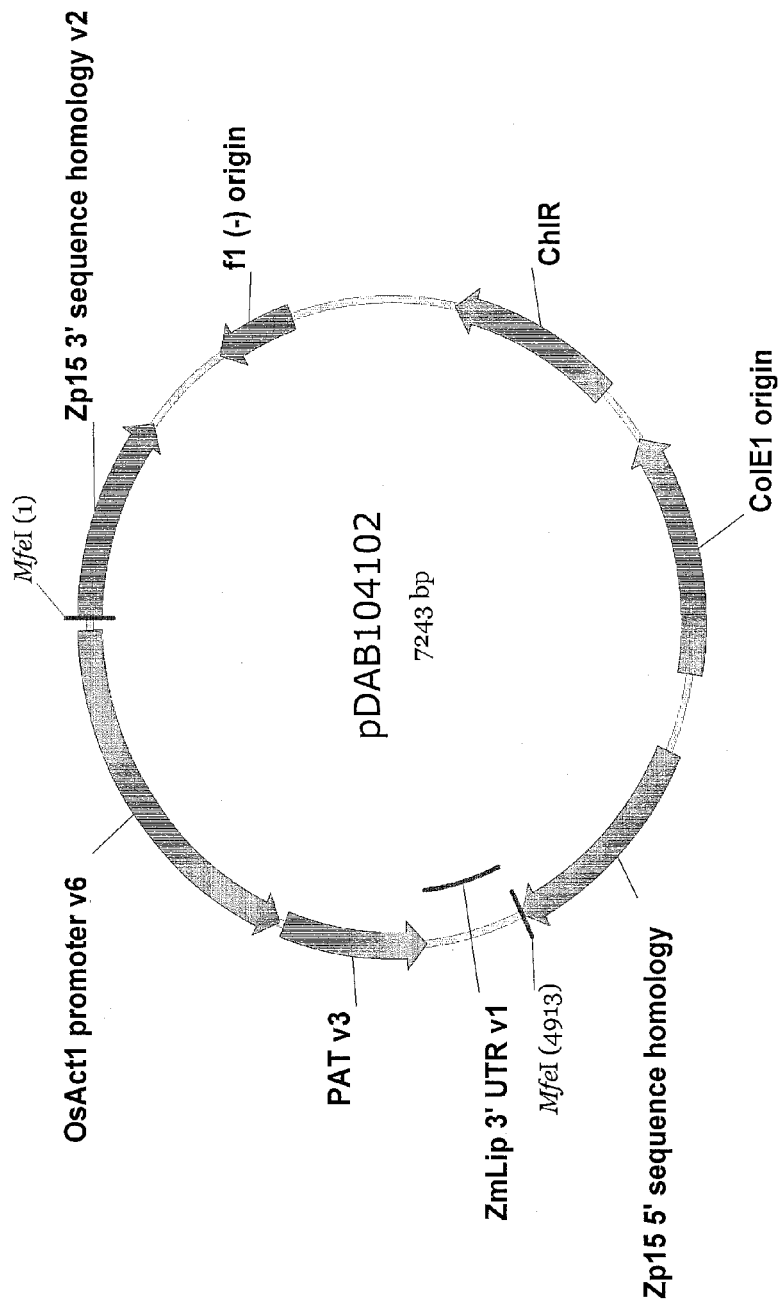
FIG. 15 is a schematic depicting the construct designated pDAB104102.

The PAT gene was removed from pDAB104107 by digestion with Mfe I. After gel electrophoresis, the 2.3 kbp PAT gene fragment was gel purified. The Zp15 homology donor plasmid pDAB104100 was also digested with Mfe I and gel purified. Ligation of the PAT gene into pDAB104100 yielded clones in which the PAT gene was inserted at the Mfe I site in either of two orientations with respect to the Zp15 gene as determined by differential restriction enzyme digestion. pDAB104103 (FIG. 14) comprised the PAT gene inserted in the same transcriptional orientation as the Zp15 gene. pDAB104102 (FIG. 15) comprised the PAT gene inserted in the opposite orientation relative to the Zp15 gene.

C. Transformation of Maize and Recovery of Zp15-Targeted PAT Insertions.

Embryogenic cell cultures of maize variety Hi-II (Armstrong et al. (1991) *Maize Genet Coop Newsletter* 65:92-93) were generated, maintained and subjected to simultaneous transformation of plasmids encoding ZFN24 and donor molecule. Donor molecules include those described here; pDAB104102, pDAB104103, pDAB104104, and pDAB104105. The transformation and selection of callus tissue and subsequent regeneration of transformants is described in U.S. patent application Ser. No. 12/001,939, particularly Example 19, which reference is hereby incorporated by reference in its entirety herein. For additional guidance regarding the transformation and selection protocol see Petolino et al. (2000) *Plant Cell Rept.* 19:781-786. Following anthesis, plants can be either self-pollinated or outcrossed to a maize variety such as DAS5XH751. Resulting progeny seed can be harvested and dried, and plants from these seed can be analyzed to demonstrate the heritability of the targeted integration events. The regeneration of callus into intact, fertile maize plants is described in U.S. patent application Ser. No. 12/001,939, particularly Example 22, which reference is hereby incorporated by reference in its entirety herein.

D. Identification of Zp15-Targeted PAT Insertions

Zp15-targeted PAT insertions in transformed callus tissue are detected by PCR. Template genomic DNA is extracted from callus tissue via well known and commonly used methods such as the Plant DNEASY Kit (QIAGEN Inc., Valencia, Calif.) or the method of Dellaporta (Dellaporta et al., (1983) *Plant Mol. Biol. Rep.* 1; 19-21). Use of PAT specific primers in conjunction with the Zp15 flanking sequence primers already used to detect AAD-1 targeted integration into the Zp15 locus results in the amplification of the PAT targeted insertion junctions in the 5' and 3' Zp15 homology regions. The PAT specific primers can be:

```
DC013
                                         (SEQ ID NO: 120)
5'-CAATCGTAAGCGTTCCTAGCCTTCCAG-3'

DC014
                                         (SEQ ID NO: 121)
5'-CTGGAAGGCTAGGAACGCTTACGATTG-3'
```

Specifically, primers HB501f or HB503f in the genomic region flanking the donor DNA 5' Zp15 homology sequence are used in conjunction with primer DC013 (SEQ ID NO:120) in the PAT protein coding region to detect PAT-Zp15 5' insert junctions when the donor DNAs have the PAT gene in the direct orientation relative to the Zp15 gene. Likewise, primers HB501f or HB503f are used in conjunction with primer DC014 (SEQ ID NO:121) in the PAT protein coding region to detect PAT-Zp15 5' insert junctions when the donor DNAs have the PAT gene in the indirect orientation relative to the Zp15 gene. For detection of PAT-Zp15 3' insert junctions, primers HB502r or HB504r are used in conjunction with primer DC013 (SEQ ID NO:120) to detect insert junctions when the donor DNAs have the PAT gene in the indirect orientation relative to the Zp15 gene. Likewise, primers HB502r or HB504r are used in conjunction with primer DC014 (SEQ ID NO:121) to detect PAT-Zp15 3' insert junctions when the donor DNAs have the PAT gene in the direct orientation relative to the Zp15 gene.

PCR amplification reactions are carried out using PHUSION HOT START DNA Polymerase (New England Biolabs, Beverly, Mass.) under the following cycle conditions: 98° C., 30 s/1 cycle; 98° C. 10 sec, 72° C. 15 sec/33 cycles; 72° C., 5 min/1 cycle; 4° C./hold. PCR products are resolved and identified using TAE agarose gel electrophoresis. The expected gel fragment sizes for the PCR products from PAT-Zp15 targeted integration events in transgenic callus generated using the different PAT-Zp15 donor DNAs are as follows: HB501f/HB503f+DC013 (5')=2.6 kbp (pDAB104103), 2.6 kbp (pDAB104104) HB501f/HB503f+DC014 (5')=1.6 kbp (pDAB104105), 1.7 kbp (pDAB104102) HB502r/HB504r+DC013 (3')=3.2 kbp (pDAB104105), 3.2 kbp (pDAB104102) HB502r/HB504r+DC014 (3')=1.2 kbp (pDAB104103), 1.2 kbp (pDAB104104)

The PCR products comprising the 5' and 3' PAT-Zp15 targeted integration junctions are cloned and sequenced using standard methods known by a person skilled in the art. For example, the PCR products are purified from the agarose gel and cloned into pCR-BluntII TOPO plasmid using TOPO BLUNT CLONING® Kit and ONE SHOT® TOP 10 Chemically competent E. coli cells (Invitrogen Life Technologies, Carlsbad, Calif.) according to manufacturer's protocol.

The cloned integration junctions are then sequenced to demonstrate that the PAT gene is inserted into the maize genome at the Zp15 locus by homologous recombination via the 5' and 3' Zp15 homology sequences that are incorporated into the donor transformation vectors. In addition to the TOPO vector specific primers M13forward and M13reverse, PAT gene cassette specific primers are used to obtain complete sequence of the targeted integration clones. PCR Primers SEQ ID NO:120 and SEQ ID NO:121 which are specific to the PAT protein coding sequence are also used as sequencing primers. In addition, other primers can also be used for sequencing. These include but are not limited to those that are specific to the rice actin promoter element of the PAT cassette:

```
DC-S1
                                         (SEQ ID NO: 122)
5'-CCAACTGGACAATAGTCTCCAC-3'

DC-S2
                                         (SEQ ID NO: 123)
5'-CATCGCCACTATATACATACC-3'
``` and those that are specific to the PAT protein coding sequence:

```
DC-S3
                                         (SEQ ID NO: 124)
5'-CGTCTCAATGTAATGGTTAACG-3'

DC-S4
                                         (SEQ ID NO: 125)
5'-GCCCAGCGTAAGCAATACCAG-3'
```

Example 6

Heritability of AAD-1 Targeted Integration at the Zp15 Locus

A transgenic callus event carrying the AAD-1 gene cassette targeted to the Zp15 locus was generated (Event 138). Event 138 $T_0$ plants were regenerated and crossed as females to DAS5XH751 males. Resulting $T_1$ seed was planted and $T_1$ plants were grown.

$T_1$ plants were analyzed by PCR to demonstrate the occurrence of the AAD-1-Zp15 targeted integration. PCR amplification reactions were carried out using PHUSION HOT START DNA Polymerase (New England Biolabs, Beverly, Mass.) under the following cycle conditions: 98° C., 30 s/1 cycle; 98° C. 10 sec, 72° C. 15 sec/33 cycles; 72° C., 5 min/1 cycle; 4° C./hold. PCR reactions were analyzed by electrophoresis in 1.0% TAE agarose gels. Genomic DNA was extracted from a $T_1$ plant and used as template DNA in PCR reactions with nested primers designed to detect the AAD-1 Zp15 5' integration junction. Primary and secondary PCR reactions were conducted using the same primers used before in the analysis of callus event 147. For primary PCR, primers HB501f and HB507r were used. Primary PCR yielded a band at the expected size of 2.2 kbp. An aliquot of the primary PCR reaction was diluted 1:100 and used as template in secondary PCR using nested primers HB503f and HB508r. Secondary PCR also yielded a band at the expected size of 2.2 kbp.

The 2.2 kbp secondary PCR product was cloned into pCR-Blunt II-TOPO using the ZERO BLUNT TOPO PCR Cloning Kit and ONE SHOT TOP10 Chemically competent E. coli cells (Invitrogen Life Technologies, Carlsbad, Calif.) according to manufacturer's protocol. The cloned DNA was sequenced using flanking vector specific primers (M13forward and M13 reverse). The sequence was found to be identical to that expected for a targeted integration of AAD-1 at the Zp15 locus.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of integrating one or more exogenous nucleic acid sequences into the genome of a plant cell, the method comprising:
   making a double-stranded cleavage in the genome of the plant cell in a Zp15 locus using a zinc finger nuclease comprising a zinc finger binding domain that binds to a target site selected from the group shown in Table 1, thereby resulting in integration of a polynucleotide comprising the one or more exogenous sequences into the genome of the cell in the Zp15 locus.

2. The method of claim 1, further comprising expressing a product of the one or more exogenous sequences.

3. The method of claim 1, wherein the double-stranded cleavage is made by
   (a) expressing a first fusion protein in the cell, the first fusion protein comprising a first zinc finger binding domain and a first cleavage half-domain, wherein the first zinc finger binding domain has been engineered to bind to a first target site selected from the group shown in Table 1 in a Zp15 locus in the genome of the plant cell; and
   (b) expressing a second fusion protein in the cell, the second fusion protein comprising a second zinc finger binding domain and a second cleavage half domain, wherein the second zinc finger binding domain binds to a second target site in the Zp15 locus in the genome of the plant cell, wherein the second target site is different from the first target site; and wherein binding of the first fusion protein to the first target site, and binding of the second fusion protein to the second target site, positions the cleavage half-domains such that the genome of the plant cell in the Zp15 locus is cleaved.

4. The method of claim 3, wherein the zinc finger binding domains are selected from the group shown in Table 1.

5. The method of claim 3, wherein the cleavage half-domains are naturally or non-naturally occurring.

6. The method of claim 1, wherein the one or more exogenous nucleic acid sequences comprise a coding sequence, a regulatory sequence, or a target site for a DNA-binding domain.

7. The method of claim 6, wherein the coding sequence encodes for a product that confers: herbicide resistance; herbicide tolerance; insect resistance; insect tolerance; disease resistance; disease tolerance; stress tolerance; stress resistance; a change in oxidative stress; increased yields of oil; a change in food content and makeup; a change in physical appearance; male sterility; drydown; standability; prolificacy; a change in starch quantity or quality; a change in oil quality; a change in protein quality or quantity; a change in amino acid composition or combinations thereof.

8. The method of claim 1, wherein the polynucleotide further comprises nucleotide sequences that are homologous to sequences in the Zp15 locus.

9. The method according to claim 8, wherein the homologous nucleotide sequences flank the exogenous sequence.

10. The method of claim 1, wherein the polynucleotide further comprises a promoter.

11. The method of claim 1, wherein one or more of the integrated exogenous sequences are transmitted to progeny in subsequent generations.

12. The method of claim 1, wherein the plant cell is a monocotyledonous plant cell.

13. The method of claim 12, wherein the plant cell is a maize cell.

14. A plant or plant part, comprising one or more exogenous sequences integrated into the Zp15 locus by the method of claim 1.

15. A seed comprising one or more exogenous sequences integrated into the Zp15 locus by the method of claim 1.

* * * * *

SEQUENCE LISTING

```
<160> NUMBER OF SEQ ID NOS: 136

<210> SEQ ID NO 1
<211> LENGTH: 21
<212> TYPE: DNA
<213> ORGANISM: Artificial Sequence
<220> FEATURE:
<223> OTHER INFORMATION: Forward PCR Primer
```

```
<400> SEQUENCE: 1
cgtatgaatt cattgacaac c                                         21

<210> SEQ ID NO 2
<211> LENGTH: 19
<212> TYPE: DNA
<213> ORGANISM: Artificial Sequence
<220> FEATURE:
<223> OTHER INFORMATION: Forward PCR Primer

<400> SEQUENCE: 2
atgatctatc tgtaaatcc                                            19

<210> SEQ ID NO 3
<211> LENGTH: 21
<212> TYPE: DNA
<213> ORGANISM: Artificial Sequence
<220> FEATURE:
<223> OTHER INFORMATION: Forward PCR Primer

<400> SEQUENCE: 3
cgtcatgcaa cgcaacattc c                                         21

<210> SEQ ID NO 4
<211> LENGTH: 20
<212> TYPE: DNA
<213> ORGANISM: Artificial Sequence
<220> FEATURE:
<223> OTHER INFORMATION: Forward PCR Primer

<400> SEQUENCE: 4
aagaacatca caagttatgc                                           20

<210> SEQ ID NO 5
<211> LENGTH: 20
<212> TYPE: DNA
<213> ORGANISM: Artificial Sequence
<220> FEATURE:
<223> OTHER INFORMATION: Forward PCR Primer

<400> SEQUENCE: 5
tcatgtggat ccaaggcatc                                           20

<210> SEQ ID NO 6
<211> LENGTH: 19
<212> TYPE: DNA
<213> ORGANISM: Artificial Sequence
<220> FEATURE:
<223> OTHER INFORMATION: Reverse PCR primer

<400> SEQUENCE: 6
atgtgtgtcg tcttactgc                                            19

<210> SEQ ID NO 7
<211> LENGTH: 18
<212> TYPE: DNA
<213> ORGANISM: Artificial Sequence
<220> FEATURE:
<223> OTHER INFORMATION: Reverse PCR Primer

<400> SEQUENCE: 7
cagtagtagg gcggaatg                                             18

<210> SEQ ID NO 8
<211> LENGTH: 15
```

```
<212> TYPE: DNA
<213> ORGANISM: Artificial Sequence
<220> FEATURE:
<223> OTHER INFORMATION: Reverse PCR Primer

<400> SEQUENCE: 8
gggcagctgg tactg                                                        15

<210> SEQ ID NO 9
<211> LENGTH: 18
<212> TYPE: DNA
<213> ORGANISM: Artificial Sequence
<220> FEATURE:
<223> OTHER INFORMATION: Reverse PCR Primer

<400> SEQUENCE: 9
ctataatcga tgtagagc                                                     18

<210> SEQ ID NO 10
<211> LENGTH: 20
<212> TYPE: DNA
<213> ORGANISM: Artificial Sequence
<220> FEATURE:
<223> OTHER INFORMATION: Reverse PCR Primer

<400> SEQUENCE: 10
ctatgctttg tctatagtcg                                                   20

<210> SEQ ID NO 11
<211> LENGTH: 28
<212> TYPE: DNA
<213> ORGANISM: Zea mays

<400> SEQUENCE: 11
cggggctgca gggcttgtac ggcgctgg                                          28

<210> SEQ ID NO 12
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 12

Asp Arg Ser His Leu Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 13

Arg Ser Asp Asn Leu Arg Glu
1               5

<210> SEQ ID NO 14
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 14

Arg Ser Asp Val Leu Ser Glu
```

<210> SEQ ID NO 15
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 15

Arg Ser Ala His Leu Ser Arg
1               5

<210> SEQ ID NO 16
<211> LENGTH: 28
<212> TYPE: DNA
<213> ORGANISM: Zea mays

<400> SEQUENCE: 16
gcaggggcag ggcatctgca ttgcagag                                       28

<210> SEQ ID NO 17
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 17

Gln Ser Gly Ser Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 18

Arg Ser Asp His Leu Thr Gln
1               5

<210> SEQ ID NO 19
<211> LENGTH: 28
<212> TYPE: DNA
<213> ORGANISM: Zea mays

<400> SEQUENCE: 19
ctgaggcagc cgcagtgcag cccgctgg                                       28

<210> SEQ ID NO 20
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 20

Gln Ser Gly Asp Leu Thr Arg
1               5

<210> SEQ ID NO 21
<211> LENGTH: 7
<212> TYPE: PRT
<213> ORGANISM: Artificial Sequence
<220> FEATURE:

<223> OTHER INFORMATION: zinc finger binding domain

<400> SEQUENCE: 21

Asp Arg Ser Asp Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 22

Arg Ser Asp Asn Leu Thr Arg
1               5

<210> SEQ ID NO 23
<211> LENGTH: 28
<212> TYPE: DNA
<213> ORGANISM: Zea mays

<400> SEQUENCE: 23
actccgcgta ggggtacagc ccgccggc                                     28

<210> SEQ ID NO 24
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 24

Arg Ser Asp His Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 25

Arg Ser Asp Asn Leu Thr Thr
1               5

<210> SEQ ID NO 26
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 26

Arg Ser Asp Asp Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 27

Asp Ser Ser Asp Arg Lys Lys

```
<210> SEQ ID NO 28
<211> LENGTH: 28
<212> TYPE: DNA
<213> ORGANISM: Zea mays

<400> SEQUENCE: 28
ctgcccagct accgcaccaa cccctgtg                                        28

<210> SEQ ID NO 29
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 29

Arg Ser Asp His Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 30

Arg Asn Asp Asn Arg Lys Asn
1               5

<210> SEQ ID NO 31
<211> LENGTH: 28
<212> TYPE: DNA
<213> ORGANISM: Zea mays

<400> SEQUENCE: 31
agccgcagtg cagcccgctg gcggcggc                                        28

<210> SEQ ID NO 32
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 32

Gln Ser Ser Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 33

Thr Ser Ser Thr Arg Lys Thr
1               5

<210> SEQ ID NO 34
<211> LENGTH: 7
<212> TYPE: PRT
<213> ORGANISM: Artificial Sequence
<220> FEATURE:
```

```
<223> OTHER INFORMATION: zinc finger binding domain

<400> SEQUENCE: 34

Arg Ser Asp Ser Leu Ser Ala
1               5

<210> SEQ ID NO 35
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 35

Arg Ser Ser Thr Arg Lys Glu
1               5

<210> SEQ ID NO 36
<211> LENGTH: 28
<212> TYPE: DNA
<213> ORGANISM: Zea mays

<400> SEQUENCE: 36
cctcaggtac tccgcgtagg ggtacagc                                           28

<210> SEQ ID NO 37
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 37

Arg Ser Asp Thr Leu Ser Glu
1               5

<210> SEQ ID NO 38
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 38

Ala Arg Ser Thr Arg Thr Asn
1               5

<210> SEQ ID NO 39
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 39

Gln Ser Ser His Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 40

Gln Ser Ala Asp Arg Thr Lys
```

<210> SEQ ID NO 41
<211> LENGTH: 28
<212> TYPE: DNA
<213> ORGANISM: Zea mays

<400> SEQUENCE: 41
gcccgctggc ggcggcgccc tactacgc                                      28

<210> SEQ ID NO 42
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 42

Arg Ser Asp Thr Leu Ser Ala
1               5

<210> SEQ ID NO 43
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 43

Arg Asn Gln Asp Arg Lys Thr
1               5

<210> SEQ ID NO 44
<211> LENGTH: 28
<212> TYPE: DNA
<213> ORGANISM: Zea mays

<400> SEQUENCE: 44
gcactgcggc tgcctcaggt actccgcg                                      28

<210> SEQ ID NO 45
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 45

Gln Ser Ser Asp Leu Arg Arg
1               5

<210> SEQ ID NO 46
<211> LENGTH: 28
<212> TYPE: DNA
<213> ORGANISM: Zea mays

<400> SEQUENCE: 46
cgccgggtgt gggcagccga gcgccatg                                      28

<210> SEQ ID NO 47
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 47

Asp Arg Ser His Leu Ser Arg
1               5

<210> SEQ ID NO 48
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 48

Arg Ser Asp Ala Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 49

Arg Ser Asp Asp Arg Lys Thr
1               5

<210> SEQ ID NO 50
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 50

Asp Asn Ser Asn Arg Ile Lys
1               5

<210> SEQ ID NO 51
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 51

Arg Ser Asp His Leu Thr Thr
1               5

<210> SEQ ID NO 52
<211> LENGTH: 28
<212> TYPE: DNA
<213> ORGANISM: Zea mays

<400> SEQUENCE: 52
gccgggtgtg ggcagccgag cgccatgt                                    28

<210> SEQ ID NO 53
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 53

Arg Ser Asp Ser Leu Leu Arg
1               5

```
<210> SEQ ID NO 54
<211> LENGTH: 28
<212> TYPE: DNA
<213> ORGANISM: Zea mays

<400> SEQUENCE: 54
agtagggcgc cgccgccagc gggctgca                                              28

<210> SEQ ID NO 55
<211> LENGTH: 28
<212> TYPE: DNA
<213> ORGANISM: Zea mays

<400> SEQUENCE: 55
tgtgggcagc cgagcgccat gttccagc                                              28

<210> SEQ ID NO 56
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 56

Arg Ser Asp Asn Leu Ala Arg
1               5

<210> SEQ ID NO 57
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 57

Arg Ser Asp Asn Leu Ser Glu
1               5

<210> SEQ ID NO 58
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 58

Arg Ser Asp Asn Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 59

Asp Asn Ser Thr Arg Lys Thr
1               5

<210> SEQ ID NO 60
<211> LENGTH: 28
<212> TYPE: DNA
<213> ORGANISM: Zea mays

<400> SEQUENCE: 60
cggcgtagta gggcgccgcc gccagcgg                                              28
```

```
<210> SEQ ID NO 61
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 61

Arg Ser Asp Asn Leu Ser Thr
1               5

<210> SEQ ID NO 62
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 62

Arg Ser Ala Asp Leu Ser Arg
1               5

<210> SEQ ID NO 63
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 63

Ala Ser Lys Thr Arg Lys Asn
1               5

<210> SEQ ID NO 64
<211> LENGTH: 28
<212> TYPE: DNA
<213> ORGANISM: Zea mays

<400> SEQUENCE: 64
cagccgctcc ggcaacagtg ctgccagc                                           28

<210> SEQ ID NO 65
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 65

Gln Ser Ser Asp Leu Ser Arg
1               5

<210> SEQ ID NO 66
<211> LENGTH: 28
<212> TYPE: DNA
<213> ORGANISM: Zea mays

<400> SEQUENCE: 66
acatggcgct cggctgccca cacccggc                                           28

<210> SEQ ID NO 67
<211> LENGTH: 7
<212> TYPE: PRT
<213> ORGANISM: Artificial Sequence
<220> FEATURE:
<223> OTHER INFORMATION: zinc finger binding domain
```

```
<400> SEQUENCE: 67

Arg Asn Asp Asp Arg Lys Lys
1               5

<210> SEQ ID NO 68
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 68

Arg Ser Asp Ala Leu Thr Gln
1               5

<210> SEQ ID NO 69
<211> LENGTH: 28
<212> TYPE: DNA
<213> ORGANISM: Zea mays

<400> SEQUENCE: 69
tggcagccca gggtctcaac cccatggc                                       28

<210> SEQ ID NO 70
<211> LENGTH: 28
<212> TYPE: DNA
<213> ORGANISM: Zea mays

<400> SEQUENCE: 70
cagctgctgc tgctgctgca tcagagct                                       28

<210> SEQ ID NO 71
<211> LENGTH: 28
<212> TYPE: DNA
<213> ORGANISM: Zea mays

<400> SEQUENCE: 71
tggtactggt agagtccacc catggccg                                       28

<210> SEQ ID NO 72
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 72

Arg Ser Asp Ala Leu Ser Asn
1               5

<210> SEQ ID NO 73
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 73

Thr Ser Ser Ala Arg Thr Thr
1               5

<210> SEQ ID NO 74
<211> LENGTH: 28
<212> TYPE: DNA
<213> ORGANISM: Zea mays
```

```
<400> SEQUENCE: 74
aacccctgtg gcgtctccgc tgccattc                                      28

<210> SEQ ID NO 75
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 75

Asp Arg Ser Ala Leu Ser Arg
1               5

<210> SEQ ID NO 76
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 76

Asp Arg Ser His Leu Ala Arg
1               5

<210> SEQ ID NO 77
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 77

Asp Arg Ser Thr Arg Thr Thr
1               5

<210> SEQ ID NO 78
<211> LENGTH: 28
<212> TYPE: DNA
<213> ORGANISM: Zea mays

<400> SEQUENCE: 78
gtgcggtagc tgggcagctg gtactggt                                      28

<210> SEQ ID NO 79
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 79

Gln Ser Gly Ala Leu Ala Arg
1               5

<210> SEQ ID NO 80
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 80

Arg Ser Asp His Leu Ser Thr
1               5
```

```
<210> SEQ ID NO 81
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 81

His Ser Asp Thr Arg Lys Lys
1               5

<210> SEQ ID NO 82
<211> LENGTH: 28
<212> TYPE: DNA
<213> ORGANISM: Zea mays

<400> SEQUENCE: 82
aggcggggct tgacgaagtt ggaagccg                                    28

<210> SEQ ID NO 83
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 83

Arg Ser Asp Ser Leu Ser Val
1               5

<210> SEQ ID NO 84
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 84

Gln Asn Gln His Arg Ile Asn
1               5

<210> SEQ ID NO 85
<211> LENGTH: 28
<212> TYPE: DNA
<213> ORGANISM: Zea mays

<400> SEQUENCE: 85
aaatggaaaa aacgctaaaa ttatgtgt                                    28

<210> SEQ ID NO 86
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 86

Arg Ser Asp Asp Leu Ser Lys
1               5

<210> SEQ ID NO 87
<211> LENGTH: 7
<212> TYPE: PRT
<213> ORGANISM: Artificial Sequence
<220> FEATURE:
<223> OTHER INFORMATION: zinc finger binding domain
```

```
<400> SEQUENCE: 87

Arg Asn Asp His Arg Lys Asn
1               5

<210> SEQ ID NO 88
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 88

Gln Arg Ser Asn Leu Val Arg
1               5

<210> SEQ ID NO 89
<211> LENGTH: 28
<212> TYPE: DNA
<213> ORGANISM: Zea mays

<400> SEQUENCE: 89
ttgtggtgcc aacgggagcc atgctcac                                      28

<210> SEQ ID NO 90
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 90

Arg Ser Asp Thr Leu Ser Gln
1               5

<210> SEQ ID NO 91
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 91

Gln Asn Ala Thr Arg Ile Asn
1               5

<210> SEQ ID NO 92
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 92

Arg Ser Asp Ala Leu Ser Arg
1               5

<210> SEQ ID NO 93
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 93

Gln Lys Ala Thr Arg Ile Thr
1               5
```

```
<210> SEQ ID NO 94
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 94

Gln Asn Ala Asn Arg Lys Thr
1               5

<210> SEQ ID NO 95
<211> LENGTH: 28
<212> TYPE: DNA
<213> ORGANISM: Zea mays

<400> SEQUENCE: 95
caatcacgcc ggtagcgggg ctagttat                                      28

<210> SEQ ID NO 96
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 96

Asp Ser Ser Ala Arg Lys Lys
1               5

<210> SEQ ID NO 97
<211> LENGTH: 26
<212> TYPE: DNA
<213> ORGANISM: Artificial Sequence
<220> FEATURE:
<223> OTHER INFORMATION: Forward PCR Primer

<400> SEQUENCE: 97
gcggccgcat gcaagagctg ttgatc                                        26

<210> SEQ ID NO 98
<211> LENGTH: 33
<212> TYPE: DNA
<213> ORGANISM: Artificial Sequence
<220> FEATURE:
<223> OTHER INFORMATION: Reverse PCR Primer

<400> SEQUENCE: 98
caattgccgg cgtagtaggg cgccgccgcc agc                                33

<210> SEQ ID NO 99
<211> LENGTH: 34
<212> TYPE: DNA
<213> ORGANISM: Artificial Sequence
<220> FEATURE:
<223> OTHER INFORMATION: Forward PCR Primer

<400> SEQUENCE: 99
caattggtgt gggcagccga gcgccatgtt ccag                               34

<210> SEQ ID NO 100
<211> LENGTH: 35
<212> TYPE: DNA
<213> ORGANISM: Artificial Sequence
<220> FEATURE:
<223> OTHER INFORMATION: Reverse PCR Primer
```

<400> SEQUENCE: 100
gtcgaccgat actgatgcgg accgtccacc ttgtc                            35

<210> SEQ ID NO 101
<211> LENGTH: 29
<212> TYPE: DNA
<213> ORGANISM: Artificial Sequence
<220> FEATURE:
<223> OTHER INFORMATION: Forward PCR Primer

<400> SEQUENCE: 101
caattggtca ttcatatgct tgagaagag                                   29

<210> SEQ ID NO 102
<211> LENGTH: 28
<212> TYPE: DNA
<213> ORGANISM: Artificial Sequence
<220> FEATURE:
<223> OTHER INFORMATION: Reverse PCR Primer

<400> SEQUENCE: 102
caattgagca cttaaagatc tttagaag                                    28

<210> SEQ ID NO 103
<211> LENGTH: 30
<212> TYPE: DNA
<213> ORGANISM: Artificial Sequence
<220> FEATURE:
<223> OTHER INFORMATION: Forward PCR Primer

<400> SEQUENCE: 103
aaggtcccaa atctgaggca tactgttgct                                  30

<210> SEQ ID NO 104
<211> LENGTH: 30
<212> TYPE: DNA
<213> ORGANISM: Artificial Sequence
<220> FEATURE:
<223> OTHER INFORMATION: Reverse PCR Primer

<400> SEQUENCE: 104
gaggtcctat gctttgtcta tagtcggcag                                  30

<210> SEQ ID NO 105
<211> LENGTH: 26
<212> TYPE: DNA
<213> ORGANISM: Artificial Sequence
<220> FEATURE:
<223> OTHER INFORMATION: Forward PCR PRimer

<400> SEQUENCE: 105
ggcatactgt tgctgccctg ctggaa                                      26

<210> SEQ ID NO 106
<211> LENGTH: 30
<212> TYPE: DNA
<213> ORGANISM: Artificial Sequence
<220> FEATURE:
<223> OTHER INFORMATION: Reverse PCR Primer

<400> SEQUENCE: 106
gacacctata atcgatgtag agccgaagag                                  30

<210> SEQ ID NO 107
<211> LENGTH: 26
<212> TYPE: DNA

```
<213> ORGANISM: Artificial Sequence
<220> FEATURE:
<223> OTHER INFORMATION: Forward PCR Primer

<400> SEQUENCE: 107
agtccacccc agtgatctca gcacca                                          26

<210> SEQ ID NO 108
<211> LENGTH: 30
<212> TYPE: DNA
<213> ORGANISM: Artificial Sequence
<220> FEATURE:
<223> OTHER INFORMATION: Forward PCR Primer

<400> SEQUENCE: 108
agtggctgga cagctattct ctcaaagcgt                                      30

<210> SEQ ID NO 109
<211> LENGTH: 30
<212> TYPE: DNA
<213> ORGANISM: Artificial Sequence
<220> FEATURE:
<223> OTHER INFORMATION: Reverse PCR Primer

<400> SEQUENCE: 109
acgctttgag agaatagctg tccagccact                                      30

<210> SEQ ID NO 110
<211> LENGTH: 26
<212> TYPE: DNA
<213> ORGANISM: Artificial Sequence
<220> FEATURE:
<223> OTHER INFORMATION: Reverse PCR Primer

<400> SEQUENCE: 110
tggtgctgag atcactgggg tggact                                          26

<210> SEQ ID NO 111
<211> LENGTH: 752
<212> TYPE: DNA
<213> ORGANISM: Zea mays

<400> SEQUENCE: 111
atgcaagagc tgttgatcat tcagagcaat gtattggttg tgagtttttg acggcgctca     60
cagtgataga tttgttatct atatgccagc cccagcatat tcatccttgt gctgtgggcg    120
tctagaggac cgacaatata tatttttta aaacaaattc gtgaagaaca tcacaagtta     180
tgcatgcaaa ctgctcaagt catgtggatc caaggcatcc taacaactag cacagcatta    240
caacaaaata ttggtgtata tgtgcctaca atgaagtgaa aggtgatgag tcatggtgat    300
gtgtaaagag gcattacaaa gttagcttca caagcgtatg aattcattga caaccctgta    360
catgtaaagt tgattcatat gtataagaaa gcttaatgat ctatctgtaa atccaaatcc    420
atgtactatg tttccacgtc atgcaacgca acattccaaa accatgggtt gcaagatgct    480
gcagaatgca agccatggat catctataaa tggctagctc ccacatatga actagtctct    540
atcatcatcc aatccagatc agcaaagcgg cagtgcgtag agaggatcgt cgaacagaac    600
agcatgaaga tggtcatcgt tctcgtcgtg tgcctggctc tgtcagctgc cagcgcctct    660
gcaatgcaga tgcctgcccc ctgcgcgggg ctgcagggct tgtacggcgc tggcgccggc    720
ctgacgacga tgatgggcgc cggcgggctg ta                                  752

<210> SEQ ID NO 112
```

<211> LENGTH: 775
<212> TYPE: DNA
<213> ORGANISM: Zea mays

<400> SEQUENCE: 112

| | | | | | |
|---|---|---|---|---|---|
| cgccatgttc | cagccgctcc | ggcaacagtg | ctgccagcag | cagatgagga | tgatggacgt | 60 |
| gcagtccgtc | gcgcagcagc | tgcagatgat | gatgcagctt | gagcgtgccg | ctgccgccag | 120 |
| cagcagcctg | tacgagccag | ctctgatgca | gcagcagcag | cagctgctgg | cagcccaggg | 180 |
| tctcaaccc | atggccatga | tgatggcgca | gaacatgccg | ccatgggtg | gactctacca | 240 |
| gtaccagctg | cccagctacc | gcaccaaccc | tgtggcgtc | tccgctgcca | ttccgcccta | 300 |
| ctactgattc | atgatatttg | ggaaatctcc | tctatccatc | tctctctatc | tatatatgta | 360 |
| ataatgcagt | aagacgacac | acattatcat | gtgtggtatg | accaataata | tatgcatggt | 420 |
| cataataaag | ttttggtttt | aatgaatcta | tcggccgctt | gatgtctatg | atggacaaat | 480 |
| caaaacttct | cctgtcaggc | atgtaaatat | ttcaaaatct | ctattcaggc | tcaaattcat | 540 |
| agcatatggg | tagagtagta | tgcttgagat | tagcaacttt | atacttgagt | atagagtata | 600 |
| aaacataaag | tcatgtgtat | tctattggct | agataagtgt | aaatgtgagt | ttagaggcaa | 660 |
| caaccatgat | ttgaatccta | atttacacat | aattttagcg | ttttttccat | ttaaaggcgg | 720 |
| ggcttgacga | agttggaagc | cgtggaactg | ctggggctta | tcttgacaac | aaatc | 775 |

<210> SEQ ID NO 113
<211> LENGTH: 1561
<212> TYPE: DNA
<213> ORGANISM: Artificial Sequence
<220> FEATURE:
<223> OTHER INFORMATION: Zp 15 5' and 3' flanking regions containing an MfeI restriction site

<400> SEQUENCE: 113

| | | | | | |
|---|---|---|---|---|---|
| gcggccgcat | gcaagagctg | ttgatcattc | agagcaatgt | attggttgtg | agttttgac | 60 |
| ggcgctcaca | gtgatagatt | tgttatctat | atgccagccc | cagcatattc | atccttgtgc | 120 |
| tgtgggcgtc | tagaggaccg | acaatatata | tattttaaa | acaaattcgt | gaagaacatc | 180 |
| acaagttatg | catgcaaact | gctcaagtca | tgtggatcca | aggcatccta | acaactagca | 240 |
| cagcattaca | acaaaatatt | ggtgtatatg | tgcctacaat | gaagtgaaag | gtgatgagtc | 300 |
| atggtgatgt | gtaagaggc | attacaaagt | tagcttcaca | agcgtatgaa | ttcattgaca | 360 |
| acccttgaca | tgtaaagttg | attcatatgt | ataagaaagc | ttaatgatct | atctgtaaat | 420 |
| ccaaatccat | gtactatgtt | tccacgtcat | gcaacgcaac | attccaaaac | catgggttgc | 480 |
| aagatgctgc | agaatgcaag | ccatggatca | tctataaatg | gctagctccc | acatatgaac | 540 |
| tagtctctat | catcatccaa | tccagatcag | caaagcggca | gtgcgtagag | aggatcgtcg | 600 |
| aacagaacag | catgaagatg | gtcatcgttc | tcgtcgtgtg | cctggctctg | tcagctgcca | 660 |
| gcgcctctgc | aatgcagatg | ccctgccct | gcgcggggct | gcagggcttg | tacggcgctg | 720 |
| gcgccggcct | gacgacgatg | atgggcgccg | gcgggctgta | caattgccta | ggcaattgcg | 780 |
| ccatgttcca | gccgctccgg | caacagtgct | gccagcagca | gatgaggatg | atggacgtgc | 840 |
| agtccgtcgc | gcagcagctg | cagatgatga | tgcagcttga | gcgtgccgct | gccgccagca | 900 |
| gcagcctgta | cgagccagct | ctgatgcagc | agcagcagca | gctgctggca | gcccaggtc | 960 |
| tcaaccccat | ggccatgatg | atggcgcaga | acatgccggc | catggtgga | ctctaccagt | 1020 |
| accagctgcc | cagctaccgc | accaacccct | gtggcgtctc | cgctgccatt | ccgccctact | 1080 |
| actgattcat | gatatttggg | aaatctcctc | tatccatctc | tctctatcta | tatgtaat | 1140 |

```
aatgcagtaa gacgacacac attatcatgt gtggtatgac caataatata tgcatggtca    1200
taataaagtt ttggttttaa tgaatctatc ggccgcttga tgtctatgat ggacaaatca    1260
aaacttctcc tgtcaggcat gtaaatattt caaaatctct attcaggctc aaattcatag    1320
catatgggta gagtagtatg cttgagatta gcaactttat acttgagtat agagtataaa    1380
acataaagtc atgtgtattc tattggctag ataagtgtaa atgtgagttt agaggcaaca    1440
accatgattt gaatcctaat ttacacataa ttttagcgtt ttttccattt aaaggcgggg    1500
cttgacgaag ttggaagccg tggaactgct ggggcttatc ttgacaacaa atcgcggccg    1560
c                                                                    1561

<210> SEQ ID NO 114
<211> LENGTH: 34
<212> TYPE: DNA
<213> ORGANISM: Artificial Sequence
<220> FEATURE:
<223> OTHER INFORMATION: Primer

<400> SEQUENCE: 114
ccagtgcaat tgggtcattc atatgcttga gaag                                34

<210> SEQ ID NO 115
<211> LENGTH: 36
<212> TYPE: DNA
<213> ORGANISM: Artificial Sequence
<220> FEATURE:
<223> OTHER INFORMATION: PCR Primer

<400> SEQUENCE: 115
ccagtgcaat tgaattcagc acttaaagat ctttag                              36

<210> SEQ ID NO 116
<211> LENGTH: 2349
<212> TYPE: DNA
<213> ORGANISM: Artificial Sequence
<220> FEATURE:
<223> OTHER INFORMATION: PAT expression cassette

<400> SEQUENCE: 116
ccagtgcaat tgggtcattc atatgcttga gaagagagtc gggatagtcc aaaataaaac    60
aaaggtaaga ttacctggtc aaaagtgaaa acatcagtta aaaggtggta taagtaaaa     120 tatcggtaat aaaaggtggc ccaaagtgaa atttactctt ttctactatt ataaaaattg    180
aggatgtttt tgtcggtact tgatacgtc attttttgtat gaattggttt ttaagtttat    240
tcgcttttgg aaatgcatat ctgtatttga gtcgggtttt aagttcgttt gcttttgtaa    300
atacagaggg atttgtataa gaaatatctt taaaaaaacc catatgctaa tttgacataa    360
tttttgagaa aaatatatat tcgggcgaat tctcacaatg aacaataata agattaaaat    420
agctttcccc cgttgcagcg catgggtatt ttttctagta aaaataaaag ataaacttag    480
actcaaaaca tttacaaaaa caacccctaa agttcctaaa gcccaaagtg ctatccacga    540
tccatagcaa gcccagccca acccaaccca acccaaccca cccagtcca gccaactgga    600 caatagtctc cacacccccc cactatcacc gtgagttgtc cgcacgcacc gcacgtctcg    660
cagccaaaaa aaaaaaaaga aagaaaaaaa agaaaaagaa aaaacagcag gtgggtccgg    720 gtcgtgggggg ccggaaacgc gaggaggatc gcgagccagc gacgaggccg gccctccctc    780
cgcttccaaa gaaacgcccc catcgccac tatatacata cccccccctc tcctcccatc     840
ccccaacccc taccaccacc accaccacca cctccacctc ctcccccctc gctgccggac    900
```

```
gacgcctccc ccctccccct ccgccgccgc cgcgccggta accacccgc ccctctcctc      960 tttctttctc cgttttttt ttccgtctcg gtctcgatct ttggccttgg tagtttgggt     1020
gggcgagagg cggcttcgtg cgcgcccaga tcggtgcgcg ggaggggcgg gatctcgcgg     1080
ctggggctct cgccggcgtg gatccggccc ggatctcgcg gggaatgggg ctctcggatg     1140
tagatctgcg atccgccgtt gttgggggag atgatggggg gtttaaaatt tccgccatgc     1200
taaacaagat caggaagagg ggaaaagggc actatggttt atattttat atatttctgc     1260 tgcttcgtca ggcttagatg tgctagatct ttcttcttc tttttgtggg tagaatttga     1320
atccctcagc attgttcatc ggtagttttt cttttcatga tttgtgacaa atgcagcctc     1380
gtgcggagct tttttgtagg tagaccatgg cttctccgga gaggagacca gttgagatta     1440
ggccagctac agcagctgat atggccgcgg tttgtgtatat cgttaaccat tacattgaga     1500
cgtctacagt gaactttagg acagagccac aaacaccaca agagtggatt gatgatctag     1560
agaggttgca agatagatac ccttggttgg ttgctgaggt tgagggtgtt gtggctggta     1620
ttgcttacgc tgggccctgg aaggctagga acgcttacga ttggacagtt gagagtactg     1680
tttacgtgtc acataggcat caaaggttgg gcctaggatc cacattgtac acacatttgc     1740
ttaagtctat ggaggcgcaa ggttttaagt ctgtggttgc tgttataggc cttccaaacg     1800
atccatctgt taggttgcat gaggcttggg gatacacagc ccggggtaca ttgcgcgcag     1860
ctggatacaa gcatggtgga tggcatgatg ttggttttg gcaaagggat tttgagttgc     1920
cagctcctcc aaggcagtt aggccagtta cccagatctg aggtaccctg agctcggtcg     1980
cagcgtgtgc gtgtccgtcg tacgttctgg ccggccgggc cttgggcgcg cgatcagaag     2040
cgttgcgttg gcgtgtgtgt gcttctggtt tgctttaatt ttaccaagtt tgtttcaagg     2100
tggatcgcgt ggtcaaggcc cgtgtgcttt aaagacccac cggcactggc agtgagtgtt     2160
gctgcttgtg taggctttgg tacgtatggg ctttatttgc ttctggatgt tgtgtactac     2220
ttgggtttgt tgaattatta tgagcagttg cgtattgtaa ttcagctggg ctacctggac     2280
attgttatgt attaataaat gctttgcttt cttctaaaga tctttaagtg ctgaattcaa     2340
ttgcactgg                                                             2349
```

<210> SEQ ID NO 117
<211> LENGTH: 34
<212> TYPE: DNA
<213> ORGANISM: Artificial Sequence
<220> FEATURE:
<223> OTHER INFORMATION: PCR Primer

<400> SEQUENCE: 117
ctaatcgtcg actcgtcaag ccccgccttt aaat                                    34

<210> SEQ ID NO 118
<211> LENGTH: 29
<212> TYPE: DNA
<213> ORGANISM: Artificial Sequence
<220> FEATURE:
<223> OTHER INFORMATION: PCR Primer

<400> SEQUENCE: 118
ctaatccaat tggtgtgggc agccgagcg                                          29

<210> SEQ ID NO 119
<211> LENGTH: 769
<212> TYPE: DNA
<213> ORGANISM: Zea mays

<400> SEQUENCE: 119

```
ctaatccaat tggtgtgggc agccgagcgc catgttccag ccgctccggc aacagtgctg    60
ccagcagcag atgaggatga tggacgtgca gtccgtcgcg cagcagctgc agatgatgat   120
gcagcttgag cgtgccgctg ccgccagcag cagcctgtac gagccagctc tgatgcagca   180
gcagcagcag ctgctggcag cccagggtct caaccccatg ccatgatga tggcgcagaa   240
catgccggcc atgggtggac tctaccagta ccagctgccc agctaccgca ccaaccctg    300
tggcgtctcc gctgccattc cgccctacta ctgattcatg atatttggga aatctcctct   360
atccatctct ctctatctat atatgtaata atgcagtaag acgacacaca ttatcatgtg   420
tggtatgacc aataatatat gcatggtcat aataaagttt tggttttaat gaatctatcg   480
gccgcttgat gtctatgatg acaaatcaa aacttctcct gtcaggcatg taaatatttc    540
aaaatctcta ttcaggctca aattcatagc atatgggtag agtagtatgc ttgagattag   600
caactttata cttgagtata gagtataaaa cataaagtca tgtgtattct attggctaga   660
taagtgtaaa tgtgagttta gaggcaacaa ccatgatttg aatcctaatt tacacataat   720
tttagcgttt tttccattta aaggcggggc ttgacgagtc gacgattag                769
```

<210> SEQ ID NO 120
<211> LENGTH: 27
<212> TYPE: DNA
<213> ORGANISM: Artificial Sequence
<220> FEATURE:
<223> OTHER INFORMATION: PCR Primer

<400> SEQUENCE: 120

```
caatcgtaag cgttcctagc cttccag                                         27
```

<210> SEQ ID NO 121
<211> LENGTH: 27
<212> TYPE: DNA
<213> ORGANISM: Artificial Sequence
<220> FEATURE:
<223> OTHER INFORMATION: PCR Primer

<400> SEQUENCE: 121

```
ctggaaggct aggaacgctt acgattg                                         27
```

<210> SEQ ID NO 122
<211> LENGTH: 22
<212> TYPE: DNA
<213> ORGANISM: Artificial Sequence
<220> FEATURE:
<223> OTHER INFORMATION: Sequencing Primer

<400> SEQUENCE: 122

```
ccaactggac aatagtctcc ac                                              22
```

<210> SEQ ID NO 123
<211> LENGTH: 21
<212> TYPE: DNA
<213> ORGANISM: Artificial Sequence
<220> FEATURE:
<223> OTHER INFORMATION: Sequencing Primer

<400> SEQUENCE: 123

```
catcgccact atatacatac c                                               21
```

<210> SEQ ID NO 124
<211> LENGTH: 22

```
<212> TYPE: DNA
<213> ORGANISM: Artificial Sequence
<220> FEATURE:
<223> OTHER INFORMATION: Sequening Primer

<400> SEQUENCE: 124
cgtctcaatg taatggttaa cg                                              22

<210> SEQ ID NO 125
<211> LENGTH: 21
<212> TYPE: DNA
<213> ORGANISM: Artificial Sequence
<220> FEATURE:
<223> OTHER INFORMATION: Sequening Primer

<400> SEQUENCE: 125
gcccagcgta agcaatacca g                                               21

<210> SEQ ID NO 126
<211> LENGTH: 2215
<212> TYPE: DNA
<213> ORGANISM: Zea mays

<400> SEQUENCE: 126
tcgtgaagaa catcacaagt tatgcatgca aactgctcaa gtcatgtgga tccaaggcat      60
cctaacaact agcacagcat tacaacaaaa tattggtgta tatgtgccta caatgaagtg     120
aaaggtgatg agtcatggtg atgtgtaaag aggcattaca aagttagctt cacaagcgta     180
tgaattcatt gacaacccct tgacatgtaaa gttgattcat atgtataaga agcttaatg     240 atctatctgt aaatccaaat ccatgtacta tgtttccacg tcatgcaacg caacattcca     300
aaaccatggg ttgcaagatg ctgcagaatg caagccatgg atcatctata aatggctagc     360
tcccacatat gaactagtct ctatcatcat ccaatccaga tcagcaaagc ggcagtgcgt     420
agagaggatc gtcgaacaga acagcatgaa gatggtcatc gttctcgtcg tgtgcctggc     480
tctgtcagct gccagcgcct ctgcaatgca gatgccctgc cctgcgcgg ggctgcaggg      540 cttgtacggc gctggcgccg gcctgacgac gatgatgggc gccggcgggc tgtacccta     600 cgcggagtac ctgaggcagc cgcagtgcag cccgctggcg gcggcgccct actacgccgg     660
gtgtgggcag ccgagcgcca tgttccagcc gctccggcaa cagtgctgcc agcagcagat     720
gaggatgatg gacgtgcagt ccgtcgcgca gcagctgcag atgatgatgc agcttgagcg     780
tgccgctgcc gccagcagca gcctgtacga gccagctctg atgcagcagc agcagcagct     840
gctggcagcc cagggtctca acccatggc catgatgatg gcgcagaaca tgccggccat      900
gggtggactc taccagtacc agctgcccag ctaccgcacc aaccctgtg gcgtctccgc      960 tgccattccg ccctactact gattcatgat atttgggaaa tctcctctat ccatctctct    1020
ctatctatat atgtaataat gcagtaagac gacacacatt atcatgtgtg gtatgaccaa    1080
taatatatgc atggtcataa taaagttttg gttttaatga atctatcggc cgcttgatgt    1140
ctatgatgga caaatcaaag cttctcctgt caggcatgta aatatttcaa aatctctatt    1200
caggctcaaa ttcatagcat atgggtagag tagtatgctt gagattagca actttatact    1260
tgagtataga gtataaaaca taaagtcatg tgtattctat tggctagata agtgtaaatg    1320
tgagtttaga ggcaacaacc atgatttgaa tcctaattta cacataattt tagcgttttt    1380
tccatttaaa ggcggggctt gacgaagttg gaagccgtgg aactgctggg gcttatcttg    1440
acaacaaatc attccggcag ggacatcatt cttaatagat actgaggcca atcccttgaa    1500
cttattcacg agtagtttga taacattctg tcacccgaaa agattctgtt agatggatgc    1560
```

```
agcaactagg atctggtgat aactagcccc gctaccggcg tgattggttg tggtgccaac    1620
gggagccatg ctcacgctgg cctggacgat ccgggaagcc tctcactagc atctccacgc    1680
gtgcaggcgg agggttgaaa aaatgcttgg cctgcttccg tgcatgcagg ctacacccgg    1740
atagtgcagg taaccaatcg tatgcccatt cacggtcaat gcatacaacg agcctgagtg    1800
tagctatccg agcaaccaat cacgtggtac ctgacctaag taatgaccag caaataaaag    1860
tgttgagcac caaatagac aaggtggacg gtccgcatca gtatcgcgtg cagagacagt     1920
tagggttccg agtttcttgt gacggttgtt agctaaattc gcggaattaa ctcgggagat    1980
tggtttgtaa cgggtccaga cccctcctct ataaatataa aggaatacag ttgattggga    2040
taaacaatcg aacctacaat caataaaatt tgcattttat cttgtacatt taggagtcgc    2100
tctagtttag ttctagttta acctctcaat ccccaaattc tctgtttctc ttcggctcta    2160
catcgattat aggtgtctag gtcggcctgc cgactataga caaagcatag gacct         2215
```

<210> SEQ ID NO 127
<211> LENGTH: 1258
<212> TYPE: DNA
<213> ORGANISM: Zea mays

<400> SEQUENCE: 127

```
caattggtgt gggcagccga gcgccatgtt ccagccgctc cggcaacagt gctgccagca      60
gcagatgagg atgatggacg tgcagtccgt cgcgcagcag ctgcagatga tgatgcagct     120
tgagcgtgcc gctgccgcca gcagcagcct gtacgagcca gctctgatgc agcagcagca     180
gcagctgctg gcagcccagg gtctcaaccc catggccatg atgatggcgc agaacatgcc     240
ggccatgggt ggactctacc agtaccagct gcccagctac cgcaccaacc cctgtggcgt     300
ctccgctgcc attccgccct actactgatt catgatattt gggaaatctc ctctatccat     360
ctctctctat ctatatatgt aataatgcag taagacgaca cacattatca tgtgtggtat     420
gaccaataat atatgcatgg tcataataaa gtttggttt taatgaatct atcggccgct      480
tgatgtctat gatggacaaa tcaaaacttc tcctgtcagg catgtaaata tttcaaaatc     540
tctattcagg ctcaaattca tagcatatgg gtagagtagt atgcttgaga ttagcaactt     600
tatacttgag tatagagtat aaaacataaa gtcatgtgta ttctattggc tagataagtg     660
taaatgtgag tttagaggca acaaccatga tttgaatcct aatttacaca taattttagc     720
gttttttcca tttaaaggcg gggcttgacg aagttggaag ccgtggaact gctgggggctt    780 atcttgacaa caaatcattc cggcagagac atcattctta atagatactg aggccaatcc     840
cttgaactta ttcacgagta gtttgataac attctgtcac ccgaaaagat tctgttagat     900
ggatgcagca actaggatct ggtgataact agccccgcta ccggcgtgat tggttgtggt     960
gccaacggga ccatgctca cgctggcctg gacgatccgg gaagcctctc actagcatct      1020
ccacgcgtgc aggcggaggg ttgaaaaaat gcttggcctg cttccgtgca tgcaggctac     1080
acccggatag tgcaggtaac caatcgtatg cccattcacg gtcaatgcat acaacgagcc     1140
tgagtgtagc tatccgagca accaatcacg tggtacctga cctaagtaat gaccagcaaa     1200
taaaagtgtt gagcaccaaa atagacaagg tggacggtcc gcatcagtat cggtcgac       1258
```

<210> SEQ ID NO 128
<211> LENGTH: 832
<212> TYPE: DNA
<213> ORGANISM: Zea mays

<400> SEQUENCE: 128

```
gcggccgcat gcaagagctg ttgatcattc agagcaatgt attggttgtg agttttgac      60 ggcgctcaca gtgatagatt tgttatctat atgccagccc cagcatattc atccttgtgc     120
tgtgggcgtc tagaggaccg acaatatata tattttaaa acaaattcgt gaagaacatc      180
acaagttatg catgcaaact gctcaagtca tgtggatcca aggcatccta acaactagca     240
cagcattaca acaaaatatt ggtgtatatg tgcctacaat gaagtgaaag gtgatgagtc     300
atggtgatgt gtaaagaggc attacaaagt tagcttcaca agcgtatgaa ttcattgaca     360 accettgaca tgtaaagttg attcatatgt ataagaaagc ttaatgatct atctgtaaat     420
ccaaatccat gtactatgtt ccacgtcat gcaacgcaac attccaaaac catgggttgc      480
aagatgctgc agaatgcaag ccatggatca tctataaatg ctagctccc acatatgaac      540 tagtctctat catcatccaa tccagatcag caaagcggca gtgcgtagag aggatcgtcg     600
aacagaacag catgaagatg gtcatcgttc tcgtcgtgtg cctggctctg tcagctgcca     660
gcgcctctgc aatgcagatg ccctgccct gcgcggggct gcagggcttg tacgcgctg      720 gcgccggcct gacgacgatg atgggcgccg gcgggctgta ccctacgcg gagtacctga      780 ggcagccgca gtgcagcccg ctggcggcgg cgccctacta cgccggcaat tg            832

<210> SEQ ID NO 129
<211> LENGTH: 70
<212> TYPE: DNA
<213> ORGANISM: Zea mays

<400> SEQUENCE: 129
gtgcagcccg ctggcggcgg cgccctacta cgccgggtgt gggcagccga gcgccatgtt      60
ccagccgctc                                                             70

<210> SEQ ID NO 130
<211> LENGTH: 76
<212> TYPE: DNA
<213> ORGANISM: Zea mays

<400> SEQUENCE: 130
gtgcagcccg ctggcggcgg cgccctacta cgccggcaat tggtgtgggc agccgagcgc      60
catgttccag ccgctc                                                      76

<210> SEQ ID NO 131
<211> LENGTH: 76
<212> TYPE: DNA
<213> ORGANISM: Zea mays

<400> SEQUENCE: 131
atgggcgccg gcgggctgta ccctacgcg gagtacctga ggcagccgca gtgcagcccg      60
ctggcggcgg cgccct                                                      76

<210> SEQ ID NO 132
<211> LENGTH: 73
<212> TYPE: DNA
<213> ORGANISM: Zea mays

<400> SEQUENCE: 132
atgggcgccg gcgggctgta ccctacgcg gagctgaggc agccgcagtg cagcccgctg      60
gcggcggcgc cct                                                         73

<210> SEQ ID NO 133
<211> LENGTH: 2525
```

```
<212> TYPE: DNA
<213> ORGANISM: Zea mays

<400> SEQUENCE: 133
catactgttg ctgccctgct ggaataaatg tgctactttc ccctgccttg ttaagggaaa      60
gggttttgtt cacgatgtta ccttgtaacc ttgtacttat gtttcatact tggaatgaag     120
gttcatggaa caaaaatatt ctgctgcatt gcatgcaaga gctgttgatc attcagagca     180
atgtattggt tgtgagtttt tgacggcgct cacagtgata gatttgttat ctatatgcca     240
gccccagcat attcatcctt gtgctgtggg cgtctagagg accgacaata tatatatttt     300
taaaacaaat tcgtgaagaa catcacaagt tatgcatgca aactgctcaa gtcatgtgga     360
tccaaggcat cctaacaact agcacagcat tacaacaaaa tattggtgta tatgtgccta     420
caatgaagtg aaaggtgatg agtcatggtg atgtgtaaag aggcattaca aagttagctt     480
cacaagcgta tgaattcatt gacaacccct gacatgtaaa gttgattcat atgtataaga     540
aagcttaatg atctatctgt aaatccaaat ccatgtacta tgtttccacg tcatgcaacg     600
caacattcca aaaccatggg ttgcaagatg ctgcagaatg caagccatgg atcatctata     660
aatggctagc tcccacatat gaactagtct ctatcatcat ccaatccaga tcagcaaagc     720
ggcagtgcgt agagaggatc gtcgaacaga acagcatgaa gatggtcatc gttctcgtcg     780
tgtgcctggc tctgtcagct gccagcgcct tgcaatgca gatgccctgc cctgcgcgg     840
ggctgcaggg cttgtacggc gctggcgccg gcctgacgac gatgatgggc gccggcgggc     900
tgtacccta cgcggagtac ctgaggcagc cgcagtgcag cccgctggcg gcggcgccct     960
actacgccgg gtgtgggcag ccgagcgcca tgttccagcc gctccggcaa cagtgctgcc    1020
agcagcagat gaggatgatg gacgtgcagt ccgtcgcgca gcagctgcag atgatgatgc    1080
agcttgagcg tgccgctgcc gccagcagca gcctgtacga gccagctctg atgcagcagc    1140
agcagcagct gctggcagcc cagggtctca accccatggc catgatgatg gcgcagaaca    1200
tgccggccat gggtggactc taccagtacc agctgcccag ctaccgcacc aaccctgtg    1260
gcgtctccgc tgccattccg ccctactact gattcatgat atttgggaaa tctcctctat    1320
ccatctctct ctatctatat atgtaataat gcagtaagac gacacacatt atcatgtgtg    1380
gtatgaccaa taatatatgc atggtcataa taaagttttg gttttaatga atctatcggc    1440
cgcttgatgt ctatgatgga caaatcaaag cttctcctgt caggcatgta aatatttcaa    1500
aatctctatt caggctcaaa ttcatagcat atgggtagag tagtatgctt gagattagca    1560
actttatact tgagtataga gtataaaaca taaagtcatg tgtattctat tggctagata    1620
agtgtaaatg tgagtttaga ggcaacaacc atgatttgaa tcctaattta cacataattt    1680
tagcgttttt tccatttaaa ggcggggctt gacgaagttg gaagccgtgg aactgctggg    1740
gcttatcttg acaacaaatc attccggcag ggacatcatt cttaatagat actgaggcca    1800
atcccttgaa cttattcacg agtagtttga taacattctg tcacccgaaa agattctgtt    1860
agatggatgc agcaactagg atctggtgat aactagcccc gctaccggcg tgattggttg    1920
tggtgccaac gggagccatg ctcacgctgg cctggacgat ccgggaagcc tctcactagc    1980
atctccacgc gtgcaggcgg agggttgaaa aaatgcttgg cctgcttccg tgcatgcagg    2040
ctacacccgg atagtgcagg taaccaatcg tatgcccatt cacggtcaat gcatacaacg    2100
agcctgagtg tagctatccg agcaaccaat cacgtggtac ctgacctaag taatgaccag    2160
caaataaaag tgttgagcac caaaatagac aaggtggacg gtccgcatca gtatcgcgtg    2220
cagagacagt tagggttccg agtttcttgt gacggttgtt agctaaattc gcggaattaa    2280
```

| | |
|---|---|
| ctcgggagat tggtttgtaa cgggtccaga cccctcctct ataaatataa aggaatacag | 2340 |
| ttgattggga taaacaatcg aacctacaat caataaaatt tgcattttat cttgtacatt | 2400 |
| taggagtcgc tctagtttag ttctagttta acctctcaat ccccaaattc tctgtttctc | 2460 |
| ttcggctcta catcgattat aggtgtctag gtcggcctgc cgactataga caaagcatag | 2520 |
| gacct | 2525 |

<210> SEQ ID NO 134
<211> LENGTH: 4746
<212> TYPE: DNA
<213> ORGANISM: Artificial Sequence
<220> FEATURE:
<223> OTHER INFORMATION: Zp15 donor fragment

<400> SEQUENCE: 134

| | |
|---|---|
| gcatgcaaga gctgttgatc attcagagca atgtattggt tgtgagtttt tgacggcgct | 60 |
| cacagtgata gatttgttat ctatatgcca gccccagcat attcatcctt gtgctgtggg | 120 |
| cgtctagagg accgacaata tatatatttt taaaacaaat tcgtgaagaa catcacaagt | 180 |
| tatgcatgca aactgctcaa gtcatgtgga tccaaggcat cctaacaact agcacagcat | 240 |
| tacaacaaaa tattggtgta tatgtgccta caatgaagtg aaaggtgatg agtcatggtg | 300 |
| atgtgtaaag aggcattaca aagttagctt cacaagcgta tgaattcatt gacaacccttt | 360 |
| gacatgtaaa gttgattcat atgtataaga aagcttaatg atctatctgt aaatccaaat | 420 |
| ccatgtacta tgtttccacg tcatgcaacg caacattcca aaaccatggg ttgcaagatg | 480 |
| ctgcagaatg caagccatgg atcatctata aatggctagc tcccacatat gaactagtct | 540 |
| ctatcatcat ccaatccaga tcagcaaagc ggcagtgcgt agagaggatc gtcgaacaga | 600 |
| acagcatgaa gatggtcatc gttctcgtcg tgtgcctggc tctgtcagct gccagcgcct | 660 |
| ctgcaatgca gatgccctgc ccctgcgcgg ggctgcaggg cttgtacggc gctggcgccg | 720 |
| gcctgacgac gatgatgggc gccggcgggc tgtaccccta cgcggagtac ctgaggcagc | 780 |
| cgcagtgcag cccgctggcg gcggcgccct actacgccgg caattgagca cttaaagatc | 840 |
| tttagaagaa agcaaagcat ttattaatac ataacaatgt ccaggtagcc cagctgaatt | 900 |
| acaatacgca actgctcata ataattcaac aaacccaagt agtacacaac atccagaagc | 960 |
| aaataaagcc catacgtacc aaagcctaca caagcagcaa cactcactgc cagtgccggt | 1020 |
| gggtctttaa agcacacggg ccttgaccac gcgatccacc ttgaaacaaa cttggtaaaa | 1080 |
| ttaaagcaaa ccagaagcac acacacgcca acgcaacgct tctgatcgcg cgcccaaggc | 1140 |
| ccggccggcc agaacgtacg acggacacgc acacgctgcg accgagctct aggtgattaa | 1200 |
| gctaactact cagcgggcag gcctaactcc accaactgtg gtgcgagtca agtatctgaa | 1260 |
| cttgccagca tagtcaggaa cagcacggtg catggtgcac aagttgtccc agacaaggac | 1320 |
| ttggtctttc ttccacctca cacggcaagt gaagtcaaat ctggtggcat gctcatagag | 1380 |
| gaactgaagc aatggctttg attctgcatc tgtcatgccc tcaattctct gacagtagac | 1440 |
| ttgattcaca taaaggcctt tccttccaga gccaggatga gtcacaacca agggatggac | 1500 |
| tgtctctctg tcaccagcat caacatccat caccttgact gaggtgttgc tgaagcgacg | 1560 |
| gttctgtgct tggtagaggg aaccgaacac acgtgtggca gagtgcacaa cgttgagccc | 1620 |
| ttcgatggtg gcttcatgg ttggagacaa ggtctcccaa gctgtgtaca ttgaaaggaa | 1680 |
| cccagtgtct ccgccatgct caggaacatc tatggccctc atcacaacag cagctggagg | 1740 |
| tgcatcaagg aaagtggagt ctgtgtgcca gtcatcacca atcacccttc cagactcatt | 1800 |

```
ggcttctctg cggatcatct gaacctctgg atagccttca atgctcttga gaagaggcac   1860
tggatcaact ggtccaaacc ttcttgagaa tgcaatgtgc tgctcattgg tgattgcttg   1920
gccaggaaag tagatgactt ggtaagtgtg gaaggcatcc aatatctcat tccaggtgct   1980
gtcatcaagt ggttccctca agtccacccc agtgatctca gcaccaagga caccagtgag   2040
tggctggaca gctattctct caaagcgttg ggagagaggg ctgagggcag catgagccat   2100
ggtctaccta caaaaaagct ccgcacgagg ctgcatttgt cacaaatcat gaaaagaaaa   2160
actaccgatg aacaatgctg agggattcaa attctaccca caaaagaag aaagaaagat    2220
ctagcacatc taagcctgac gaagcagcag aaatatataa aaatataaac catagtgccc   2280
tttcccctc ttcctgatct tgtttagcat ggcggaaatt ttaaaccccc catcatctcc    2340
cccaacaacg gcggatcgca gatctacatc cgagagcccc attccccgcg agatccgggc   2400
cggatccacg ccggcgagag ccccagccgc gagatcccgc ccctcccgcg caccgatctg   2460
ggcgcgcacg aagccgcctc tcgcccaccc aaactaccaa ggccaaagat cgagaccgag   2520
acggaaaaaa aaacggaga aggaagagg agaggggcgg ggtggttacc ggcgcggcgg      2580
cggcggaggg ggaggggga ggcgtcgtcc ggcagcgagg ggggaggagg tggaggtggt     2640
ggtggtggtg gtggtagggt tgggggatg ggaggagagg gggggtatg tatatagtgg     2700
cgatgggggg cgtttctttg gaagcggagg gagggccggc ctcgtcgctg gctcgcgatc   2760
ctcctcgcgt ttccggcccc cacgacccgg acccacctgc tgttttttct tttctttt     2820
tttctttctt ttttttttt ttggctgcga gacgtgcggt gcgtgcggac aactcacggt    2880
gatagtgggg gggtgtggag actattgtcc agttggctgg actggggtgg gttgggttgg   2940
gttgggttgg gctgggcttg ctatggatcg tggatagcac tttgggcttt aggaacttta   3000
ggggttgttt ttgtaaatgt tttgagtcta agtttatctt ttattttac tagaaaaaat    3060
acccatgcgc tgcaacgggg gaaagctatt ttaatcttat tattgttcat tgtgagaatt   3120
cgcctgaata tatattttc tcaaaaatta tgtcaaatta gcatatgggt tttttaaag     3180
atatttctta tacaaatccc tctgtattta caaaagcaaa cgaacttaaa acccgactca   3240
aatacagata tgcatttcca aaagcgaata aacttaaaaa ccaattcata caaaaatgac   3300
gtatcaaagt accgacaaaa acatcctcaa tttttataat agtagaaaag agtaaattc    3360
actttgggcc acctttatt accgatattt tacttttatac cacctttta ctgatgtttt   3420
cacttttgac caggtaatct tacctttgtt ttatttgga ctatcccgac tctcttctca   3480
agcatatgaa tgaccaattg gtgtgggcag ccgagcgcca tgttccagcc gctccggcaa   3540
cagtgctgcc agcagcagat gaggatgatg acgtgcagt ccgtcgcgca gcagctgcag   3600
atgatgatgc agcttgagcg tgccgctgcc gccagcagca gcctgtacga gccagctctg   3660
atgcagcagc agcagcagct gctggcagcc cagggtctca accccatggc catgatgatg   3720
gcgcagaaca tgccggccat gggtggactc taccagtacc agctgcccag ctaccgcacc   3780
aaccccgtgt gcgtctccgc tgccattccg ccctactact gattcatgat atttgggaaa   3840
tctcctctat ccatctctct ctatctatat atgtaataat gcagtaagac gacacacatt   3900
atcatgtgtg gtatgaccaa taatatatgc atggtcataa taagttttg gttttaatga    3960
atctatcggc cgcttgatgt ctatgatgga caaatcaaaa cttctcctgt caggcatgta   4020
aatatttcaa aatctctatt caggctcaaa ttcatagcat atgggtagag tagtatgctt   4080
gagattagca actttatact tgagtataga gtataaaaca taaagtcatg tgtattctat   4140
tggctagata agtgtaaatg tgagtttaga ggcaacaacc atgatttgaa tcctaattta   4200
```

| | |
|---|---|
| cacataattt tagcgttttt tccatttaaa ggcggggctt gacgaagttg gaagccgtgg | 4260 |
| aactgctggg gcttatcttg acaacaaatc attccggcag agacatcatt cttaatagat | 4320 |
| actgaggcca atcccttgaa cttattcacg agtagtttga taacattctg tcacccgaaa | 4380 |
| agattctgtt agatggatgc agcaactagg atctggtgat aactagcccc gctaccggcg | 4440 |
| tgattggttg tggtgccaac gggagccatg ctcacgctgg cctggacgat ccgggaagcc | 4500 |
| tctcactagc atctccacgc gtgcaggcgg agggttgaaa aaatgcttgg cctgcttccg | 4560 |
| tgcatgcagg ctacacccgg atagtgcagg taaccaatcg tatgcccatt cacggtcaat | 4620 |
| gcatacaacg agcctgagtg tagctatccg agcaaccaat cacgtggtac ctgacctaag | 4680 |
| taatgaccag caaataaaag tgttgagcac caaaatagac aaggtggacg gtccgcatca | 4740 |
| gtatcg | 4746 |

<210> SEQ ID NO 135
<211> LENGTH: 2176
<212> TYPE: DNA
<213> ORGANISM: Artificial Sequence
<220> FEATURE:
<223> OTHER INFORMATION: 147_5'_Border

<400> SEQUENCE: 135

| | |
|---|---|
| catactgttg ctgccctgct ggaataaatg tgctactttc ccctgccttg ttaagggaaa | 60 |
| gggttttgtt cacgatgtta ccttgtaacc ttgtacttat gtttcatact tggaatgaag | 120 |
| gttcatggaa caaaatatt ctgctgcatt gcatgcaaga gctgttgatc attcagagca | 180 |
| atgtattggt tgtgagtttt tgacggcgct cacagtgata gatttgttat ctatatgcca | 240 |
| gccccagcat attcatcctt gtgctgtggg cgtctagagg accgacaata tatatatttt | 300 |
| taaaacaaat tcgtgaagaa catcacaagt tatgcatgca aactgctcaa gtcatgtgga | 360 |
| tccaaggcat cctaacaact agcacagcat tacaacaaaa tattggtgta tatgtgccta | 420 |
| caatgaagtg aaaggtgatg agtcatggtg atgtgtaaag aggcattaca aagttagctt | 480 |
| cacaagcgta tgaattcatt gacaacccctt gacatgtaaa gttgattcat atgtataaga | 540 |
| aagcttaatg atctatctgt aaatccaaat ccatgtacta tgtttccacg tcatgcaacg | 600 |
| caacattcca aaaccatggg tcgcaagatg ctgcagaatg caagccatgg atcatctata | 660 |
| aatggctagc tcccacatat gaactagtct ctatcatcat ccaatccaga tcagcaaagc | 720 |
| ggcagtgcgt agagaggatc gtcgaacaga acagcatgaa gatggtcatc gttctcgtcg | 780 |
| tgtgcctggc tctgtcagct gccagcgcct ctgcaatgca gatgccctgc cctgcgcgg | 840 |
| ggctgcaggg cttgtacggc gctggcgccg gcctgacgac gatgatgggc accggcgggc | 900 |
| tgtacccta cgcggagtac ctgaggcagc cgcagtgcag cccgctggcg gcggcgccct | 960 |
| actacgccgg caattgagca cttaaagatc tttagaagaa agcaaagcat ttattaatac | 1020 |
| ataacaatgt ccaggtagcc cagctgaatt acaatacgca actgctcata ataattcaac | 1080 |
| aaacccaagt agtacacaac atccagaagc aaataaagcc catacgtacc aaagcctaca | 1140 |
| caagcagcaa cactcactgc cagtgccggt gggtctttaa agcacacggg ccttgaccac | 1200 |
| gcgatccacc ttgaaacaaa cttggtaaaa ttaaagcaaa ccagaagcac acacacgcca | 1260 |
| acgcaacgct tctgatcgcg cgcccaaggc ccggccggcc agaacgtacg acggacacgc | 1320 |
| acacgctgcg accgagctct aggtgattaa gctaactact cagcgggcag gcctaactcc | 1380 |
| accaactgtg gtgcgagtca agtatctgaa cttgccagca tagtcaggaa cagcacggtg | 1440 |
| catggtgcac aagttgtccc agacaaggac ttggtctttc ttccacctca cacggcaagt | 1500 |

| | |
|---|---|
| gaagtcaaat ctggtggcat gctcatagag gaactgaagc aatggctttg attctgcatc | 1560 |
| tgtcatgccc tcaattctct gacagtagac ttgattcaca taaaggcctt tccttccaga | 1620 |
| gccaggatga gtcacaacca agggatggac tgtctctctg tcaccagcat caacatccat | 1680 |
| caccttgact gaggtgttgc tgaagcgacg gttctgtgct tggtagaggg aaccgaacac | 1740 |
| acgtgtggca gagtgcacaa cgttgagccc ttcgatggtg gcttgcatgg ttggagacaa | 1800 |
| ggtctcccaa gctgtgtaca ttgaaaggaa cccagtgtct ccgccatgct caggaacatc | 1860 |
| tatggccctc atcacaacag cagctggagg tgcatcaagg aaagtggagt ctgtgtgcca | 1920 |
| gtcatcacca atcacccttc cagactcatt ggcttctctg cggatcatct gaacctctgg | 1980 |
| atagccttca atgctcttga aagaggcac tggatcaact ggtccaaacc ttcttgagaa | 2040 |
| tgcaatgtgc tgctcattgg tgattgcttg gccaggaaag tagatgactt ggtaagtgtg | 2100 |
| gaaggcatcc aatatctcat tccaggtgct gtcatcaagt ggttccctca agtccacccc | 2160 |
| agtgatctca gcacca | 2176 |

<210> SEQ ID NO 136
<211> LENGTH: 2179
<212> TYPE: DNA
<213> ORGANISM: Artificial Sequence
<220> FEATURE:
<223> OTHER INFORMATION: 147_3'_Border

<400> SEQUENCE: 136

| | |
|---|---|
| tttttggct gcgagacgtg cggtgcgtgc ggacaactcr cggtgatagt gggggggtg | 60 |
| tggagactat tgtccagttg gctggactgg ggtgggttgg gttgggttgg gttgggctgg | 120 |
| gcttgctatg gatcgtggat agcactttgg gctttaggaa ctttaggggt tgttttgta | 180 |
| aatgttttga gtctaagttt atcttttatt tttactagaa aaatacccca tgcgctgcaa | 240 |
| cgggggaaag ctattttaat cttattattg ttcattgtga gaattcgcct gaatatatat | 300 |
| ttttctcaaa aattatgtca aattagcata tgggtttttt taaagatatt tcttatacaa | 360 |
| atccctctgt atttacaaaa gcaaacgaac ttaaaacccg actcaaatac agatatgcat | 420 |
| ttccaaaagc gaataaactt aaaaaccaat tcatacaaaa atgacgtatc aaagtaccga | 480 |
| caaaaacatc ctcaattttt ataatagtag aaaagagtaa atttcacttt gggccaccttt | 540 |
| ttattaccga tatttactt tataccacct tttaactgat gttttcactt ttgaccaggt | 600 |
| aatcttacct tgttttatt ttggactatc ccgactctct tctcaagcat atgaatgacc | 660 |
| aattggtgtg ggcagccgag cgccatgttc cagccgctcc ggcaacagtg ctgccagcag | 720 |
| cagatgagga tgatggacgt gcagtccgtc gcgcagcagc tgcagatgat gatgcagctt | 780 |
| gagcgtgccg ctgccgccag cagcagcctg tacgagccag ctctgatgca gcagcagcag | 840 |
| cagctgctgg cagcccaggg tctcaacccc atggccatga tgatggcgca gaacatgccg | 900 |
| gccatgggtg gactctacca gtaccagctg cccagctacc gcaccaaccc ctgtggcgtc | 960 |
| tccgctgcca ttccgcccta ctactgattc atgatatttg ggaaatctcc tcttccatct | 1020 |
| ctctctatct atatatgtaa taatgcagta agacgacaca cattatcatg tgtggtatga | 1080 |
| ccaataatat atgcatggtc ataataaagt tttggtttta atgaatctat cggccgcttg | 1140 |
| atgtctatga tggacaaatc aaaacttctc ctgtcaggca tgtaaatatt tcaaaatctc | 1200 |
| tattcaggct caaattcata gcatatgggt agagtagtat gcttgagatt agcaacttta | 1260 |
| tacttgagta tagagtataa aacataaagt catgtgtatt ctattggcta gataagtgta | 1320 |
| aatgtgagtt tagaggcaac aaccatgatt tgaatcctaa tttacacata attttagcgt | 1380 |

```
tttttccatt taaaggcggg gcttgacgaa gttggaagcc gtggaactgc tggggcttat    1440
cttgacaaca aatcattccg gcagagacat cattcttaat agatactgag gccaatccct    1500
tgaacttatt cacgagtagt ttgataacat tctgtcaccc gaaaagattc tgttagatga    1560
tgcagcaact aggatctggt gataactagc cccgctaccg gcgtgattgg ttgtggtgcc    1620
aacgggagcc atgctcacgc tggcctggac gatccgggaa gcctctcact agcatctcca    1680
cgcgtgcagg cggagggttg aaaaaatgct tggcctgctt ccgtgcatgc aggctacacc    1740
cggatagtgc aggtaaccaa tcgtatgccc attcacggtc aatgcataca acggcctgag    1800
tgtagctatc cgagcaacca atcacgtggt acctgaccta agtaatgacc agcaaataaa    1860
agtgttgagc accaaaatag acaaggtgga cggtccgcat cagtatcgcg tgcagagaca    1920
gttagggttc cgagtttctt gtgacggttg ttagctaaat tcgcggaatt aactcgggag    1980
attggtttgt aacgggtcca gacccctcct ctataaatat aaaggaatac agttgattgg    2040
gataaacaat cgaacctaca atcaataaaa tttgcatttt atcttgtaca tttaggagtc    2100
gctctagttt agttctagtt taacctctca atccccaaat tctctgtttc tcttcggctc    2160
tacatcgatt ataggtgtc                                                 2179
```